(12) United States Patent
Jimenez et al.

(10) Patent No.: US 10,167,473 B2
(45) Date of Patent: Jan. 1, 2019

(54) SIRNA AND THEIR USE IN METHODS AND COMPOSITIONS FOR INHIBITING THE EXPRESSION OF THE ORAI1 GENE

(71) Applicant: SYLENTIS SAU, Madrid (ES)

(72) Inventors: Ana Isabel Jimenez, Madrid (ES); Covadonga Pañeda, Madrid (ES); Tamara Martinez, Madrid (ES)

(73) Assignee: SYLENTIS SAU, Madrid (ES)

( * ) Notice: Subject to any disclaimer, the term of this patent is extended or adjusted under 35 U.S.C. 154(b) by 0 days.

(21) Appl. No.: 15/030,176

(22) PCT Filed: Oct. 21, 2014

(86) PCT No.: PCT/EP2014/072514
§ 371 (c)(1),
(2) Date: Apr. 18, 2016

(87) PCT Pub. No.: WO2015/059122
PCT Pub. Date: Apr. 30, 2015

(65) Prior Publication Data
US 2016/0304880 A1    Oct. 20, 2016

(30) Foreign Application Priority Data
Oct. 22, 2013  (EP) ..................................... 13382415

(51) Int. Cl.
*C12N 15/113* (2010.01)
(52) U.S. Cl.
CPC ...... *C12N 15/1138* (2013.01); *C12N 2310/14* (2013.01); *C12N 2310/315* (2013.01); *C12N 2310/321* (2013.01); *C12N 2310/50* (2013.01); *C12N 2320/30* (2013.01)

(58) Field of Classification Search
CPC ............ C12N 15/1138; C12N 2310/14; C12N 2310/315; C12N 2310/321; C12N 2310/50; C12N 2320/30
See application file for complete search history.

(56) References Cited

U.S. PATENT DOCUMENTS

| | | | | |
|---|---|---|---|---|
| 8,048,863 | B2* | 11/2011 | Yanni ................. | C12N 15/1137 435/320.1 |
| 8,198,250 | B2* | 6/2012 | Jimenez ............. | C12N 15/1137 514/44 A |
| 2005/0255487 | A1* | 11/2005 | Khvorova ............ | A61K 31/713 435/6.11 |
| 2006/0003322 | A1* | 1/2006 | Bentwich ............. | C12N 15/113 435/6.16 |
| 2011/0105447 | A1* | 5/2011 | Muthuppalaniappan ................... | C07D 231/12 514/171 |

FOREIGN PATENT DOCUMENTS

| | | |
|---|---|---|
| WO | WO 2004/015107 | 2/2004 |
| WO | WO 2008/104978 | 9/2008 |
| WO | WO2008/106731 A1 * | 9/2008 |
| WO | WO 2009/095719 | 8/2009 |

OTHER PUBLICATIONS

Kelmenson et al. 2013, Chapter 17 Treatment of allergic eye disease pp. 117-124, pp. 1-10 Ocular Surface Disease: Cornea, Conjunctiva and Tear Film Author(s): Edward J Holland, Mark J Mannis and W Barry Lee (Year: 2013).*
Angaji et al., "Application of RNA interference in treating human diseases," J. of Genetics, 89(4), pp. 527-537, 2010.
Bacsi et al., "Effect of pollen-mediated oxidative stress on immediate hypersensitivity reactions and late-phase inflammation in allergic conjunctivitis," J. Allergy Clin Immunol., 116(4), pp. 836-843, 2005.
Bramsen et al., "A large-scale chemical modification screen identifies design rules to generate siRNAs with high activity, high stability and low toxicity," Nucleic Acids Research, 37(9), pp. 2867-2881, 2009.
Cerutti et al., "Domains in gene silencing and cell differentiation proteins: the novel PAZ domain and redefinition of the Piwi domain," Protein Sequence Motifs, pp. 481-482, 2000.
Chang et al., "Structural Diversity Repertoire of Gene Silencing Small Interfering RNAs," Nucleic Acid Therapeutics, 21(3), pp. 125-131, 2011.
Collins et al., "Structural domains in RNAi," FEBS Lett., 579(26), pp. 5841-5849, 2005.
Deleavey et al., "Designing Chemically Modified Oligonucleotides for Targeted Gene Silencing," Chemistry & Biology, 19, pp. 937-954 , 2012.
Doench et al., "Specificity of microRNA target selection in translational repression," Genes Dev., 18, pp. 504-511, 2004.
Elbashir et al., "RNA interference is mediated by 21-and 22-nucleotide RNAs," Genes & Development, 15, pp. 188-200, 2001.
Fire et al., "Potent and specific genetic interference by double-stranded RNA in Caenorhabditis elegans," Nature, 39, pp. 806-811, 1998.
Kari et al., "Updates in the treatment of ocular allergies," J. of Asthma and Allergy, 3, pp. 149-158, 2010.
Kay, "Allergy and Allergic Diseases," N. Engl. J. Med., 344(1), pp. 30-37, 2001.
Kim et al., "Synthetic dsRNA Dicer substrates enhance RNAi potency and efficacy," Nature Biotechnology, 23(2), pp. 222-226, 2005.

(Continued)

*Primary Examiner* — Brian A Whiteman
(74) *Attorney, Agent, or Firm* — Margaret B. Brivanlou; Kenneth H. Sonnenfeld; King & Spalding LLP

(57) ABSTRACT

The invention relates to si RNA molecules and their use in methods and pharmaceutical compositions for inhibiting the expression of the ORAI1 gene. The invention also relates to the use of said si RNAs molecules in the treatment and/or prevention of an eye condition characterized by increased expression and/or activity of ORAI1 gene, preferably said eye condition is conjunctivitis and/or an ocular allergy such as seasonal allergic conjunctivitis, perennial allergic conjunctivitis, vernal keratoconjunctivitis, atopic keratoconjunctivitis, and giant papillary conjunctivitis.

18 Claims, 25 Drawing Sheets
Specification includes a Sequence Listing.

(56) References Cited

OTHER PUBLICATIONS

Kornbrust et al., "Oligo Safety Working Group Exaggerated Pharmacology Subcommittee Consensus Document," Nucleic Acid Therapeutics, 23, pp. 21-28, 2013.
La Rosa et al., "Allergic conjunctivitis: a comprehensive review of the literature," Italian Journal of Pediatrics, 39, pp. 1-8, 2013.
Lewis et al., "Prediction of Mammalian MicroRNA Targets," Cell, 115, pp. 787-798, 2003.
Liu et al., "Argonaute2 is the Catalytic Engine of Mammalian RNAi," Science, 305, pp. 1437-1441, 2004.
Livak et al., "Analysis of Relative Gene Expression Data Using Real-Time Quantitative PCR and the $22^{-\Delta\Delta C_T}$ Method," Methods, 25, pp. 402-408, 2001.
Magone et al., "A Novel Murine Model of Allergic Conjunctivitis," Clinical Immunology and Immunopathology, 87(1), pp. 75-84, 1998.
Maniatis, "Separation of RNA According to Size: Electrophoresis of Glyoxylated RNA through Agarose Gels," Molecular Cloning, 5 pages, 1982.
Nykanen et al., "ATP Requirements and Small Interfering RNA Structure in the RNA Interference Pathway," Cell, 107, pp. 309-321, 2001.
Ono et al., "Allergic conjunctivitis: Update on pathophysiology and prospects for future treatment," J. Allergy Clin. Immunol., pp. 118-122, 2005.
Parrish et al., "Functional Anatomy of a dsRNA Trigger: Differential Requirement for the Two Trigger Strands in RNA Interference," Molecular Cell, 6, pp. 1077-1087, 2000.
Popescu, "Antisense-and RNA Interference-Based Therapeutics Strategies in Allergy," J. Cell. Mol. Med., 19(4), pp. 840-853, 2005.
Rand et al., "Argonaute2 Cleaves the Anti-Guide Strand of siRNA during RISC Activation," Cell, 123, pp. 621-629, 2005.
Sanghvi, "A Status Update of Modified Oligonucleotides for Chemotherapeutics Applications," Curr. Protoc. Nucleic Acid Chem., 46, pp. 4.1.1-4.1.22, 2011.
Song, et al., "Crystal Structure of Argonaute and Its Implications for RISC Slicer Activity," Science, 305, pp. 1434-1437, 2004.
Suzuki et al., "Inhibition of allergic responses by CD40 gene silencing," Allergy, 64, pp. 387-397, 2009.
Suzuki, et al., "A novel allergen-specific therapy for allergy using CD40-silenced dendritic cells," J. Allergy Clin. Immunol., pp. 737-743e6, 2010.
Walton et al., "Designing Highly Active siRNAs for Therapeutic Applications," FEBS J., 277(23), pp. 4806-4813, 2010.
Baba et al., "Essential function for the calcium sensor STIM1 in mast cell activation and anaphylactic responses," Nature Immunology, 9(1), pp. 81-88, 2008.
Baumann et al., "Extracellular Protons Both Increase the Activity and Reduce the Conductance of Capsaicin-Gated Channels," The Journal of Neuroscience, 20, pp. 1-5, 2000.
Bergmeier et al., Emerging Roles of Store-Operated Ca(2+) Entry through STIM and ORAI Protein in Immunity, Hemostasis and Cancer, Landes Bioscience, retrieved from www.ncbi.nlm.nih.gov/pubmed/23511024, 1 page, 2013.
Caterina et al., "The capsaicin receptor: a heat-activated ion channel in the pain pathway," Nature, 389, pp. 816-824, 1997.
Caterina et al., "The Vanilloid Receptor: A Molecular Gateway to the Pain Pathway," Annu. Rev. Neurosci., 24, pp. 487-517, 2001.
Gonzalez et al., "Reduction of Capsaicin-Induced Ocular Pain and Neurogenic Inflammation by Calcium Antagonists," Investigative Ophthalmology & Visual Science, 34(12), pp. 3329-3335, 1993.
Hoth et al., "Depletion of Intracellular Calcium Stores Activates a Calcium Current in Mast Cells," Nature, 355, pp. 353-356, 1992.
Hutvagner et al., "A microRNA in a Multiple-Turnover RNAi Enzyme Complex," Science, 297, pp. 2056-2060, 2002.
Ma et al., "Structural basis for 5'-end-specific recognition of guide RNA by the A. fulgidus Piwi protein," Nature, 434, pp. 666-670, 2005.
Orban et al., "Decay of mRNAs targeted by RISC requires XRN1, the Ski complex, and the exosome," RNA, 11, pp. 459-469, 2005.
Paddison et al., "Short hairpin RNAs (shRNAs) induce sequence-specific silencing in mammalian cells," Genes Dev, 16, pp. 948-958, 2002.
Parekh et al., "Store-Operated Calcium Channels," Physiol. Rev., 85, pp. 757-810, 2005.
Reynolds et al., "Rational siRNA Design for RNA Interference," Nature Biotechnology, 22(3), pp. 326-330, 2004.
Schubert et al, "Local RNA Target Structures Influences siRNA Efficacy: Systematic Analysis of Intentionally Designed Binding Regions," J. Mol. Biol., 348, pp. 883-893, 2005.
Smyth et al., "Emerging perspectives in store-operated $Ca^{2+}$ entry: Roles of Orai, Stim and TRP," Biochimica et Biophysica Acta, 1763, pp. 1147-1160, 2006.
Ui-Tei et al., "Guidelines for the selection of highly effective siRNA sequences for mammalian and chick RNA interference," Nucleic Acids Research, 32(3), pp. 936-948, 2004.
Vig et al., "A major defect in mast cell effector functions in CRACM1-/- mice," Nat. Immunol., 9(1), pp. 89-96, 2008.
Zheng et al., "TSLP and Downstream Molecules in Experimental Mouse Allergic Conjunctivitis," Immunology and Microbiology, 51(6), pp. 3076-3082 2010.
Huang et al., "Histamine Regulates Cyclooxygenase 2 Gene Activation Through Orai1-Mediated NFκB Activation in Lung Cancer Cells," Cell Calcium, vol. 50, No. 1, pp. 27-35, 2011.
Vig et al., "Defective Mast Cell Effector Functions in Mice Lacking the CRACM1 Pore Subunit of Store-Operated Calcium Release-Activated Calcium Channels," Nature Immunology, vol. 9, No. 1, pp. 89-96, Dec. 2, 2007.
Wang et al., "Downregulation of Orai1 Expression in the Airway Alleviates Murine Allergic Rhinitis," Experimental and Molecular Medicine, vol. 44, No. 3, pp. 177-190, 2012.
Yang et al., "Involvement of STIM1 and Orai in EGF-Mediated Cell Growth in Retinal Pigment Epithelial Cells," Journal of Biomedical Science, 20:41, pp. 1-11, 2013.

* cited by examiner

| ORAI1 target sequences (cDNA) | |
|---|---|
| SEQ ID NO. 1 | TGATGAGCCTCAACGAGCA |
| SEQ ID NO. 2 | GGACTGGATCGGCCAGAGT |
| SEQ ID NO. 3 | CCGAGGTGATGAGCCTCAA |
| SEQ ID NO. 4 | CTGTCCTGGCGCAAGCTCT |
| SEQ ID NO. 5 | CCTGCATCCTGCCCAACAT |
| SEQ ID NO. 6 | GCATCCTGCCCAACATCGA |
| SEQ ID NO. 7 | AGGTGATGAGCCTCAACGA |
| SEQ ID NO. 8 | TGTCCTGGCGCAAGCTCTA |
| SEQ ID NO. 9 | CGCCGGAGCCGCCGCCGCA |
| SEQ ID NO. 10 | GCCGCCGCCGCAGCGGGGA |
| SEQ ID NO. 11 | GCCGCAGCGGGGACGGGGA |
| SEQ ID NO. 12 | CGCTGTCCTGGCGCAAGCT |
| SEQ ID NO. 13 | CCTGGCGCAAGCTCTACTT |
| SEQ ID NO. 14 | GCGCAAGCTCTACTTGAGC |
| SEQ ID NO. 15 | GCCCCCGAGCCGCAGCAGT |
| SEQ ID NO. 16 | CCCCGAGCCGCAGCAGTCC |
| SEQ ID NO. 17 | GCCGCAGCAGTCCCGAGCT |
| SEQ ID NO. 18 | CCGCAGCAGTCCCGAGCTT |
| SEQ ID NO. 19 | CGCAGCAGTCCCGAGCTTC |
| SEQ ID NO. 20 | CCCCAAGCGGCGGCAGCA |
| SEQ ID NO. 21 | CCCCAAGCGGCGGCAGCAC |
| SEQ ID NO. 22 | GGCAGCACCACCAGCGGCA |
| SEQ ID NO. 23 | GCCCCGGGGGCCCCGCCA |
| SEQ ID NO. 24 | GCCCCGCCACCGCCGCCGT |
| SEQ ID NO. 25 | CCGCCGCCGTCCGCCGTCA |
| SEQ ID NO. 26 | CCGCCGTCCGCCGTCACCT |
| SEQ ID NO. 27 | CGCCGTCCGCCGTCACCTA |
| SEQ ID NO. 28 | GCCGTCCGCCGTCACCTAC |
| SEQ ID NO. 29 | CCGCCGTCACCTACCCGGA |
| SEQ ID NO. 30 | GCCGTCACCTACCCGGACT |
| SEQ ID NO. 31 | CACCTACCCGGACTGGATC |
| SEQ ID NO. 32 | CCGGACTGGATCGGCCAGA |
| SEQ ID NO. 33 | GACTGGATCGGCCAGAGTT |

FIGURE 1

| | |
|---|---|
| SEQ ID NO. 34 | ACTGGATCGGCCAGAGTTA |
| SEQ ID NO. 35 | GCCAGAGTTACTCCGAGGT |
| SEQ ID NO. 36 | CAGAGTTACTCCGAGGTGA |
| SEQ ID NO. 37 | GCCTCAACGAGCACTCCAT |
| SEQ ID NO. 38 | TCAACGAGCACTCCATGCA |
| SEQ ID NO. 39 | CACTCCATGCAGGCGCTGT |
| SEQ ID NO. 40 | CTTGAGCCGCGCCAAGCTT |
| SEQ ID NO. 41 | TGAGCCGCGCCAAGCTTAA |
| SEQ ID NO. 42 | GAGCCGCGCCAAGCTTAAA |
| SEQ ID NO. 43 | CGCGCCAAGCTTAAAGCCT |
| SEQ ID NO. 44 | GCGCCAAGCTTAAAGCCTC |
| SEQ ID NO. 45 | CGCCAAGCTTAAAGCCTCC |
| SEQ ID NO. 46 | GCCAAGCTTAAAGCCTCCA |
| SEQ ID NO. 47 | CCAGCCGGACCTCGGCTCT |
| SEQ ID NO. 48 | GCCGGACCTCGGCTCTGCT |
| SEQ ID NO. 49 | CGGACCTCGGCTCTGCTCT |
| SEQ ID NO. 50 | CGGCTCTGCTCTCCGGCTT |
| SEQ ID NO. 51 | GGCTCTGCTCTCCGGCTTC |
| SEQ ID NO. 52 | CGGCTTCGCCATGGTGGCA |
| SEQ ID NO. 53 | GGCTTCGCCATGGTGGCAA |
| SEQ ID NO. 54 | GCTTCGCCATGGTGGCAAT |
| SEQ ID NO. 55 | CTGGACGCTGACCACGACT |
| SEQ ID NO. 56 | CGCTGACCACGACTACCCA |
| SEQ ID NO. 57 | CCCACCGGGGCTGCTCATC |
| SEQ ID NO. 58 | CCGGGGCTGCTCATCGCCT |
| SEQ ID NO. 59 | CGGGGCTGCTCATCGCCTT |
| SEQ ID NO. 60 | GGGGCTGCTCATCGCCTTC |
| SEQ ID NO. 61 | GGGCTGCTCATCGCCTTCA |
| SEQ ID NO. 62 | GCTGCTCATCGCCTTCAGT |
| SEQ ID NO. 63 | GCCTTCAGTGCCTGCACCA |
| SEQ ID NO. 64 | CCTGCACCACAGTGCTGGT |
| SEQ ID NO. 65 | CCACAGTGCTGGTGGCTGT |
| SEQ ID NO. 66 | CTGGTGGCTGTGCACCTGT |
| SEQ ID NO. 67 | GGTGGCTGTGCACCTGTTT |
| SEQ ID NO. 68 | GTGCACCTGTTTGCGCTCA |

FIGURE 1 Cont'd

| SEQ ID NO. 69 | CACCTGTTTGCGCTCATGA |
| SEQ ID NO. 70 | CTGTTTGCGCTCATGATCA |
| SEQ ID NO. 71 | GCGCTCATGATCAGCACCT |
| SEQ ID NO. 72 | GCACCTGCATCCTGCCCAA |
| SEQ ID NO. 73 | CCCAACATCGAGGCGGTGA |
| SEQ ID NO. 74 | GCGGTGAGCAACGTGCACA |
| SEQ ID NO. 75 | CGGTGAGCAACGTGCACAA |
| SEQ ID NO. 76 | GGTGAGCAACGTGCACAAT |
| SEQ ID NO. 77 | TGAGCAACGTGCACAATCT |
| SEQ ID NO. 78 | GCAACGTGCACAATCTCAA |
| SEQ ID NO. 79 | CACAATCTCAACTCGGTCA |
| SEQ ID NO. 80 | ACAATCTCAACTCGGTCAA |
| SEQ ID NO. 81 | CTCAACTCGGTCAAGGAGT |
| SEQ ID NO. 82 | CGGTCAAGGAGTCCCCCCA |
| SEQ ID NO. 83 | GGTCAAGGAGTCCCCCCAT |
| SEQ ID NO. 84 | TTGAGATTGTGCACGTTGC |
| SEQ ID NO. 85 | ATTGTGCACGTTGCTCACC |
| SEQ ID NO. 86 | ATCACCTCGGAGTAACTCT |
| SEQ ID NO. 87 | ATGGAGTGCTCGTTGAGGC |
| SEQ ID NO. 88 | ATCATGAGCGCAAACAGGT |
| SEQ ID NO. 89 | ATGTTGGGCAGGATGCAGG |
| SEQ ID NO. 90 | AAGTAGAGCTTGCGCCAGG |
| SEQ ID NO. 91 | CTCATCACCTCGGAGTAAC |
| SEQ ID NO. 92 | AGATTGTGCACGTTGCTCA |
| SEQ ID NO. 93 | AGTAACTCTGGCCGATCCA |
| SEQ ID NO. 94 | ATGCGCTCATGGGGGACT |
| SEQ ID NO. 95 | GCAACGTGCACAATCTCAA |
| SEQ ID NO. 96 | CGGTGAGCAACGTGCACAA |
| SEQ ID NO. 97 | GCAACGTGCACAATCTCAA |
| SEQ ID NO. 98 | ACTGGATCGGCCAGAGTTA |
| SEQ ID NO. 99 | AGAGTTACTCCGAGGTGAT |
| SEQ ID NO. 100 | GCCTCAACGAGCACTCCAT |
| SEQ ID NO. 101 | GGCGCAAGCTCTACTTGAG |
| SEQ ID NO. 102 | GGCTTCGCCATGGTGGCAA |
| SEQ ID NO. 103 | GCTTCGCCATGGTGGCAAT |

FIGURE 1 Cont'd

| | |
|---|---|
| SEQ ID NO. 104 | TGGACGCTGACCACGACTA |
| SEQ ID NO. 105 | CGGGGCTGCTCATCGCCTT |
| SEQ ID NO. 106 | GCACCTGCATCCTGCCCAA |
| SEQ ID NO. 107 | ACATCGAGGCGGTGAGCAA |
| SEQ ID NO. 108 | CGGTGAGCAACGTGCACAA |
| SEQ ID NO. 109 | GGTGAGCAACGTGCACAAT |
| SEQ ID NO. 110 | GCAACGTGCACAATCTCAA |
| SEQ ID NO. 111 | ACAATCTCAACTCGGTCAA |

FIGURE 1 Cont'd

| ORAI1 siRNAs | Sense strand 5'→3' | Antisense strand 5'→3' |
|---|---|---|
| SEQ ID NO. 112 | UGAUGAGCCUCAACGAGCA | UGCUCGUUGAGGCUCAUCA |
| SEQ ID NO. 113 | GGACUGGAUCGGCCAGAGU | ACUCUGGCCGAUCCAGUCC |
| SEQ ID NO. 114 | CCGAGGUGAUGAGCCUCAA | UUGAGGCUCAUCACCUCGG |
| SEQ ID NO. 115 | CUGUCCUGGCGCAAGCUCU | AGAGCUUGCGCCAGGACAG |
| SEQ ID NO. 116 | CCUGCAUCCUGCCCAACAU | AUGUUGGGCAGGAUGCAGG |
| SEQ ID NO. 117 | GCAUCCUGCCCAACAUCGA | UCGAUGUUGGGCAGGAUGC |
| SEQ ID NO. 118 | AGGUGAUGAGCCUCAACGA | UCGUUGAGGCUCAUCACCU |
| SEQ ID NO. 119 | UGUCCUGGCGCAAGCUCUA | UAGAGCUUGCGCCAGGACA |
| SEQ ID NO. 120 | CGCCGGAGCCGCCGCCGCA | UGCGGCGGCGGCUCCGGCG |
| SEQ ID NO. 121 | GCCGCCGCCGCAGCGGGGA | UCCCCGCUGCGGCGGCGGC |
| SEQ ID NO. 122 | GCCGCAGCGGGGACGGGGA | UCCCCGUCCCCGCUGCGGC |
| SEQ ID NO. 123 | CGCUGUCCUGGCGCAAGCU | AGCUUGCGCCAGGACAGCG |
| SEQ ID NO. 124 | CCUGGCGCAAGCUCUACUU | AAGUAGAGCUUGCGCCAGG |
| SEQ ID NO. 125 | GCGCAAGCUCUACUUGAGC | GCUCAAGUAGAGCUUGCGC |
| SEQ ID NO. 126 | GCCCCCGAGCCGCAGCAGU | ACUGCUGCGGCUCGGGGGC |
| SEQ ID NO. 127 | CCCCGAGCCGCAGCAGUCC | GGACUGCUGCGGCUCGGGG |
| SEQ ID NO. 128 | GCCGCAGCAGUCCCGAGCU | AGCUCGGGACUGCUGCGGC |
| SEQ ID NO. 129 | CCGCAGCAGUCCCGAGCUU | AAGCUCGGGACUGCUGCGG |
| SEQ ID NO. 130 | CGCAGCAGUCCCGAGCUUC | GAAGCUCGGGACUGCUGCG |
| SEQ ID NO. 131 | CCCCCAAGCGGCGGCAGCA | UGCUGCCGCCGCUUGGGGG |
| SEQ ID NO. 132 | CCCCAAGCGGCGGCAGCAC | GUGCUGCCGCCGCUUGGGG |
| SEQ ID NO. 133 | GGCAGCACCACCAGCGGCA | UGCCGCUGGUGGUGCUGCC |
| SEQ ID NO. 134 | GCCCCCGGGGCCCCGCCA | UGGCGGGGCCCCGGGGGGC |
| SEQ ID NO. 135 | GCCCCGCCACCGCCGCCGU | ACGGCGGCGGUGGCGGGGC |
| SEQ ID NO. 136 | CCGCCGCCGUCCGCCGUCA | UGACGGCGGACGGCGGCGG |
| SEQ ID NO. 137 | CCGCCGUCCGCCGUCACCU | AGGUGACGGCGGACGGCGG |
| SEQ ID NO. 138 | CGCCGUCCGCCGUCACCUA | UAGGUGACGGCGGACGGCG |
| SEQ ID NO. 139 | GCCGUCCGCCGUCACCUAC | GUAGGUGACGGCGGACGGC |
| SEQ ID NO. 140 | CCGCCGUCACCUACCCGGA | UCCGGGUAGGUGACGGCGG |
| SEQ ID NO. 141 | GCCGUCACCUACCCGGACU | AGUCCGGGUAGGUGACGGC |
| SEQ ID NO. 142 | CACCUACCCGGACUGGAUC | GAUCCAGUCCGGGUAGGUG |
| SEQ ID NO. 143 | CCGGACUGGAUCGGCCAGA | UCUGGCCGAUCCAGUCCGG |

FIGURE 2

| SEQ ID NO. 144 | GACUGGAUCGGCCAGAGUU | AACUCUGGCCGAUCCAGUC |
| --- | --- | --- |
| SEQ ID NO. 145 | ACUGGAUCGGCCAGAGUUA | UAACUCUGGCCGAUCCAGU |
| SEQ ID NO. 146 | GCCAGAGUUACUCCGAGGU | ACCUCGGAGUAACUCUGGC |
| SEQ ID NO. 147 | CAGAGUUACUCCGAGGUGA | UCACCUCGGAGUAACUCUG |
| SEQ ID NO. 148 | GCCUCAACGAGCACUCCAU | AUGGAGUGCUCGUUGAGGC |
| SEQ ID NO. 149 | UCAACGAGCACUCCAUGCA | UGCAUGGAGUGCUCGUUGA |
| SEQ ID NO. 150 | CACUCCAUGCAGGCGCUGU | ACAGCGCCUGCAUGGAGUG |
| SEQ ID NO. 151 | CUUGAGCCGCGCCAAGCUU | AAGCUUGGCGCGGCUCAAG |
| SEQ ID NO. 152 | UGAGCCGCGCCAAGCUUAA | UUAAGCUUGGCGCGGCUCA |
| SEQ ID NO. 153 | GAGCCGCGCCAAGCUUAAA | UUUAAGCUUGGCGCGGCUC |
| SEQ ID NO. 154 | CGCGCCAAGCUUAAAGCCU | AGGCUUUAAGCUUGGCGCG |
| SEQ ID NO. 155 | GCGCCAAGCUUAAAGCCUC | GAGGCUUUAAGCUUGGCGC |
| SEQ ID NO. 156 | CGCCAAGCUUAAAGCCUCC | GGAGGCUUUAAGCUUGGCG |
| SEQ ID NO. 157 | GCCAAGCUUAAAGCCUCCA | UGGAGGCUUUAAGCUUGGC |
| SEQ ID NO. 158 | CCAGCCGGACCUCGGCUCU | AGAGCCGAGGUCCGGCUGG |
| SEQ ID NO. 159 | GCCGGACCUCGGCUCUGCU | AGCAGAGCCGAGGUCCGGC |
| SEQ ID NO. 160 | CGGACCUCGGCUCUGCUCU | AGAGCAGAGCCGAGGUCCG |
| SEQ ID NO. 161 | CGGCUCUGCUCUCCGGCUU | AAGCCGGAGAGCAGAGCCG |
| SEQ ID NO. 162 | GGCUCUGCUCUCCGGCUUC | GAAGCCGGAGAGCAGAGCC |
| SEQ ID NO. 163 | CGGCUUCGCCAUGGUGGCA | UGCCACCAUGGCGAAGCCG |
| SEQ ID NO. 164 | GGCUUCGCCAUGGUGGCAA | UUGCCACCAUGGCGAAGCC |
| SEQ ID NO. 165 | GCUUCGCCAUGGUGGCAAU | AUUGCCACCAUGGCGAAGC |
| SEQ ID NO. 166 | CUGGACGCUGACCACGACU | AGUCGUGGUCAGCGUCCAG |
| SEQ ID NO. 167 | CGCUGACCACGACUACCCA | UGGGUAGUCGUGGUCAGCG |
| SEQ ID NO. 168 | CCCACCGGGGCUGCUCAUC | GAUGAGCAGCCCCGGUGGG |
| SEQ ID NO. 169 | CCGGGGCUGCUCAUCGCCU | AGGCGAUGAGCAGCCCCGG |
| SEQ ID NO. 170 | CGGGGCUGCUCAUCGCCUU | AAGGCGAUGAGCAGCCCCG |
| SEQ ID NO. 171 | GGGGCUGCUCAUCGCCUUC | GAAGGCGAUGAGCAGCCCC |
| SEQ ID NO. 172 | GGGCUGCUCAUCGCCUUCA | UGAAGGCGAUGAGCAGCCC |
| SEQ ID NO. 173 | GCUGCUCAUCGCCUUCAGU | ACUGAAGGCGAUGAGCAGC |
| SEQ ID NO. 174 | GCCUUCAGUGCCUGCACCA | UGGUGCAGGCACUGAAGGC |
| SEQ ID NO. 175 | CCUGCACCACAGUGCUGGU | ACCAGCACUGUGGUGCAGG |
| SEQ ID NO. 176 | CCACAGUGCUGGUGGCUGU | ACAGCCACCAGCACUGUGG |
| SEQ ID NO. 177 | CUGGUGGCUGUGCACCUGU | ACAGGUGCACAGCCACCAG |

FIGURE 2 Cont'd

| | | |
|---|---|---|
| SEQ ID NO. 178 | GGUGGCUGUGCACCUGUUU | AAACAGGUGCACAGCCACC |
| SEQ ID NO. 179 | GUGCACCUGUUUGCGCUCA | UGAGCGCAAACAGGUGCAC |
| SEQ ID NO. 180 | CACCUGUUUGCGCUCAUGA | UCAUGAGCGCAAACAGGUG |
| SEQ ID NO. 181 | CUGUUUGCGCUCAUGAUCA | UGAUCAUGAGCGCAAACAG |
| SEQ ID NO. 182 | GCGCUCAUGAUCAGCACCU | AGGUGCUGAUCAUGAGCGC |
| SEQ ID NO. 183 | GCACCUGCAUCCUGCCCAA | GCACCUGCAUCCUGCCCAA |
| SEQ ID NO. 184 | CCCAACAUCGAGGCGGUGA | UCACCGCCUCGAUGUUGGG |
| SEQ ID NO. 185 | GCGUGAGCAACGUGCACA | UGUGCACGUUGCUCACCGC |
| SEQ ID NO. 186 | CGGUGAGCAACGUGCACAA | UUGUGCACGUUGCUCACCG |
| SEQ ID NO. 187 | GGUGAGCAACGUGCACAAU | AUUGUGCACGUUGCUCACC |
| SEQ ID NO. 188 | UGAGCAACGUGCACAAUCU | AGAUUGUGCACGUUGCUCA |
| SEQ ID NO. 189 | GCAACGUGCACAAUCUCAA | UUGAGAUUGUGCACGUUGC |
| SEQ ID NO. 190 | CACAAUCUCAACUCGGUCA | UGACCGAGUUGAGAUUGUG |
| SEQ ID NO. 191 | ACAAUCUCAACUCGGUCAA | UUGACCGAGUUGAGAUUGU |
| SEQ ID NO. 192 | CUCAACUCGGUCAAGGAGU | ACUCCUUGACCGAGUUGAG |
| SEQ ID NO. 193 | CGGUCAAGGAGUCCCCCCA | UGGGGGGACUCCUUGACCG |
| SEQ ID NO. 194 | GGUCAAGGAGUCCCCCCAU | AUGGGGGGACUCCUUGACC |
| SEQ ID NO. 195 | UUGAGAUUGUGCACGUUGC | GCAACGUGCACAAUCUCAA |
| SEQ ID NO. 196 | AUUGUGCACGUUGCUCACC | GGUGAGCAACGUGCACAAU |
| SEQ ID NO. 197 | AUCACCUCGGAGUAACUCU | AGAGUUACUCCGAGGUGAU |
| SEQ ID NO. 198 | AUGGAGUGCUCGUUGAGGC | GCCUCAACGAGCACUCCAU |
| SEQ ID NO. 199 | AUCAUGAGCGCAAACAGGU | ACCUGUUUGCGCUCAUGAU |
| SEQ ID NO. 200 | AUGUUGGCAGGAUGCAGG | CCUGCAUCCUGCCAACAU |
| SEQ ID NO. 201 | AAGUAGAGCUUGCGCCAGG | CCUGGCGCAAGCUCUACUU |
| SEQ ID NO. 202 | CUCAUCACCUCGGAGUAAC | GUUACUCCGAGGUGAUGAG |
| SEQ ID NO. 203 | AGAUUGUGCACGUUGCUCA | UGAGCAACGUGCACAAUCU |
| SEQ ID NO. 204 | AGUAACUCUGGCCGAUCCA | UGGAUCGGCCAGAGUUACU |
| SEQ ID NO. 205 | AUGCGCUCAUGGGGGGACU | AGUCCCCCAUGAGCGCAU |
| SEQ ID NO. 206 | GCAACGUGCACAAUCUCAA | UUGAGAUUGUGCACGUUGC |
| SEQ ID NO. 207 | CGGUGAGCAACGUGCACAA | UUGUGCACGUUGCUCACCG |
| SEQ ID NO. 208 | GCAACGUGCACAAUCUCAA | UUGAGAUUGUGCACGUUGC |
| SEQ ID NO. 209 | ACUGGAUCGGCCAGAGUUA | UAACUCUGGCCGAUCCAGU |
| SEQ ID NO. 210 | AGAGUUACUCCGAGGUGAU | AUCACCUCGGAGUAACUCU |
| SEQ ID NO. 211 | GCCUCAACGAGCACUCCAU | AUGGAGUGCUCGUUGAGGC |

FIGURE 2 Cont'd

| SEQ ID NO. 212 | GGCGCAAGCUCUACUUGAG | CUCAAGUAGAGCUUGCGCC |
| SEQ ID NO. 213 | GGCUUCGCCAUGGUGGCAA | UUGCCACCAUGGCGAAGCC |
| SEQ ID NO. 214 | GCUUCGCCAUGGUGGCAAU | AUUGCCACCAUGGCGAAGC |
| SEQ ID NO. 215 | UGGACGCUGACCACGACUA | UAGUCGUGGUCAGCGUCCA |
| SEQ ID NO. 216 | CGGGGCUGCUCAUCGCCUU | AAGGCGAUGAGCAGCCCCG |
| SEQ ID NO. 217 | GCACCUGCAUCCUGCCCAA | UUGGGCAGGAUGCAGGUGC |
| SEQ ID NO. 218 | ACAUCGAGGCGGUGAGCAA | UUGCUCACCGCCUCGAUGU |
| SEQ ID NO. 219 | CGGUGAGCAACGUGCACAA | UUGUGCACGUUGCUCACCG |
| SEQ ID NO. 220 | GGUGAGCAACGUGCACAAU | AUUGUGCACGUUGCUCACC |
| SEQ ID NO. 221 | GCAACGUGCACAAUCUCAA | UUGAGAUUGUGCACGUUGC |
| SEQ ID NO. 222 | ACAAUCUCAACUCGGUCAA | UUGACCGAGUUGAGAUUGU |

FIGURE 2 Cont'd

| Modified ORAI1 siRNAs | Sense strand 5´-3´ | Antisense strand 5´-3´ | siRNA Length (nt) | Modifications |
|---|---|---|---|---|
| SEQ ID NO. 223 | UGAUGAGCCUCaaCGaGCa | UGCUCGUUGAGGCUCAUCA | 19 | 2'OMe(S) |
| SEQ ID NO. 224 | UGAUGAGCCUCaaCGaGCa | U*GCUCGUUGAGGCUCAUC*A (SEQ ID NO. 230) | 19 | 2'OMe(S)/PS (AS) |
| SEQ ID NO. 225 | U*GAUGAGCCUCaaCGaGC*a | U*GCUCGUUGAGGCUCAUC*A (SEQ ID NO. 231) | 19 | 2'OMe+PS (S)/PS (AS) |
| SEQ ID NO. 226 | U*GAUGAGCCUCaaCGaGC*a | UGCUCGUUGAGGCUCAUCA | 19 | 2'OMe+PS (S) |
| SEQ ID NO. 227 | U*GAUGAGCCUCAAcGaGc*A | UGCUCGUUGAGGCUCAUCA | 19 | 2'OMe+PS (S) |
| SEQ ID NO. 228 | dTGAdTGAGCCUCAACGAGCA | UGCUCGUUGAGGCUCAUCA | 19 | deoxiribonucleotide (2'H) (S) |
| SEQ ID NO. 229 | dTGAdTGAGCCUCAACGAGCA | DTGCdTCGdTUGAGGCUCAUCA (SEQ ID NO: 232) | 19 | deoxiribonucleotide (2'H) (S&AS) |
| SEQ ID NO. 233 | uGAUGAGCCUCAACGAGCA | 1GCUCGUUGAGGCUCAUCA (SEQ ID NO. 234) | 19 | 2'OMe(S)/2'FU(AS) |
| SEQ ID NO. 235 | uGAUGAGCCUCAACGAGCA | U*GCUCGUUGAGGCUCAUCA (SEQ ID NO. 236) | 19 | 2'OMe(S)/PS (AS) |
| Lower case: 2'OMe ribonucleotides | | | | |
| 1: 2'FU ribonucleotide | | | | |
| *: Phosphothioate bond | | | | |
| d(nt) : deoxiribonucleotide dT, dA, dG, dC | | | | |

FIGURE 3

A.
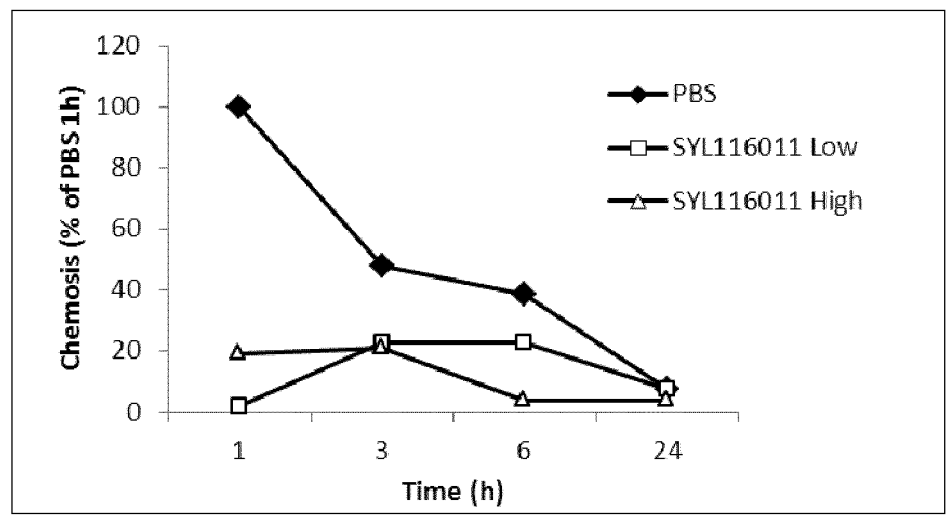
B.
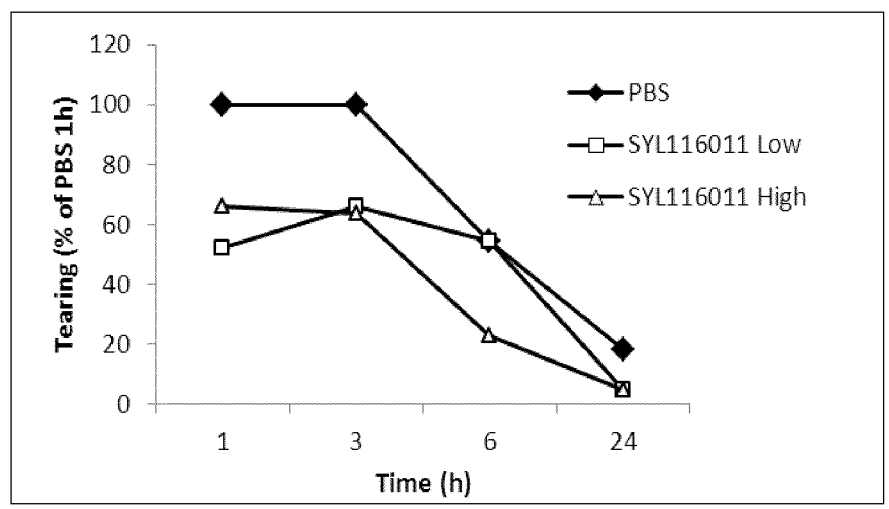
FIGURE 21

A.
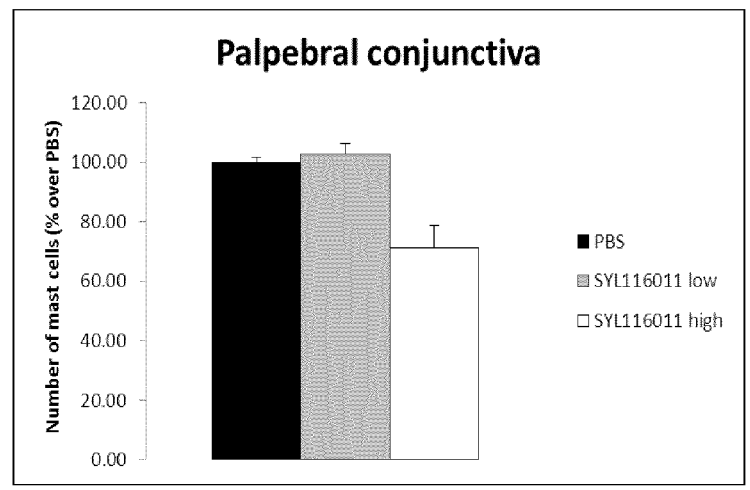
B.
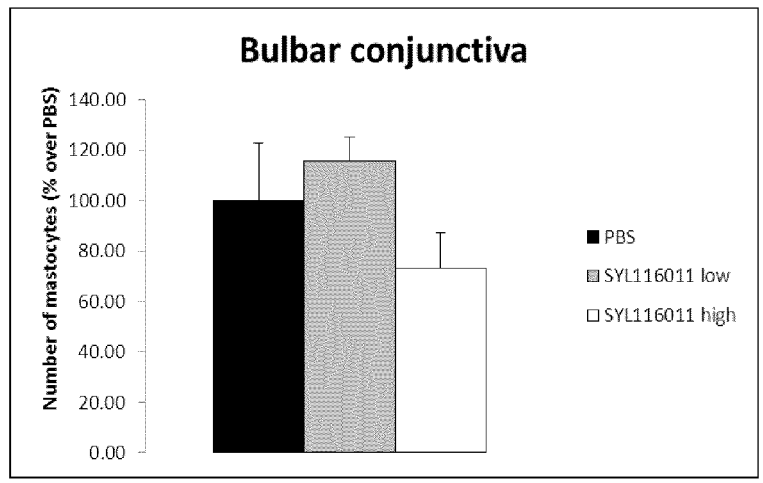
FIGURE 22

A.
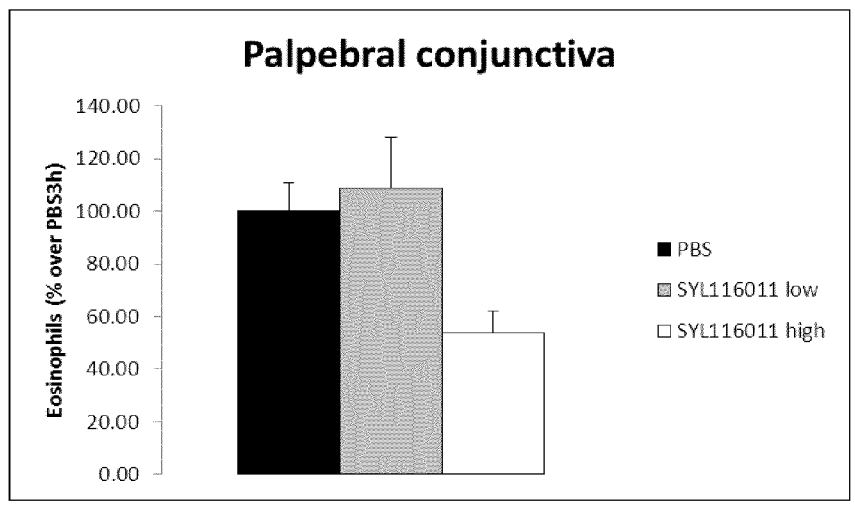
B.
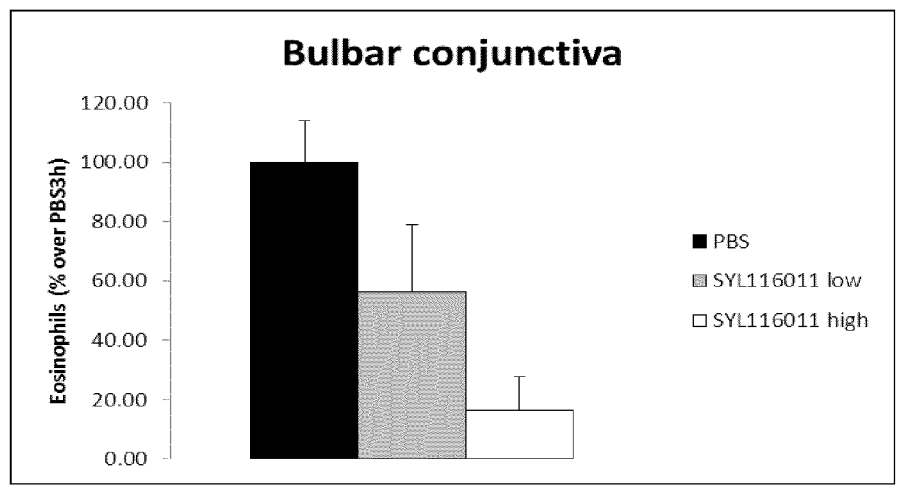
FIGURE 23

A.
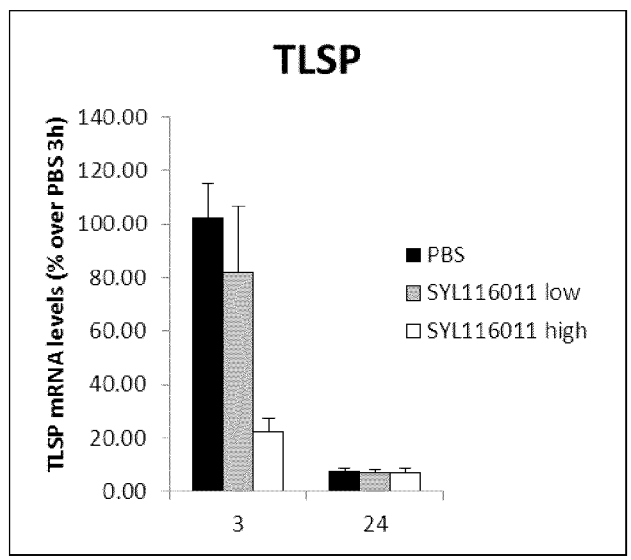
B.
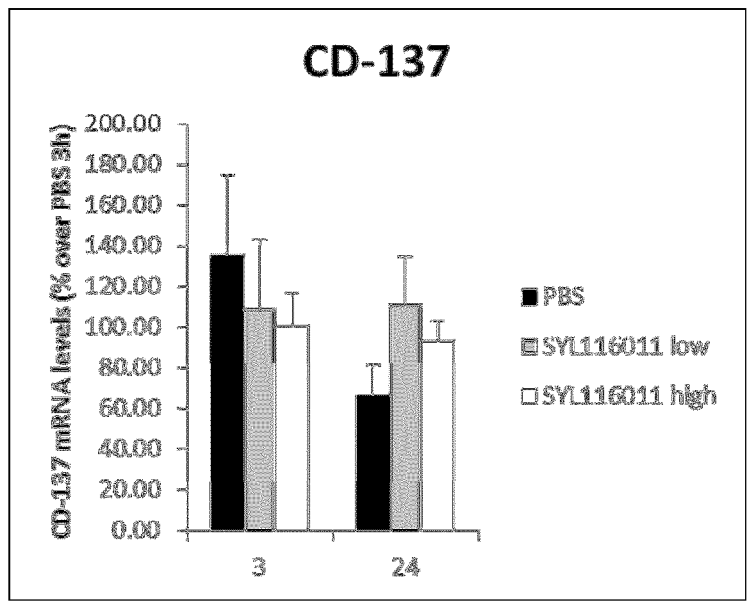
FIGURE 24

```
                          SEQUENCE LISTING

<160> NUMBER OF SEQ ID NOS: 236

<210> SEQ ID NO 1
<211> LENGTH: 19
<212> TYPE: DNA
<213> ORGANISM: Homo sapiens

<400> SEQUENCE: 1
tgatgagcct caacgagca                                                    19

<210> SEQ ID NO 2
<211> LENGTH: 19
<212> TYPE: DNA
<213> ORGANISM: Homo sapiens

<400> SEQUENCE: 2
ggactggatc ggccagagt                                                    19

<210> SEQ ID NO 3
<211> LENGTH: 19
<212> TYPE: DNA
<213> ORGANISM: Homo sapiens

<400> SEQUENCE: 3
ccgaggtgat gagcctcaa                                                    19

<210> SEQ ID NO 4
<211> LENGTH: 19
<212> TYPE: DNA
<213> ORGANISM: Homo sapiens

<400> SEQUENCE: 4
ctgtcctggc gcaagctct                                                    19

<210> SEQ ID NO 5
<211> LENGTH: 19
<212> TYPE: DNA
<213> ORGANISM: Homo sapiens

<400> SEQUENCE: 5
cctgcatcct gcccaacat                                                    19

<210> SEQ ID NO 6
<211> LENGTH: 19
<212> TYPE: DNA
<213> ORGANISM: Homo sapiens

<400> SEQUENCE: 6
gcatcctgcc caacatcga                                                    19

<210> SEQ ID NO 7
<211> LENGTH: 19
<212> TYPE: DNA
<213> ORGANISM: Homo sapiens
```

<400> SEQUENCE: 7
aggtgatgag cctcaacga                    19

<210> SEQ ID NO 8
<211> LENGTH: 19
<212> TYPE: DNA
<213> ORGANISM: Homo sapiens

<400> SEQUENCE: 8
tgtcctggcg caagctcta                    19

<210> SEQ ID NO 9
<211> LENGTH: 19
<212> TYPE: DNA
<213> ORGANISM: Homo sapiens

<400> SEQUENCE: 9
cgccggagcc gccgccgca                    19

<210> SEQ ID NO 10
<211> LENGTH: 19
<212> TYPE: DNA
<213> ORGANISM: Homo sapiens

<400> SEQUENCE: 10
gccgccgccg cagcgggga                    19

<210> SEQ ID NO 11
<211> LENGTH: 19
<212> TYPE: DNA
<213> ORGANISM: Homo sapiens

<400> SEQUENCE: 11
gccgcagcgg ggacgggga                    19

<210> SEQ ID NO 12
<211> LENGTH: 19
<212> TYPE: DNA
<213> ORGANISM: Homo sapiens

<400> SEQUENCE: 12
cgctgtcctg gcgcaagct                    19

<210> SEQ ID NO 13
<211> LENGTH: 19
<212> TYPE: DNA
<213> ORGANISM: Homo sapiens

<400> SEQUENCE: 13
cctggcgcaa gctctactt                    19

<210> SEQ ID NO 14
<211> LENGTH: 19
<212> TYPE: DNA
<213> ORGANISM: Homo sapiens

<400> SEQUENCE: 14
gcgcaagctc tacttgagc                    19

<210> SEQ ID NO 15
<211> LENGTH: 19
<212> TYPE: DNA

```
<213> ORGANISM: Homo sapiens

<400> SEQUENCE: 15
gcccccgagc cgcagcagt                                               19

<210> SEQ ID NO 16
<211> LENGTH: 19
<212> TYPE: DNA
<213> ORGANISM: Homo sapiens

<400> SEQUENCE: 16
ccccgagccg cagcagtcc                                               19

<210> SEQ ID NO 17
<211> LENGTH: 19
<212> TYPE: DNA
<213> ORGANISM: Homo sapiens

<400> SEQUENCE: 17
gccgcagcag tcccgagct                                               19

<210> SEQ ID NO 18
<211> LENGTH: 19
<212> TYPE: DNA
<213> ORGANISM: Homo sapiens

<400> SEQUENCE: 18
ccgcagcagt cccgagctt                                               19

<210> SEQ ID NO 19
<211> LENGTH: 19
<212> TYPE: DNA
<213> ORGANISM: Homo sapiens

<400> SEQUENCE: 19
cgcagcagtc ccgagcttc                                               19

<210> SEQ ID NO 20
<211> LENGTH: 19
<212> TYPE: DNA
<213> ORGANISM: Homo sapiens

<400> SEQUENCE: 20
cccccaagcg gcggcagca                                               19

<210> SEQ ID NO 21
<211> LENGTH: 19
<212> TYPE: DNA
<213> ORGANISM: Homo sapiens

<400> SEQUENCE: 21
ccccaagcgg cggcagcac                                               19

<210> SEQ ID NO 22
<211> LENGTH: 19
<212> TYPE: DNA
<213> ORGANISM: Homo sapiens

<400> SEQUENCE: 22
ggcagcacca ccagcggca                                               19

<210> SEQ ID NO 23
<211> LENGTH: 19
```

```
<212> TYPE: DNA
<213> ORGANISM: Homo sapiens

<400> SEQUENCE: 23
gcccccgggg gccccgcca                                                19

<210> SEQ ID NO 24
<211> LENGTH: 19
<212> TYPE: DNA
<213> ORGANISM: Homo sapiens

<400> SEQUENCE: 24
gccccgccac cgccgccgt                                                19

<210> SEQ ID NO 25
<211> LENGTH: 19
<212> TYPE: DNA
<213> ORGANISM: Homo sapiens

<400> SEQUENCE: 25
ccgccgccgt ccgccgtca                                                19

<210> SEQ ID NO 26
<211> LENGTH: 19
<212> TYPE: DNA
<213> ORGANISM: Homo sapiens

<400> SEQUENCE: 26
ccgccgtccg ccgtcacct                                                19

<210> SEQ ID NO 27
<211> LENGTH: 19
<212> TYPE: DNA
<213> ORGANISM: Homo sapiens

<400> SEQUENCE: 27
cgccgtccgc cgtcaccta                                                19

<210> SEQ ID NO 28
<211> LENGTH: 19
<212> TYPE: DNA
<213> ORGANISM: Homo sapiens

<400> SEQUENCE: 28
gccgtccgcc gtcacctac                                                19

<210> SEQ ID NO 29
<211> LENGTH: 19
<212> TYPE: DNA
<213> ORGANISM: Homo sapiens

<400> SEQUENCE: 29
ccgccgtcac ctacccgga                                                19

<210> SEQ ID NO 30
<211> LENGTH: 19
<212> TYPE: DNA
<213> ORGANISM: Homo sapiens

<400> SEQUENCE: 30
gccgtcacct acccggact                                                19

<210> SEQ ID NO 31
```

<211> LENGTH: 19
<212> TYPE: DNA
<213> ORGANISM: Homo sapiens

<400> SEQUENCE: 31
cacctacccg gactggatc                                                  19

<210> SEQ ID NO 32
<211> LENGTH: 19
<212> TYPE: DNA
<213> ORGANISM: Homo sapiens

<400> SEQUENCE: 32
ccggactgga tcggccaga                                                  19

<210> SEQ ID NO 33
<211> LENGTH: 19
<212> TYPE: DNA
<213> ORGANISM: Homo sapiens

<400> SEQUENCE: 33
gactggatcg gccagagtt                                                  19

<210> SEQ ID NO 34
<211> LENGTH: 19
<212> TYPE: DNA
<213> ORGANISM: Homo sapiens

<400> SEQUENCE: 34
actggatcgg ccagagtta                                                  19

<210> SEQ ID NO 35
<211> LENGTH: 19
<212> TYPE: DNA
<213> ORGANISM: Homo sapiens

<400> SEQUENCE: 35
gccagagtta ctccgaggt                                                  19

<210> SEQ ID NO 36
<211> LENGTH: 19
<212> TYPE: DNA
<213> ORGANISM: Homo sapiens

<400> SEQUENCE: 36
cagagttact ccgaggtga                                                  19

<210> SEQ ID NO 37
<211> LENGTH: 19
<212> TYPE: DNA
<213> ORGANISM: Homo sapiens

<400> SEQUENCE: 37
gcctcaacga gcactccat                                                  19

<210> SEQ ID NO 38
<211> LENGTH: 19
<212> TYPE: DNA
<213> ORGANISM: Homo sapiens

<400> SEQUENCE: 38
tcaacgagca ctccatgca                                                  19

```
<210> SEQ ID NO 39
<211> LENGTH: 19
<212> TYPE: DNA
<213> ORGANISM: Homo sapiens

<400> SEQUENCE: 39
cactccatgc aggcgctgt                                                 19

<210> SEQ ID NO 40
<211> LENGTH: 19
<212> TYPE: DNA
<213> ORGANISM: Homo sapiens

<400> SEQUENCE: 40
cttgagccgc gccaagctt                                                 19

<210> SEQ ID NO 41
<211> LENGTH: 19
<212> TYPE: DNA
<213> ORGANISM: Homo sapiens

<400> SEQUENCE: 41
tgagccgcgc caagcttaa                                                 19

<210> SEQ ID NO 42
<211> LENGTH: 19
<212> TYPE: DNA
<213> ORGANISM: Homo sapiens

<400> SEQUENCE: 42
gagccgcgcc aagcttaaa                                                 19

<210> SEQ ID NO 43
<211> LENGTH: 19
<212> TYPE: DNA
<213> ORGANISM: Homo sapiens

<400> SEQUENCE: 43
cgcgccaagc ttaaagcct                                                 19

<210> SEQ ID NO 44
<211> LENGTH: 19
<212> TYPE: DNA
<213> ORGANISM: Homo sapiens

<400> SEQUENCE: 44
gcgccaagct taaagcctc                                                 19

<210> SEQ ID NO 45
<211> LENGTH: 19
<212> TYPE: DNA
<213> ORGANISM: Homo sapiens

<400> SEQUENCE: 45
cgccaagctt aaagcctcc                                                 19

<210> SEQ ID NO 46
<211> LENGTH: 19
<212> TYPE: DNA
<213> ORGANISM: Homo sapiens

<400> SEQUENCE: 46
gccaagctta aagcctcca                                                 19
```

```
<210> SEQ ID NO 47
<211> LENGTH: 19
<212> TYPE: DNA
<213> ORGANISM: Homo sapiens

<400> SEQUENCE: 47
ccagccggac ctcggctct                                                  19

<210> SEQ ID NO 48
<211> LENGTH: 19
<212> TYPE: DNA
<213> ORGANISM: Homo sapiens

<400> SEQUENCE: 48
gccggacctc ggctctgct                                                  19

<210> SEQ ID NO 49
<211> LENGTH: 19
<212> TYPE: DNA
<213> ORGANISM: Homo sapiens

<400> SEQUENCE: 49
cggacctcgg ctctgctct                                                  19

<210> SEQ ID NO 50
<211> LENGTH: 19
<212> TYPE: DNA
<213> ORGANISM: Homo sapiens

<400> SEQUENCE: 50
cggctctgct ctccggctt                                                  19

<210> SEQ ID NO 51
<211> LENGTH: 19
<212> TYPE: DNA
<213> ORGANISM: Homo sapiens

<400> SEQUENCE: 51
ggctctgctc tccggcttc                                                  19

<210> SEQ ID NO 52
<211> LENGTH: 19
<212> TYPE: DNA
<213> ORGANISM: Homo sapiens

<400> SEQUENCE: 52
cggcttcgcc atggtggca                                                  19

<210> SEQ ID NO 53
<211> LENGTH: 19
<212> TYPE: DNA
<213> ORGANISM: Homo sapiens

<400> SEQUENCE: 53
ggcttcgcca tggtggcaa                                                  19

<210> SEQ ID NO 54
<211> LENGTH: 19
<212> TYPE: DNA
<213> ORGANISM: Homo sapiens

<400> SEQUENCE: 54
gcttcgccat ggtggcaat                                                  19
```

```
<210> SEQ ID NO 55
<211> LENGTH: 19
<212> TYPE: DNA
<213> ORGANISM: Homo sapiens

<400> SEQUENCE: 55
ctggacgctg accacgact                                               19

<210> SEQ ID NO 56
<211> LENGTH: 19
<212> TYPE: DNA
<213> ORGANISM: Homo sapiens

<400> SEQUENCE: 56
cgctgaccac gactaccca                                               19

<210> SEQ ID NO 57
<211> LENGTH: 19
<212> TYPE: DNA
<213> ORGANISM: Homo sapiens

<400> SEQUENCE: 57
cccaccgggg ctgctcatc                                               19

<210> SEQ ID NO 58
<211> LENGTH: 19
<212> TYPE: DNA
<213> ORGANISM: Homo sapiens

<400> SEQUENCE: 58
ccggggctgc tcatcgcct                                               19

<210> SEQ ID NO 59
<211> LENGTH: 19
<212> TYPE: DNA
<213> ORGANISM: Homo sapiens

<400> SEQUENCE: 59
cggggctgct catcgcctt                                               19

<210> SEQ ID NO 60
<211> LENGTH: 19
<212> TYPE: DNA
<213> ORGANISM: Homo sapiens

<400> SEQUENCE: 60
ggggctgctc atcgccttc                                               19

<210> SEQ ID NO 61
<211> LENGTH: 19
<212> TYPE: DNA
<213> ORGANISM: Homo sapiens

<400> SEQUENCE: 61
gggctgctca tcgccttca                                               19

<210> SEQ ID NO 62
<211> LENGTH: 19
<212> TYPE: DNA
<213> ORGANISM: Homo sapiens

<400> SEQUENCE: 62
```

-continued gctgctcatc gccttcagt 19

<210> SEQ ID NO 63
<211> LENGTH: 19
<212> TYPE: DNA
<213> ORGANISM: Homo sapiens

<400> SEQUENCE: 63
gccttcagtg cctgcacca 19

<210> SEQ ID NO 64
<211> LENGTH: 19
<212> TYPE: DNA
<213> ORGANISM: Homo sapiens

<400> SEQUENCE: 64
cctgcaccac agtgctggt 19

<210> SEQ ID NO 65
<211> LENGTH: 19
<212> TYPE: DNA
<213> ORGANISM: Homo sapiens

<400> SEQUENCE: 65
ccacagtgct ggtggctgt 19

<210> SEQ ID NO 66
<211> LENGTH: 19
<212> TYPE: DNA
<213> ORGANISM: Homo sapiens

<400> SEQUENCE: 66
ctggtggctg tgcacctgt 19

<210> SEQ ID NO 67
<211> LENGTH: 19
<212> TYPE: DNA
<213> ORGANISM: Homo sapiens

<400> SEQUENCE: 67
ggtggctgtg cacctgttt 19

<210> SEQ ID NO 68
<211> LENGTH: 19
<212> TYPE: DNA
<213> ORGANISM: Homo sapiens

<400> SEQUENCE: 68
gtgcacctgt ttgcgctca 19

<210> SEQ ID NO 69
<211> LENGTH: 19
<212> TYPE: DNA
<213> ORGANISM: Homo sapiens

<400> SEQUENCE: 69
cacctgtttg cgctcatga 19

<210> SEQ ID NO 70
<211> LENGTH: 19
<212> TYPE: DNA
<213> ORGANISM: Homo sapiens

<400> SEQUENCE: 70
ctgtttgcgc tcatgatca                                                19

<210> SEQ ID NO 71
<211> LENGTH: 19
<212> TYPE: DNA
<213> ORGANISM: Homo sapiens

<400> SEQUENCE: 71
gcgctcatga tcagcacct                                                19

<210> SEQ ID NO 72
<211> LENGTH: 19
<212> TYPE: DNA
<213> ORGANISM: Homo sapiens

<400> SEQUENCE: 72
gcacctgcat cctgcccaa                                                19

<210> SEQ ID NO 73
<211> LENGTH: 19
<212> TYPE: DNA
<213> ORGANISM: Homo sapiens

<400> SEQUENCE: 73
cccaacatcg aggcggtga                                                19

<210> SEQ ID NO 74
<211> LENGTH: 19
<212> TYPE: DNA
<213> ORGANISM: Homo sapiens

<400> SEQUENCE: 74
gcggtgagca acgtgcaca                                                19

<210> SEQ ID NO 75
<211> LENGTH: 19
<212> TYPE: DNA
<213> ORGANISM: Homo sapiens

<400> SEQUENCE: 75
cggtgagcaa cgtgcacaa                                                19

<210> SEQ ID NO 76
<211> LENGTH: 19
<212> TYPE: DNA
<213> ORGANISM: Homo sapiens

<400> SEQUENCE: 76
ggtgagcaac gtgcacaat                                                19

<210> SEQ ID NO 77
<211> LENGTH: 19
<212> TYPE: DNA
<213> ORGANISM: Homo sapiens

<400> SEQUENCE: 77
tgagcaacgt gcacaatct                                                19

<210> SEQ ID NO 78
<211> LENGTH: 19
<212> TYPE: DNA
<213> ORGANISM: Homo sapiens

<400> SEQUENCE: 78
gcaacgtgca caatctcaa                                                19

<210> SEQ ID NO 79
<211> LENGTH: 19
<212> TYPE: DNA
<213> ORGANISM: Homo sapiens

<400> SEQUENCE: 79
cacaatctca actcggtca                                                19

<210> SEQ ID NO 80
<211> LENGTH: 19
<212> TYPE: DNA
<213> ORGANISM: Homo sapiens

<400> SEQUENCE: 80
acaatctcaa ctcggtcaa                                                19

<210> SEQ ID NO 81
<211> LENGTH: 19
<212> TYPE: DNA
<213> ORGANISM: Homo sapiens

<400> SEQUENCE: 81
ctcaactcgg tcaaggagt                                                19

<210> SEQ ID NO 82
<211> LENGTH: 19
<212> TYPE: DNA
<213> ORGANISM: Homo sapiens

<400> SEQUENCE: 82
cggtcaagga gtccccca                                                 19

<210> SEQ ID NO 83
<211> LENGTH: 19
<212> TYPE: DNA
<213> ORGANISM: Homo sapiens

<400> SEQUENCE: 83
ggtcaaggag tcccccat                                                 19

<210> SEQ ID NO 84
<211> LENGTH: 19
<212> TYPE: DNA
<213> ORGANISM: Homo sapiens

<400> SEQUENCE: 84
ttgagattgt gcacgttgc                                                19

<210> SEQ ID NO 85
<211> LENGTH: 19
<212> TYPE: DNA
<213> ORGANISM: Homo sapiens

<400> SEQUENCE: 85
attgtgcacg ttgctcacc                                                19

<210> SEQ ID NO 86
<211> LENGTH: 19
<212> TYPE: DNA
<213> ORGANISM: Homo sapiens -continued

```
<400> SEQUENCE: 86
atcacctcgg agtaactct                                                19

<210> SEQ ID NO 87
<211> LENGTH: 19
<212> TYPE: DNA
<213> ORGANISM: Homo sapiens

<400> SEQUENCE: 87
atggagtgct cgttgaggc                                                19

<210> SEQ ID NO 88
<211> LENGTH: 19
<212> TYPE: DNA
<213> ORGANISM: Homo sapiens

<400> SEQUENCE: 88
atcatgagcg caaacaggt                                                19

<210> SEQ ID NO 89
<211> LENGTH: 19
<212> TYPE: DNA
<213> ORGANISM: Homo sapiens

<400> SEQUENCE: 89
atgttgggca ggatgcagg                                                19

<210> SEQ ID NO 90
<211> LENGTH: 19
<212> TYPE: DNA
<213> ORGANISM: Homo sapiens

<400> SEQUENCE: 90
aagtagagct tgcgccagg                                                19

<210> SEQ ID NO 91
<211> LENGTH: 19
<212> TYPE: DNA
<213> ORGANISM: Homo sapiens

<400> SEQUENCE: 91
ctcatcacct cggagtaac                                                19

<210> SEQ ID NO 92
<211> LENGTH: 19
<212> TYPE: DNA
<213> ORGANISM: Homo sapiens

<400> SEQUENCE: 92
agattgtgca cgttgctca                                                19

<210> SEQ ID NO 93
<211> LENGTH: 19
<212> TYPE: DNA
<213> ORGANISM: Homo sapiens

<400> SEQUENCE: 93
agtaactctg gccgatcca                                                19

<210> SEQ ID NO 94
<211> LENGTH: 19
<212> TYPE: DNA
```

<213> ORGANISM: Homo sapiens

<400> SEQUENCE: 94
atgcgctcat gggggact                              19

<210> SEQ ID NO 95
<211> LENGTH: 19
<212> TYPE: DNA
<213> ORGANISM: Homo sapiens

<400> SEQUENCE: 95
gcaacgtgca caatctcaa                             19

<210> SEQ ID NO 96
<211> LENGTH: 19
<212> TYPE: DNA
<213> ORGANISM: Homo sapiens

<400> SEQUENCE: 96
cggtgagcaa cgtgcacaa                             19

<210> SEQ ID NO 97
<211> LENGTH: 19
<212> TYPE: DNA
<213> ORGANISM: Homo sapiens

<400> SEQUENCE: 97
gcaacgtgca caatctcaa                             19

<210> SEQ ID NO 98
<211> LENGTH: 19
<212> TYPE: DNA
<213> ORGANISM: Homo sapiens

<400> SEQUENCE: 98
actggatcgg ccagagtta                             19

<210> SEQ ID NO 99
<211> LENGTH: 19
<212> TYPE: DNA
<213> ORGANISM: Homo sapiens

<400> SEQUENCE: 99
agagttactc cgaggtgat                             19

<210> SEQ ID NO 100
<211> LENGTH: 19
<212> TYPE: DNA
<213> ORGANISM: Homo sapiens

<400> SEQUENCE: 100
gcctcaacga gcactccat                             19

<210> SEQ ID NO 101
<211> LENGTH: 19
<212> TYPE: DNA
<213> ORGANISM: Homo sapiens

<400> SEQUENCE: 101
ggcgcaagct ctacttgag                             19

<210> SEQ ID NO 102
<211> LENGTH: 19

<212> TYPE: DNA
<213> ORGANISM: Homo sapiens

<400> SEQUENCE: 102
ggcttcgcca tggtggcaa                                              19

<210> SEQ ID NO 103
<211> LENGTH: 19
<212> TYPE: DNA
<213> ORGANISM: Homo sapiens

<400> SEQUENCE: 103
gcttcgccat ggtggcaat                                              19

<210> SEQ ID NO 104
<211> LENGTH: 19
<212> TYPE: DNA
<213> ORGANISM: Homo sapiens

<400> SEQUENCE: 104
tggacgctga ccacgacta                                              19

<210> SEQ ID NO 105
<211> LENGTH: 19
<212> TYPE: DNA
<213> ORGANISM: Homo sapiens

<400> SEQUENCE: 105
cggggctgct catcgcctt                                              19

<210> SEQ ID NO 106
<211> LENGTH: 19
<212> TYPE: DNA
<213> ORGANISM: Homo sapiens

<400> SEQUENCE: 106
gcacctgcat cctgcccaa                                              19

<210> SEQ ID NO 107
<211> LENGTH: 19
<212> TYPE: DNA
<213> ORGANISM: Homo sapiens

<400> SEQUENCE: 107
acatcgaggc ggtgagcaa                                              19

<210> SEQ ID NO 108
<211> LENGTH: 19
<212> TYPE: DNA
<213> ORGANISM: Homo sapiens

<400> SEQUENCE: 108
cggtgagcaa cgtgcacaa                                              19

<210> SEQ ID NO 109
<211> LENGTH: 19
<212> TYPE: DNA
<213> ORGANISM: Homo sapiens

<400> SEQUENCE: 109
ggtgagcaac gtgcacaat                                              19

<210> SEQ ID NO 110

```
<211> LENGTH: 19
<212> TYPE: DNA
<213> ORGANISM: Homo sapiens

<400> SEQUENCE: 110
gcaacgtgca caatctcaa                                                  19

<210> SEQ ID NO 111
<211> LENGTH: 19
<212> TYPE: DNA
<213> ORGANISM: Homo sapiens

<400> SEQUENCE: 111
acaatctcaa ctcggtcaa                                                  19

<210> SEQ ID NO 112
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 112
ugaugagccu caacgagca                                                  19

<210> SEQ ID NO 113
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 113
ggacuggauc ggccagagu                                                  19

<210> SEQ ID NO 114
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 114
ccgaggugau gagccucaa                                                  19

<210> SEQ ID NO 115
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 115
cuguccuggc gcaagcucu                                                  19

<210> SEQ ID NO 116
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 116
ccugcauccu gcccaacau                                                  19
```

```
<210> SEQ ID NO 117
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 117
gcauccugcc caacaucga                                              19

<210> SEQ ID NO 118
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 118
aggugaugag ccucaacga                                              19

<210> SEQ ID NO 119
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 119
uguccuggcg caagcucua                                              19

<210> SEQ ID NO 120
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 120
cgccggagcc gccgccgca                                              19

<210> SEQ ID NO 121
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 121
gccgccgccg cagcgggga                                              19

<210> SEQ ID NO 122
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 122
gccgcagcgg ggacgggga                                              19

<210> SEQ ID NO 123
<211> LENGTH: 19
<212> TYPE: RNA
<213> ORGANISM: Artificial Sequence
<220> FEATURE:
<223> OTHER INFORMATION: ORAI1 siRNA
```

```
<400> SEQUENCE: 123
cgcuguccug gcgcaagcu                                                  19

<210> SEQ ID NO 124
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 124
ccuggcgcaa gcucuacuu                                                  19

<210> SEQ ID NO 125
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 125
gcgcaagcuc uacuugagc                                                  19

<210> SEQ ID NO 126
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 126
gcccccgagc cgcagcagu                                                  19

<210> SEQ ID NO 127
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 127
ccccgagccg cagcagucc                                                  19

<210> SEQ ID NO 128
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 128
gccgcagcag ucccgagcu                                                  19

<210> SEQ ID NO 129
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 129
ccgcagcagu cccgagcuu                                                  19

<210> SEQ ID NO 130
<211> LENGTH: 19
```

-continued

<212> TYPE: RNA
<213> ORGANISM: Artificial Sequence
<220> FEATURE:
<223> OTHER INFORMATION: ORAI1 siRNA

<400> SEQUENCE: 130
cgcagcaguc ccgagcuuc                                                   19

<210> SEQ ID NO 131
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 131
cccccaagcg gcggcagca                                                   19

<210> SEQ ID NO 132
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 132
ccccaagcgg cggcagcac                                                   19

<210> SEQ ID NO 133
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 133
ggcagcacca ccagcggca                                                   19

<210> SEQ ID NO 134
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 134
gcccccgggg gccccgcca                                                   19

<210> SEQ ID NO 135
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 135
gccccgccac cgccgccgu                                                   19

<210> SEQ ID NO 136
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 136
ccgccgccgu ccgccguca                                         19

<210> SEQ ID NO 137
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 137
ccgccguccg ccgucaccu                                         19

<210> SEQ ID NO 138
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 138
cgccguccgc cgucaccua                                         19

<210> SEQ ID NO 139
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 139
gccguccgcc gucaccuac                                         19

<210> SEQ ID NO 140
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 140
ccgccgucac cuacccgga                                         19

<210> SEQ ID NO 141
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 141
gccgucaccu acccggacu                                         19

<210> SEQ ID NO 142
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 142
caccuacccg gacuggauc                                         19

<210> SEQ ID NO 143
<211> LENGTH: 19
<212> TYPE: RNA
<213> ORGANISM: Artificial Sequence

```
<220> FEATURE:
<223> OTHER INFORMATION: ORAI1 siRNA

<400> SEQUENCE: 143
ccggacugga ucggccaga                                              19

<210> SEQ ID NO 144
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 144
gacuggaucg gccagaguu                                              19

<210> SEQ ID NO 145
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 145
acuggaucgg ccagaguua                                              19

<210> SEQ ID NO 146
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 146
gccagaguua cuccgaggu                                              19

<210> SEQ ID NO 147
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 147
cagaguuacu ccgagguga                                              19

<210> SEQ ID NO 148
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 148
gccucaacga gcacuccau                                              19

<210> SEQ ID NO 149
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 149
ucaacgagca cuccaugca                                              19
```

<210> SEQ ID NO 150
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 150
cacuccaugc aggcgcugu                                              19

<210> SEQ ID NO 151
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 151
cuugagccgc gccaagcuu                                              19

<210> SEQ ID NO 152
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 152
ugagccgcgc caagcuuaa                                              19

<210> SEQ ID NO 153
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 153
gagccgcgcc aagcuuaaa                                              19

<210> SEQ ID NO 154
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 154
cgcgccaagc uuaaagccu                                              19

<210> SEQ ID NO 155
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 155
gcgccaagcu uaaagccuc                                              19

<210> SEQ ID NO 156
<211> LENGTH: 19
<212> TYPE: RNA
<213> ORGANISM: Artificial Sequence
<220> FEATURE:
<223> OTHER INFORMATION: ORAI1 siRNA

```
<400> SEQUENCE: 156
cgccaagcuu aaagccucc                                                   19

<210> SEQ ID NO 157
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 157
gccaagcuua aagccucca                                                   19

<210> SEQ ID NO 158
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 158
ccagccggac cucggcucu                                                   19

<210> SEQ ID NO 159
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 159
gccggaccuc ggcucugcu                                                   19

<210> SEQ ID NO 160
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 160
cggaccucgg cucugcucu                                                   19

<210> SEQ ID NO 161
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 161
cggcucugcu cuccggcuu                                                   19

<210> SEQ ID NO 162
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 162
ggcucugcuc uccggcuuc                                                   19

<210> SEQ ID NO 163
```

```
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 163
cggcuucgcc augguggca                                                      19

<210> SEQ ID NO 164
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 164
ggcuucgcca ugguggcaa                                                      19

<210> SEQ ID NO 165
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 165
gcuucgccau gguggcaau                                                      19

<210> SEQ ID NO 166
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 166
cuggacgcug accacgacu                                                      19

<210> SEQ ID NO 167
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 167
cgcugaccac gacuaccca                                                      19

<210> SEQ ID NO 168
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 168
cccaccgggg cugcucauc                                                      19

<210> SEQ ID NO 169
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 169
```

```
ccggggcugc ucaucgccu                                           19
```

<210> SEQ ID NO 170
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 170

```
cggggcugcu caucgccuu                                           19
```

<210> SEQ ID NO 171
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 171

```
ggggcugcuc aucgccuuc                                           19
```

<210> SEQ ID NO 172
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 172

```
gggcugcuca ucgccuuca                                           19
```

<210> SEQ ID NO 173
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 173

```
gcugcucauc gccuucagu                                           19
```

<210> SEQ ID NO 174
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 174

```
gccuucagug ccugcacca                                           19
```

<210> SEQ ID NO 175
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 175

```
ccugcaccac agugcuggu                                           19
```

<210> SEQ ID NO 176
<211> LENGTH: 19
<212> TYPE: RNA

```
<213> ORGANISM: Artificial Sequence
<220> FEATURE:
<223> OTHER INFORMATION: ORAI1 siRNA

<400> SEQUENCE: 176
ccacagugcu gguggcugu                                                19

<210> SEQ ID NO 177
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 177
cugguggcug ugcaccugu                                                19

<210> SEQ ID NO 178
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 178
gguggcugug caccuguuu                                                19

<210> SEQ ID NO 179
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 179
gugcaccugu uugcgcuca                                                19

<210> SEQ ID NO 180
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 180
caccuguuug cgcucauga                                                19

<210> SEQ ID NO 181
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 181
cuguuugcgc ucaugauca                                                19

<210> SEQ ID NO 182
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 182
gcgcucauga ucagcaccu                                                19
```

```
<210> SEQ ID NO 183
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 183
gcaccugcau ccugcccaa                                               19

<210> SEQ ID NO 184
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 184
cccaacaucg aggcgguga                                               19

<210> SEQ ID NO 185
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 185
gcggugagca acgugcaca                                               19

<210> SEQ ID NO 186
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 186
cggugagcaa cgugcacaa                                               19

<210> SEQ ID NO 187
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 187
ggugagcaac gugcacaau                                               19

<210> SEQ ID NO 188
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 188
ugagcaacgu gcacaaucu                                               19

<210> SEQ ID NO 189
<211> LENGTH: 19
<212> TYPE: RNA
<213> ORGANISM: Artificial Sequence
<220> FEATURE:
```

<223> OTHER INFORMATION: ORAI1 siRNA

<400> SEQUENCE: 189
gcaacgugca caaucucaa                                                    19

<210> SEQ ID NO 190
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 190
cacaaucuca acucgguca                                                    19

<210> SEQ ID NO 191
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 191
acaaucucaa cucggucaa                                                    19

<210> SEQ ID NO 192
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 192
cucaacucgg ucaaggagu                                                    19

<210> SEQ ID NO 193
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 193
cggucaagga gucccccca                                                    19

<210> SEQ ID NO 194
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 194
ggucaaggag uccccccau                                                    19

<210> SEQ ID NO 195
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 195
uugagauugu gcacguugc                                                    19

```
<210> SEQ ID NO 196
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 196
auugugcacg uugcucacc                                                   19

<210> SEQ ID NO 197
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 197
aucaccucgg aguaacucu                                                   19

<210> SEQ ID NO 198
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 198
auggagugcu cguugaggc                                                   19

<210> SEQ ID NO 199
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 199
aucaugagcg caaacaggu                                                   19

<210> SEQ ID NO 200
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 200
auguugggca ggaugcagg                                                   19

<210> SEQ ID NO 201
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 201
aaguagagcu ugcgccagg                                                   19

<210> SEQ ID NO 202
<211> LENGTH: 19
<212> TYPE: RNA
<213> ORGANISM: Artificial Sequence
<220> FEATURE:
<223> OTHER INFORMATION: ORAI1 siRNA
```

```
<400> SEQUENCE: 202
cucaucaccu cggaguaac                                              19

<210> SEQ ID NO 203
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 203
agauugugca cguugcuca                                              19

<210> SEQ ID NO 204
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 204
aguaacucug gccgaucca                                              19

<210> SEQ ID NO 205
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 205
augcgcucau gggggacu                                               19

<210> SEQ ID NO 206
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 206
gcaacgugca caaucucaa                                              19

<210> SEQ ID NO 207
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 207
cggugagcaa cgugcacaa                                              19

<210> SEQ ID NO 208
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 208
gcaacgugca caaucucaa                                              19

<210> SEQ ID NO 209
<211> LENGTH: 19
```

```
<212> TYPE: RNA
<213> ORGANISM: Artificial Sequence
<220> FEATURE:
<223> OTHER INFORMATION: ORAI1 siRNA

<400> SEQUENCE: 209
acuggaucgg ccagaguua                                              19

<210> SEQ ID NO 210
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 210
agaguuacuc cgaggugau                                              19

<210> SEQ ID NO 211
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 211
gccucaacga gcacuccau                                              19

<210> SEQ ID NO 212
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 212
ggcgcaagcu cuacuugag                                              19

<210> SEQ ID NO 213
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 213
ggcuucgcca ugguggcaa                                              19

<210> SEQ ID NO 214
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 214
gcuucgccau gguggcaau                                              19

<210> SEQ ID NO 215
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 215
```
uggacgcuga ccacgacua                                                    19

<210> SEQ ID NO 216
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 216
cggggcugcu caucgccuu                                                    19

<210> SEQ ID NO 217
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 217
gcaccugcau ccugcccaa                                                    19

<210> SEQ ID NO 218
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 218
acaucgaggc ggugagcaa                                                    19

<210> SEQ ID NO 219
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 219
cggugagcaa cgugcacaa                                                    19

<210> SEQ ID NO 220
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 220
ggugagcaac gugcacaau                                                    19

<210> SEQ ID NO 221
<211> LENGTH: 19
<212> TYPE: RNA
<213> ORGANISM: Artificial Sequence
<220> FEATURE:
<223> OTHER INFORMATION: ORAI1 siRNA

<400> SEQUENCE: 221
gcaacgugca caaucucaa                                                    19

<210> SEQ ID NO 222
<211> LENGTH: 19
<212> TYPE: RNA
<213> ORGANISM: Artificial Sequence

```
<220> FEATURE:
<223> OTHER INFORMATION: ORAI1 siRNA

<400> SEQUENCE: 222
acaaucucaa cucggucaa                                              19

<210> SEQ ID NO 223
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (12)..(13)
<223> OTHER INFORMATION: a = 2'OMe adenine
<220> FEATURE:
<221> NAME/KEY: misc_feature
<222> LOCATION: (16)..(16)
<223> OTHER INFORMATION: a = 2'OMe adenine
<220> FEATURE:
<221> NAME/KEY: misc_feature
<222> LOCATION: (19)..(19)
<223> OTHER INFORMATION: a = 2'OMe adenine

<400> SEQUENCE: 223
ugaugagccu caacgagca                                              19

<210> SEQ ID NO 224
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (12)..(13)
<223> OTHER INFORMATION: a= 2'OMe adenine
<220> FEATURE:
<221> NAME/KEY: misc_feature
<222> LOCATION: (16)..(16)
<223> OTHER INFORMATION: a= 2'OMe adenine
<220> FEATURE:
<221> NAME/KEY: misc_feature
<222> LOCATION: (19)..(19)
<223> OTHER INFORMATION: a= 2'OMe adenine

<400> SEQUENCE: 224
ugaugagccu caacgagca                                              19

<210> SEQ ID NO 225
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(2)
<223> OTHER INFORMATION: phosphotioate bond
<220> FEATURE:
<221> NAME/KEY: misc_feature
<222> LOCATION: (12)..(13)
<223> OTHER INFORMATION: a= 2'OMe adenine
<220> FEATURE:
<221> NAME/KEY: misc_feature
<222> LOCATION: (16)..(16)
<223> OTHER INFORMATION: a= 2'OMe adenine
<220> FEATURE:
<221> NAME/KEY: misc_feature
<222> LOCATION: (18)..(19)
<223> OTHER INFORMATION: phosphotioate bond
<220> FEATURE:
```

```
<221> NAME/KEY: misc_feature
<222> LOCATION: (19)..(19)
<223> OTHER INFORMATION: a= 2'OMe adenine

<400> SEQUENCE: 225
ugaugagccu caacgagca                                                  19

<210> SEQ ID NO 226
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(2)
<223> OTHER INFORMATION: phosphotioate bond
<220> FEATURE:
<221> NAME/KEY: misc_feature
<222> LOCATION: (12)..(13)
<223> OTHER INFORMATION: a= 2'OMe adenine
<220> FEATURE:
<221> NAME/KEY: misc_feature
<222> LOCATION: (16)..(16)
<223> OTHER INFORMATION: a= 2'OMe adenine
<220> FEATURE:
<221> NAME/KEY: misc_feature
<222> LOCATION: (18)..(19)
<223> OTHER INFORMATION: phosphotioate bond
<220> FEATURE:
<221> NAME/KEY: misc_feature
<222> LOCATION: (19)..(19)
<223> OTHER INFORMATION: a= 2'OMe adenine

<400> SEQUENCE: 226
ugaugagccu caacgagca                                                  19

<210> SEQ ID NO 227
<211> LENGTH: 21
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(2)
<223> OTHER INFORMATION: phosphotioate bond
<220> FEATURE:
<221> NAME/KEY: misc_feature
<222> LOCATION: (16)..(16)
<223> OTHER INFORMATION: a= 2'OMe adenine
<220> FEATURE:
<221> NAME/KEY: misc_feature
<222> LOCATION: (18)..(19)
<223> OTHER INFORMATION: phosphotioate bond

<400> SEQUENCE: 227
ugaugagccu caacmgagcm a                                               21

<210> SEQ ID NO 228
<211> LENGTH: 19
<212> TYPE: DNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(1)
<223> OTHER INFORMATION: T= deoxythymidine
<220> FEATURE:
<221> NAME/KEY: misc_feature
<222> LOCATION: (4)..(4)
<223> OTHER INFORMATION: T= deoxythymidine
```

<400> SEQUENCE: 228
tgatgagccu caacgagca                                                19

<210> SEQ ID NO 229
<211> LENGTH: 19
<212> TYPE: DNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(1)
<223> OTHER INFORMATION: T= deoxythymidine
<220> FEATURE:
<221> NAME/KEY: misc_feature
<222> LOCATION: (4)..(4)
<223> OTHER INFORMATION: T= deoxythymidine

<400> SEQUENCE: 229
tgatgagccu caacgagca                                                19

<210> SEQ ID NO 230
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(2)
<223> OTHER INFORMATION: phosphothioate bond
<220> FEATURE:
<221> NAME/KEY: misc_feature
<222> LOCATION: (18)..(19)
<223> OTHER INFORMATION: phosphothioate bond

<400> SEQUENCE: 230
ugcucguuga ggcucauca                                                19

<210> SEQ ID NO 231
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(2)
<223> OTHER INFORMATION: phosphothioate bond
<220> FEATURE:
<221> NAME/KEY: misc_feature
<222> LOCATION: (18)..(19)
<223> OTHER INFORMATION: phosphothioate bond

<400> SEQUENCE: 231
ugcucguuga ggcucauca                                                19

<210> SEQ ID NO 232
<211> LENGTH: 20
<212> TYPE: DNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(1)
<223> OTHER INFORMATION: T= deoxythymidine
<220> FEATURE:
<221> NAME/KEY: misc_feature
<222> LOCATION: (4)..(4)

```
<223> OTHER INFORMATION: T= deoxythymidine
<220> FEATURE:
<221> NAME/KEY: misc_feature
<222> LOCATION: (7)..(7)
<223> OTHER INFORMATION: T= deoxythymidine

<400> SEQUENCE: 232
tgcdtcgtug aggcucauca                                              20

<210> SEQ ID NO 233
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(1)
<223> OTHER INFORMATION: u = 2'OMe uracil

<400> SEQUENCE: 233
ugaugagccu caacgagca                                               19

<210> SEQ ID NO 234
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(1)
<223> OTHER INFORMATION: u = 2'FU

<400> SEQUENCE: 234
ugcucguuga ggcucauca                                               19

<210> SEQ ID NO 235
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(1)
<223> OTHER INFORMATION: u = 2'OMe uracil

<400> SEQUENCE: 235
ugaugagccu caacgagca                                               19

<210> SEQ ID NO 236
<211> LENGTH: 19
<212> TYPE: RNA
<213> ORGANISM: Artificial Sequence
<220> FEATURE:
<223> OTHER INFORMATION: ORAI1 siRNA
<220> FEATURE:
<221> NAME/KEY: misc_feature
<222> LOCATION: (1)..(2)
<223> OTHER INFORMATION: phosphothioate bond

<400> SEQUENCE: 236
ugcucguuga ggcucauca                                               19
```

SIRNA AND THEIR USE IN METHODS AND COMPOSITIONS FOR INHIBITING THE EXPRESSION OF THE ORAI1 GENE

FIELD OF THE INVENTION

The present invention relates to the field of siRNA products and their use in methods and compositions for the treatment and/or prevention of eye conditions, and more particularly for the treatment and/or prevention of eye conditions such as conjunctivitis and/or ocular allergy, related to high levels of expression and or activity of ORAI1.

BACKGROUND OF THE INVENTION

RNA interference (RNAi) is a naturally occurring post-transcriptional regulatory mechanism present in most eukaryotic cells that uses small double stranded RNA (dsRNA) molecules to direct homology-dependent gene silencing. Its discovery by Fire and Mello in the worm *C. elegans* {Fire, 1998} was awarded the Nobel Prize in 2006. Shortly after its first description, RNAi was also shown to occur in mammalian cells, not through long dsRNAs but by means of double-stranded small interfering RNAs (siRNAs) 21 nucleotides long {Elbashir, 2001}.

The process of RNA interference is thought to be an evolutionarily-conserved cellular defence mechanism used to prevent the expression of foreign genes and is commonly shared by diverse phyla and flora, where it is called post-transcriptional gene silencing. Since the discovery of the RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins, 2005} and its activity leads to the processing of the long double stranded RNAs into 21-24 nucleotide double stranded siRNAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir, 2001} upon adenosine-triphosphate (ATP)-dependent unwinding of the double-stranded siRNA molecule through an RNA helicase activity {Nykanen, 2001}. The catalytic activity of RISC, which leads to mRNA degradation, is mediated by the endonuclease Argonaute 2 (AGO2) {Liu, 2004; Song, 2004}. AGO2 belongs to the highly conserved Argonaute family of proteins. Argonaute proteins are ~100 KDa highly basic proteins that contain two common domains, namely PIWI and PAZ domains {Cerutti, 2000}. The PIWI domain is crucial for the interaction with Dicer and contains the nuclease activity responsible for the cleavage of mRNAs {Song, 2004}. AGO2 uses one strand of the siRNA duplex as a guide to find messenger RNAs containing complementary sequences and cleaves the phosphodiester backbone between bases 10 and 11 relative to the guide strand's 5' end {Elbashir, 2001}. An important step during the activation of RISC is the cleavage of the sense or passenger strand by AGO2, removing this strand from the complex {Rand, 2005}. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule {Ma, 2005; Doench 2004; Lewis, 2003}. Once the mRNA has been cleaved, due to the presence of unprotected RNA ends in the fragments the mRNA is further cleaved and degraded by intracellular nucleases and will no longer be translated into proteins {Orban, 2005} while RISC will be recycled for subsequent rounds {Hutvagner, 2002}. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA. RNAi has been applied in biomedical research such as treatment for HIV, viral hepatitis, cardiovascular and cerebrovascular diseases, metabolic disease, neurodegenerative disorders and cancer {Angaji S A et al 2010}.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies, algorithms and/or improvements have been published since then. siRNA selection approaches have become more sophisticated as mechanistic details have emerged, in addition further analysis of existing and new data can provide additional insights into further refinement of these approaches {Walton S P et al 2010}. Alternatively, several recent studies reported the design and analysis of novel RNAi-triggering structures distinct from the classical 19+2 siRNA structure and which do not conform to the key features of classical siRNA in terms of overhang, length, or symmetry, discussing the flexibility of the RNAi machinery in mammalian cells {Chang C I et al 2011}.

Also, a lot of effort has been put into enhancing siRNA stability as this is perceived as one of the main obstacles for therapy based on siRNA, given the ubiquitous nature of RNAses in biological fluids. Another inherent problem of siRNA molecules is their immunogenicity, whereby siRNAs have been found to induce unspecific activation of the innate immune system. The knockdown of unintended genes (mRNAs) is a well-known side effect of siRNA-mediated gene silencing. It is caused as a result of partial complementarity between the siRNA and mRNAs other than the intended target and causes off-target effects (OTEs) from genes having sequence complementarity to either siRNA strand. One of the main strategies followed for stability enhancement and OTE reduction has been the use of modified nucleotides such as 2'-O-methyl nucleotides, 2'-amino nucleotides, or nucleotides containing 2'-O or 4'-C methylene bridges. Also, the modification of the ribonucleotide backbone connecting adjacent nucleotides has been described, mainly by the introduction of phosphorothioate modified nucleotides. It seems that enhanced stability and/or reduction of immunogenicity are often inversely proportional to efficacy {Parrish, 2000}, and only a certain number, positions and/or combinations of modified nucleotides may result in a stable and non-immunogenic silencing compound. As this is an important hurdle for siRNA-based treatments, different studies have been published which describe certain modification patterns showing good results, examples of such include EP1527176, WO2008/050329, WO2008/104978 or WO2009/044392, although many more may be found in the literature {Sanghvi Y S. 2011; Deleavey et al 2012}.

Allergic diseases are characterized by an overreaction of the human immune system to a foreign protein substance ("allergen") that is eaten, breathed into the lungs, injected or touched. Allergies have a genetic component. If only one parent has allergies of any type, chances are 1 in 3 that each child will have an allergy. If both parents have allergies, it is much more likely (7 in 10) that their children will have allergies. There are no cures for allergies; however they can be managed with proper prevention and treatment.

About 30% of people worldwide suffer from allergic symptoms and 40-80% of them have symptoms in the eyes {Key B. 2001}. Allergic diseases affecting the eyes or ocular allergies constitute a heterogenic group of diseases with a very broad spectrum of clinical manifestations. An ocular allergy usually occurs when the conjunctiva (membrane covering the eye and the lining of the eyelid) reacts to an allergen. An ocular allergy can happen independently or in conjunction with other allergy symptoms (such as rhinitis or asthma).

Basic and clinical research has provided a better understanding of the cells, mediators, and immunologic events which occur in ocular allergy. The eye, particularly the conjunctiva, has a relatively large number of mast cells. When allergens are present they can bind to immunoglobulin, IgE, in the FcεRI receptors on the surface of these mast cells and trigger their activation and release of mediators of allergy (a process known as degranulation). Degranulation releases mast cell components, including histamine, prostaglandins, tryptase and leukotrienes, into the environment outside the mast cell. Through a variety of mechanisms these components produce the signs and symptoms of the ocular allergy. The activation of the mast cells of the allergic inflammation is frequently designated as an acute phase response or early phase of the ocular allergy. The acute phase response can progress to a late phase response characterized by recruitment of inflammatory cells to the site of the allergic inflammation, for example as an influx of eosinophils and neutrophils into the conjunctiva.

Ocular allergy represents one of the most common conditions encountered by allergists and ophthalmologists. Ocular allergy is usually associated with the following symptoms and signs: conjunctivitis, blepharitis, blepharoconjunctivitis or keratoconjunctivitis. The eye becomes red, itchy and there occurs lacrimation and slight discharge. Severe cases may also show eye burning sensation, pain and photophobia.

Allergic diseases affecting the eyes include mild forms such as seasonal allergic conjunctivitis (SAC) and perennial allergic conjunctivitis (PAC); and more severe manifestations such as vernal keratoconjunctivitis (VKC); atopic keratoconjunctivitis (AKC) and giant papillary conjunctivitis (GPC). The latter ones can be associated with complications such as corneal damage and may cause vision loss. SAC and PAC are commonly IgE-mast cell mediated hypersensitivity reaction to external allergens; whereas AKC and VKC are characterized by chronic inflammation involving several immune cell types. SAC and PAC allergens, with the help of antigen presenting cells (APCs), trigger a Th2-predominant immune response that induces B cells to release IgE. Activation of the allergic response usually involves infiltration and degranulation of mast cells.

SAC is the most common allergic disease in the eye, usually caused by allergens like airborne pollen, dust, and animal dander. The signs and symptoms usually occur during the spring and summer, and generally abate during the winter months. Itching, redness and swelling of the conjunctiva are the most characteristic symptoms, but also tearing, burning sensation, and photophobia. In most cases, SAC is not serious. However, it may be very disturbing to patients because it can affect their quality of life and can have significant socioeconomic impact {Kari O. and Saari K M 2010}.

PAC is the second most common allergic disease in the eye, usually caused by animals and mites. The symptoms and signs are much the same as in SAC, the difference is the specific allergens to which the patient is allergic and that PAC can occur throughout the year with exposure to perennial allergens. PAC affects all age groups but mostly young and middle-aged people of both sexes. In addition, PAC is often connected to dry eye syndrome.

SAC and PAC are the most common forms of ocular allergies. Estimates vary, but these types of allergy are said to affect at least 15-20% of the general population. SAC and PAC are often underdiagnosed and consequently undertreated. In SAC and PAC allergen induced local release of IgE prompts degranulation of mast cells in Ca2+ dependent mechanism. IgE-activated mast cells liberate preformed inflammatory mediators such as histamine and leukotriene 4 that are the first mediators of the allergic response. These mediators attract eosinophils that infiltrate the region amplifying the allergic response.

VKC is a relatively rare chronic allergic inflammation of the ocular surface that mainly affects children and young adolescents. Main symptoms are itching, redness, swelling, discharge and photophobia. The most characteristic sign is giant papillae in the upper tarsal conjunctiva.

AKC is a bilateral chronic inflammatory disease of the ocular surface and eyelid. The most characteristic sign are eczematous lesions on the eyelid which are itchy. It is not unusual for AKC patients to have cataract surgery at a young age {Kari O. and Saari K M 2010}.

GPC is an inflammatory disease characterized by papillary hypertrophy of the superior tarsal conjunctiva. GPC is caused by inert substances rather than allergens. When these irritative stimuli are removed the conjunctival papillary changes resolve. Protein deposits on the surface of the contact lens could become antigenic and stimulate the production of IgE {La Rosa M. et al 2013}.

Current treatments for ocular allergy include non-pharmacologic and pharmacologic strategies. Avoidance of the antigen is the primary behavioural modification for all types of ocular allergies. Artificial tear substitutes provide a barrier function and help to improve the first-line defence at the level of the conjunctiva mucosa. When non-pharmacologic strategies do not provide adequate symptom relief, pharmacologic treatments may be applied.

The mainstay of the management of ocular allergy involves the use of anti-allergic therapeutic agents such as antihistamine, dual-action or combination treatments and mast cell stabilizers. Topical antihistamines (such as Emedastine and Levocabastine) competitively and reversibly block histamine receptors and relieve itching and redness, but only for a short time. Antihistamines do not affect other proinflammatory mediators which remain inhibited. A limited duration of action necessitates frequent dosing and topical antihistamines may be irritating to the eye, especially with prolonged use.

Combination treatments using decongestants (such as oxymetazoline, tetrahydrozoline, and naphazonline) in combination with antihistamines act as vasoconstrictors but are known to sting or burn on instillation. Other adverse events include mydriasis and rebound hyperemia, rendering these combination treatments more suitable for short-term relief. In addition, these drugs are not recommended for use in patients with narrow-angle glaucoma. Mast cell stabilizers (such as cromoglycate, lodoxamide, nedocromil) have a mechanism of action that is unclear. They do not relieve existing symptoms and can be used only on a prophylactic basis to prevent mast cell degranulation with subsequent exposure to the allergen. They require a loading period during which they must be applied before the antigen exposure {La Rosa M. et al 2013}.

When the above mentioned anti-allergic drugs do not allow adequate control of the allergic inflammatory process, anti-inflammatory agents are used. Corticosteroids remain among the most potent pharmacologic agents used in the more severe variants of ocular allergy {La Rosa M. et al 2013}. However, steroidal drugs can have side effects that threaten the overall health of the patient. Chronic administration of corticosteroids can lead to drug-induced osteoporosis by suppressing intestinal calcium absorption and inhibiting bone formation. Other adverse side effects of chronic administration of corticosteroids include hypertension, hyperglycemia, hyperlipidemia (increased levels of triglycerides) and hypercholesterolemia (increased levels of cholesterol) because of the effects of these drugs on the body metabolic processes. It is also known that certain corticosteroids have a greater potential for elevating intraocular pressure ("IOP") than other compounds in this class. For example, it is known that prednisolone, which is a very potent ocular anti-inflammatory agent, has a greater tendency to elevate IOP than fluorometholone, which has moderate ocular anti-inflammatory activity. It is also known that the risk of IOP elevations associated with the topical ophthalmic use of corticosteroids increases over time. In other words, the chronic (i.e., long-term) use of these agents increases the risk of significant IOP elevations. Therefore, corticosteroids may not be appropriate for the long-term treatment of ocular allergies. In addition, chronic use of corticosteroids is contraindicated due to an increased risk for the development of cataracts and glaucoma {Ono S J, and Abelson M B, 2005}.

Allergy immunotherapy is useful in reducing the response to allergens, but its role in allergic conjunctivitis has not been proven. The main objective of this treatment is to induce clinical tolerance to the specific allergen. The therapy is administered subcutaneously in progressively increasing doses to remain below the threshold of a clinical reaction. Sublingual immunotherapy (SLIT) is considered an alternative to subcutaneous allergy immunotherapy and is administered orally under the tongue, but long-term results with SLIT are not yet available. Most of the trials with this form of therapy have been for allergic rhinitis. In general, immune responses to allergen administration are not predictive of the effectiveness of the therapy and the therapy itself can produce systemic reactions, the incidence and severity of which vary dependent of the type of allergen administered {La Rosa M. et al 2013}.

In addition, the majority of newer ophthalmic anti-allergic agents have limited durations of action and twice daily dosing is required. A topical preparation with a longer duration of action would be advantageous because it may be instilled once daily. Thus, new therapies that can offer advantages in areas such as efficacy and duration of action, while offering similar safety profiles than traditional ophthalmic anti-allergic agents, are needed.

RNA interference-based therapies have been pointed out as having the potential to satisfy unmet needs in allergy treatment {Popescu F D. 2005}. It has been demonstrated that systemic administration of CD40 siRNA in mice sensitized with an allergen is capable of attenuating nasal allergic symptoms through inhibition of dendritic cell and B cell functions and generation of regulatory T cells {Suzuki M. et al 2009}. In addition, siRNA-based allergen-specific therapy for allergic rhinitis has also been developed by using CD40-silenced and allergen-pulsed dendritic cells {Suzuki M et al 2010}.

Changes in the intracellular free calcium (Ca2+) concentration in the cell regulate many biological cell functions. Ca2+ signals are generated by the controlled release of Ca2+ from the endoplasmic reticulum (ER) which is the major calcium store in cells. Calcium release from the ER activates store-operated Ca2+ (SOC) channels at the plasma membrane, triggering the store-operated Ca2+ entry (SOCE) of extracellular calcium influx into the cytoplasm. Recent studies highlighted the importance of this Ca2+ entry mechanism in a variety of pathophysiological processes, including allergy {Bergmeier W et al 2013}.

SOCE is activated in response to depletion of ER Ca2+ pools. Activation of SOCE induces Ca2+ entry from extracellular compartments and this is mediated by store-operated Ca2+ release-activated Ca2+ (CRAC) channels {Roth M. et al 1992}.

CRAC channels are composed of calcium sensing proteins called STIM (stromal interaction molecule) and pore-forming subunits named ORAI. Mammalian cells have three ORAI isoforms: ORAI1, ORAI2 and ORAI3; although ORAI2 and ORAI3 fulfill the same role as ORAI1 the Ca2+ currents generated by these proteins are around two- to three fold smaller than the ones generated by ORAI1 {Smyth J. T. et al 2006}.

ORAI1 is a widely expressed, 33 kDa plasma membrane protein with 4 transmembrane domains that is activated by the calcium sensor stromal interaction molecule 1 (STIM1) when calcium stores are depleted and induces extracellular calcium influx into the cytoplasm through the CRAC channels. ORAI1 is also called CRAC Modulator 1, CRACM1, ORAT1, Transmembrane Protein 142A, TMEM142A, or CRAC Channel Protein 1. ORAI1 has been defined as the key subunit of the CRAC channels {Wang Y. et al 2012}.

There is growing evidence that indicates that short-term and long-term activation of immune cells in allergic responses is mediated by influx of Ca2+ to immune cells from the extracellular compartment. Short-term responses include degranulation of mast cells and activation of effector cytolytic T cells. Indeed, mast cells lacking either STIM1 or ORAI1 show a considerable defect in degranulation {Vig M. et al 2008; Baba Y. et al 2008}. Long-term responses involve modulation of gene expression that controls B and T cell proliferation and differentiation {Parekh A. B. et al 2005}.

It has also been suggested that ORAI1 is crucial in mouse mast cell effector function. Mast cells derived from ORAI1-deficient mice showed grossly defective degranulation and the induction of the IgE mediated in vivo passive anaphylaxis response is also dependent on ORAI1. {Vig M, et al 2008}.

ORAI1 knockdown by RNAi has been studied in allergic rhinitis. Recombinant lentivirus vectors that encoded shRNA (short hairpin RNA) against ORAI1 administered into the nostrils of OVA-sensitized mice alleviated allergic rhinitis symptoms (number of sneezes and number of nasal rubbings) {Wang et al 2012}. Rhinitis is produced by nasal irritation or inflammation due to blockage or congestion. Allergic rhinitis is allergic inflammation in the upper airway associated with hyperresponsiveness of several types of immune cells {Wang et al 2012}. However not all the rhinitis cases are caused by allergic reactions. Rhinitis is also produced as a response to chemical exposures including cigarette smoke, temperature changes, infections and other factors.

Another study knocked down ORAI1 with siRNA to attenuate histamine-mediated COX-2 expression and NFkB activation, indicating that ORAL-mediated NFkB activation was an important signaling pathway responsible for transmitting histamine signals that trigger inflammatory reactions in allergic responses {Huang W C et al 2011}.

Therefore, it is likely that an important part of the inflammatory response in ocular allergy is mediated by ORAI1 activation.

There are patent documents referring to siRNA directed to knockdown of ORAI1 for the treatment of an allergy. WO2010/099401 (The Board of Trustees of the Leland Stanford Junior University) describes a method of modulating activity of a CRAC channel in a cell wherein a CRAC channel is contacted with an amino acid residue STIM1 domain that binds to ORAI1 and opens the CRAC channel. Among the treatable conditions are listed: allergy, or hypersensitivity, of the immune system, including delayed type hypersensitivity and asthma. In the description it is indicated that siRNA might be used to disrupt the expression of an endogenous gene to determine whether the endogenous gene has an effect on modulating the interaction between STIM and ORAI proteins.

WO2007/121186 (The Queen's Medical Center) describes siRNA-mediated silencing of human CRACM1 (ORAI1) in human embryonic kidney cells (HEK293). It also indicates that agents that modulate CRAC channel activity via interaction with CRACM1 (ORAI1) protein or disruption of CRACM1 (ORAI1) expression can be used to modulate allergic reactions.

WO2009/095719 (ISIS INNOVATION LIMITED) describes methods, uses and products for use in treating disorders associated with mast cell activation, including combinations of agents which inhibit the CRACM1(ORAI1) protein, which may be siRNAs, and agents which inhibit leukotriene activation of mast cells for use in the treatment of an allergic disorder, specifically allergic rhinitis.

US2011/0112058 (Incozen Therapeutics Pvt. Ltd.) describes a method for identifying a candidate agent for treating lung cancer which preferably inhibits CRACM1/ORAI1. This document describes also the use of siRNA to modulate the CRAC/STIM pathway. It also indicates that CRAC channel modulators have been said to be useful in treatment, prevention and/or amelioration of diseases or disorders associated with calcium release-activated calcium channel, including allergic rhinitis and allergic conjunctivitis.

US2012/0264231 (Hogan Patrick et al) describes methods and systems for identifying an agent, which may be siRNA, which modulates calcium flux through the ORAI channel and/or regulates intracellular calcium via the ORAI channel, for the treatment of conditions and diseases associated with disregulation of calcium signaling, including allergic rhinitis or allergic conjunctivitis.

an important part of the inflammatory response in ocular allergy is mediated by.

ORAI1 not only is a key determinant of the inflammatory response, but it is also related to cell proliferation and cell migration. The inhibition of ORAI1 by a siRNA in retinal pigment epithelia (RPE) cells showed that ORAI1 is involved in epidermal growth factor (EGF)-mediated cell growth. This study hypothesized that ORAI1 might be a potential therapeutic target for drugs aimed at treating EGF-related disorders, such as proliferative vitreoretinopathy (PVR) {Yang et al 2013}. PVR is a disease that develops as a complication of rhegmatogenous retinal detachment, during which fluid from the vitreous humor enters a retinal hole. The mechanisms by which retinal holes or tears are formed are not fully understood yet. The accumulation of fluid in the subretinal space and the tractional force of the vitreous on the retina result in rhegmatogenous retinal detachment. During this process the retinal cell layers come in contact with vitreous cytokines that trigger the ability of the RPE to proliferate and migrate undergoing epithelial-mesenchymal transition (EMT) and develop the ability to migrate out into the vitreous. During this process the RPE cell layer-neural retinal adhesion and RPE-ECM (extracellular matrix) adhesions are lost. The RPE cells lay down fibrotic membranes while they migrate and these membranes contract and pull at the retina. All these finally lead to secondary retinal detachment after primary retinal detachment surgery.

SUMMARY OF THE INVENTION

The present invention provides improved products for reducing ORAI1 expression and consequent ocular inflammation in ocular allergies. The advantage of treating ocular allergies with siRNA products versus traditional anti-allergic therapeutic agents and allergy immunotherapeutic drugs is that treatments based on siRNA will have a longer-lasting effect. This result is due to the fact that once the effector molecule is no longer present, the cell will have to synthesise new receptors from scratch; whereas traditional treatments would leave the levels of receptors on the cell membrane intact.

Ocular allergies appear to be on the rise worldwide. Particularly in industrialized nations, environmental pollution is widely considered a major contributor to the heightened sensitivity of allergic individuals. In addition to worsening emissions pollution, studies have also pointed to a global increase in airborne allergens. Still another consideration is that residents of poorer countries are less likely to seek treatment for ocular allergies, a factor which may keep the reported incidence of the disease artificially low in underdeveloped countries.

Asthma and Allergy Foundation in America (AAFA) indicated that the US annual cost of allergies is estimated to be nearly $14.5 billion. They estimated 50 million Americans suffer from all types of allergies (1 in 5 Americans) including indoor/outdoor, food & drug, latex, insect, skin and eye allergies. US allergy prevalence overall has been increasing since the early 1980s across all age, sex and racial groups.

Despite geographic peculiarities, physicians from around the world find common ground in their criteria for choosing an appropriate treatment course. These criteria include efficacy, safety, and convenience of dosing and comfort of administration for the patient, according to specialists from several countries. Therefore, with an increasing number of patients complaining of a range of ocular allergic symptoms worldwide, finding the optimal treatment is every day both more complex and more interesting.

DESCRIPTION OF THE DRAWINGS

FIG. 1: shows short fragments of the target gene sequence ORAI1 chosen as the target sequences of the siRNAs of the present invention.

FIG. 2: shows oligonucleotide sequences for siRNA molecules of the present invention targeting ORAI1 encompassed by the present invention. The SEQ ID NOs given in the Figure refer to the sense (5'→3') strand; typically siRNAs will be administered as dsRNAs, so will include both the sense strand and its complement antisense strand. SEQ ID NO. 112 to SEQ ID NO. 222 are siRNAs targeting SEQ ID NO. 1 to SEQ ID NO. 111, respectively. Generally, an siRNA will include the sense and antisense strand, and may also include 3' dinucleotide overhangs (for example, dTdT). However, this is not essential.

FIG. 3: modified siRNAs targeting ORAI1. The SEQ ID NOs given refer to the sense (5'→3') strand of the modified ORAI1 siRNAs.

FIG. 21: Chemosis and tearing in response to treatment with different doses of SEQ ID NO. 112 (SYL116011) in a mouse model of ragweed-pollen induced allergy. Mice were observed 1, 3, 6 and 24 h after induction of ocular allergy. A) Conjunctival chemosis and B) tearing were scored on a scale 0-3. Data are expressed as percentage of scoring at 1 h after induction of allergy of the PBS treated group and represent means of 8 animals for PBS and 15 animals for the SEQ ID NO. 112 (SYL116011) treated groups.

FIG. 22: Infiltration of mast cells in palpebral and bulbar conjunctiva in response to treatment with different doses of SEQ ID NO. 112 (SYL116011) in a mouse model of ragweed-pollen induced allergy. A) Infiltration of mast cells in palpebral conjunctiva expressed as percentage of number of mast cells observed in PBS treated samples 3 h after treatment. B) Infiltration of mast cells in bulbar conjunctiva expressed as percentage of number of mast cells observed in PBS treated samples 3 h after treatment.

FIG. 23: Infiltration of eosinophils in palpebral and bulbar conjunctiva in response to treatment with different doses of SEQ ID NO. 112 (SYL116011) in a mouse model of ragweed-pollen induced allergy. A) Infiltration of eosinophils in palpebral conjunctiva expressed as percentage of number of mast cells observed in PBS treated samples 24 h after treatment. B) Eosinophil infiltration in bulbar conjunctiva expressed as percentage of number of eosinophils observed in PBS treated samples 24 h after treatment.

FIG. 24: TLSP and CD-137 expression in response to treatment with different doses of SEQ ID NO. 112

(SYL116011) in a mouse model of ragweed pollen induced-allergy. A) Expression of TLSP; B) Expression of CD-137 (Tnfrsf9).

Figure 25:
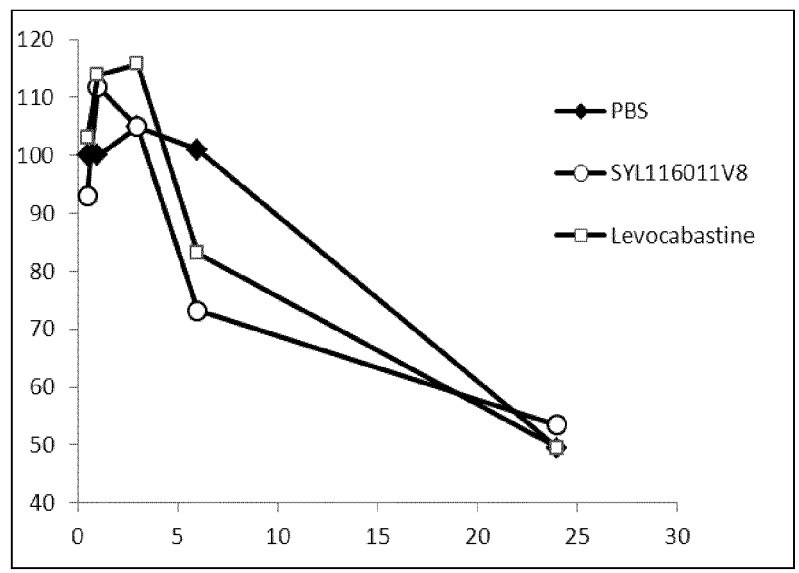

FIG. 25: Clinical signs observed at different time-points after allergy challenge. Allergy was induced by administering an ocular dose of ragweed pollen to mice pretreated with PBS, SEQ ID NO. 227 (SYL116011v8) or levocabastine. Data represent means of 10 animals per group.

Figure 26:
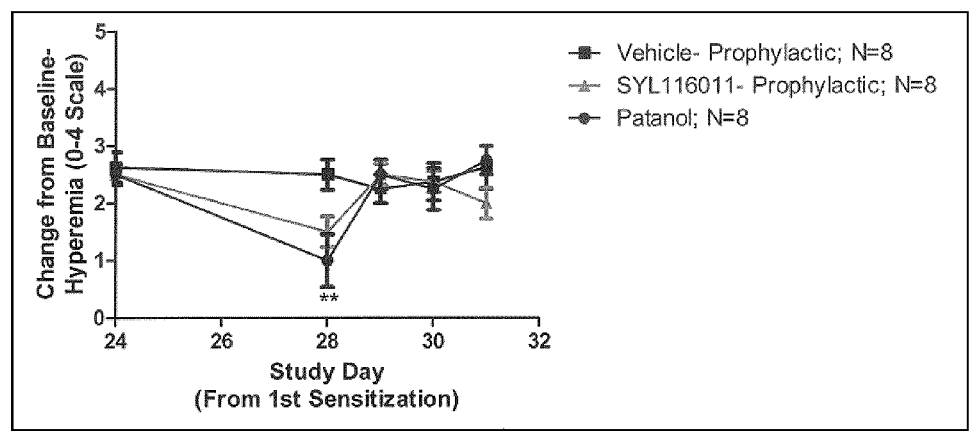

FIG. 26: Change from Post-Dose Hyperemia—SEQ ID NO. 112 (SYL116011) prophylactic versus Patanol® and Vehicle prophylactic.

Figure 27:
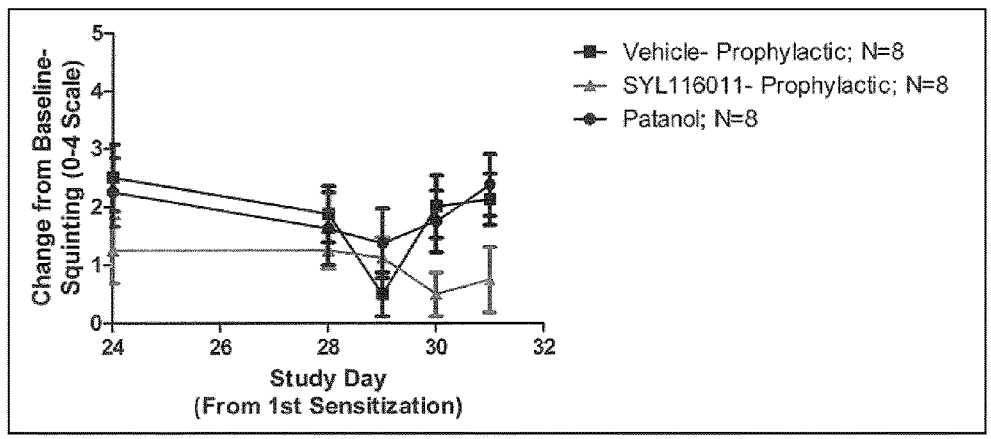

FIG. 27: Change from Post-Dose Squinting—SEQ ID NO. 112 (SYL116011) prophylactic versus Patanol® and Vehicle prophylactic.

Figure 28:
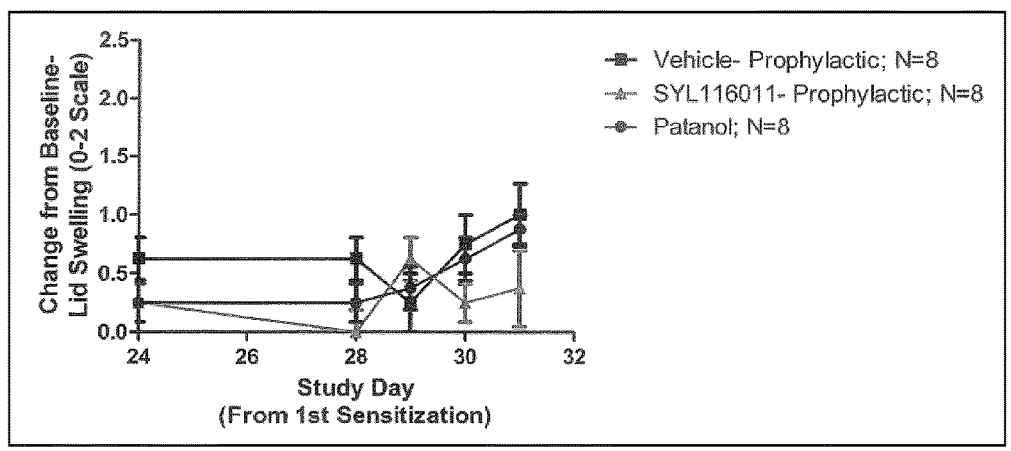

FIG. 28: Change from Post-Dose Lid Swelling—SEQ ID NO. 112 (SYL116011) prophylactic versus Patanol® and Vehicle prophylactic.

Figure 29:
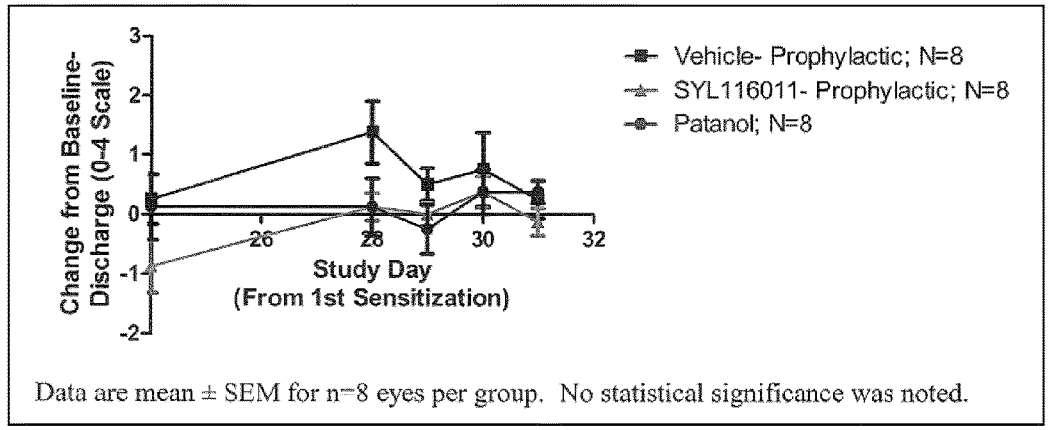

FIG. 29: Change from Post-Dose Discharge—SEQ ID NO. 112 (SYL116011) prophylactic versus Patanol® and Vehicle prophylactic.

DETAILED DESCRIPTION OF THE INVENTION

In a first aspect, the present invention relates to the provision of a siRNA molecule for use as a medicament, in the treatment and/or prevention of an eye condition characterised by increased expression and/or activity of ORAI1, wherein said molecule specifically targets a sequence selected from the group consisting of: SEQ ID NO. 1-SEQ ID NO. 111 and reduces expression of the ORAI1 gene when introduced in a cell. Preferably the target sequence is selected from the group consisting of SEQ ID NO. 1-SEQ ID NO. 14, more preferably the group consisting of SEQ ID NO. 1-SEQ ID NO. 8, and even more preferably the target sequence comprises or consist of SEQ ID NO. 1.

A gene is "targeted" by a siRNA according to the present invention when, for example, the siRNA molecule selectively decreases or inhibits the expression of the gene. The phrase "selectively decrease or inhibit" as used herein encompasses siRNAs that affect expression of one gene, in this case ORAI1. Alternatively, a siRNA targets a gene when (one strand of) the siRNA hybridizes under stringent conditions to the gene transcript, i.e. its mRNA. Hybridizing "under stringent conditions" means annealing to the target mRNA region under standard conditions, e.g., high temperature and/or low salt content which tend to disfavour hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389.

Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

The target sequence as defined above is described as a target DNA sequence as used for definition of transcript variants in databases used for the purposes of designing siRNAs, whereas the specific compounds to be used will be RNA sequences defined as such.

An expert in the field can access any target gene sequence through public data bases. For example, the GenBank Accession Number corresponding to human ORAI1 mRNA is NM_032790 (Gene ID: 84876). Homologous GenBank Accession Number corresponding to mouse ORAI1 mRNA is NM_175423 (Gene ID: 109305). Furthermore, ENSEMBL (MBL-EBI/Wellcome Trust Sanger Institute) has the following ORAI1 human and mouse Accession Number: ENSG00000182500 and ENSMUSG00000049686, respectively. The public transcripts for human ORAI1 mRNA are ENST00000330079 and ENST00000537188.

Said preferred target region identified by the present invention comprises or consists of at least one sequence selected from the group consisting of SEQ ID NO. 1-SEQ ID NO. 111.

In a preferred embodiment, said preferred target region comprises or consists of at least one sequence selected from the group consisting of SEQ ID NO. 1-SEQ ID NO. 14.

In another preferred embodiment, said preferred target region comprises or consists of at least one sequence selected from the group consisting of SEQ ID NO. 1-SEQ ID NO. 8. These sequences present 100% homology between the following species: *Homo sapiens, Mus musculus, Canis lupus familiaris,* and *Rattus norvegicus.*

In the RNAi field, when in vitro studies demonstrated that a human siRNA is not able to induce knock down of the animal model gene, a surrogate compound (animal-active analogue) is synthesized in order to analyze the efficacy of the siRNA in the relevant animal model. This surrogate is designed against the same region as the human siRNA, thus the two siRNAs have the same sequence except for a few nucleotides, depending on the homology between the human and the rabbit target gene. This approach has been widely used for development of other oligonucleotides, specifically for toxicology studies {Kornbrust D. et al. 2013}.

In a more preferred embodiment, said preferred target region comprises or consists of SEQ ID NO. 1 (5'-TGATGAGCCTCAACGAGCA-3').

Consequently, a siRNA according to the aspects of the present invention will preferably comprise a double stranded RNA molecule, whose antisense strand will comprise an RNA sequence substantially complementary to at least one sequence selected from the group consisting of SEQ ID NO. 1-SEQ ID NO. 111, and whose sense strand will comprise an RNA sequence complementary to the antisense strand, wherein both strands are hybridised by standard base pairing between nucleotides. More preferably, a siRNA according to aspects of the present invention will preferably comprise a double stranded RNA molecule, whose antisense strand will comprise an RNA sequence substantially complementary to selected from the group consisting of SEQ ID NO. 1-SEQ ID NO. 8, and even more preferably consisting of SEQ ID NO. 1.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 85%, 86%, 87%, 88%, 89%, 90%, 91%, 92%, 93%, 94%, 95%, 96%, 97%, 98% or 99% complementarity to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule. In a preferred embodiment, the antisense siRNA strand is 100% complementary to the target mRNA sequence, and the sense strand is 100% complementary to the antisense strand over the double stranded portion of the siRNA. The siRNA may also include unpaired overhangs, for example, 3' dinucleotide overhangs, preferably dTdT.

In a preferred embodiment, said eye condition identified by the present invention is an ocular allergy and/or ocular conjunctivitis. More preferably, said eye condition is selected from seasonal allergic conjunctivitis, perennial allergic conjunctivitis, vernal keratoconjunctivitis, atopic keratoconjunctivitis, giant papillary conjunctivitis, dry eye syndrome and combinations thereof.

As is known from the state of the art, many different structures have been proposed to achieve RNA interference. Generally these double stranded molecules are from about 19 to about 25 nucleotides in length, and include blunt-ended structures as well as those with overhangs. Overhangs have been described to be advantageous and may be present on the 5' ends or on the 3' ends of either strand as they reduce recognition by RNAses and imitate Dicer's natural substrate. Some authors recommend including overhangs on both 3' ends of the molecules, whereas others consider one overhang to be sufficient. Others have described the use of blunt-ended structures with specific modification patterns (EP 1527176, WO 2005/062937, WO 2008/104978, EP 2322617, EP 2348133, US 2013/0130377, and many others).

Overhangs may be comprised of between 1 and 5 nucleotides; typically overhangs are made up of dinucleotides. Classical molecules used in the field, comprise a 19 nucleotide double stranded molecule which further comprises 3' dinucleotide overhangs preferably comprising deoxynucleotides as taught in initial studies by Tuschl (WO02/44321). These overhangs are said to further enhance resistance to nuclease (RNase) degradation. Later, Kim et al 2005 describe that 21-mer products (containing dinucleotide overhangs) are necessary for loading onto RISC. Further, Bramsen et al. 2009 describe the introduction of possible destabilizing modifications to the overhangs to further increase silencing efficiency.

As such, a preferred embodiment of the various aspects of the present invention refers to siRNA molecules targeting at least one sequence selected from the group consisting of SEQ ID NO. 1-SEQ ID NO. 111 which comprise at least one overhang. More preferably, said siRNA molecules target at least one sequence selected from the group consisting of SEQ ID NO. 1-SEQ ID NO. 8, and even more preferably consisting of SEQ ID NO. 1. Where the invention relates to an siRNA molecule targeting at least one sequence selected from SEQ ID NO. 1 to SEQ ID NO. 111, the siRNA will include an antisense strand of equivalent length and complementary to the target, and a sense strand of equivalent length and complementary to the antisense strand. The antisense and sense strands may further include additional bases which are not complementary to the other strand or the target, and/or which are not paired in the double stranded portion of the siRNA. For example, SEQ ID NO 1 is a 19 nucleotide sequence; the siRNA may include a 19 by double stranded region over this portion of sequence identity, and dinucleotide overhangs.

A preferred embodiment of the various aspects of the present invention refers to siRNA molecules targeting at least one sequence selected from the group consisting of SEQ ID NO. 1-SEQ ID NO. 111, wherein each strand of the double-stranded siRNA molecules is about 18 to about 28 or more (e.g., about 18, 19, 20, 21, 22, 23, 24, 25, 26, 27, or 28 or more) nucleotides long.

Another preferred embodiment of the various aspects of the present invention refers to siRNA molecules of 18-28 nucleotides long or more and comprising a nucleotide sequence selected from the group consisting of SEQ ID NO. 112-SEQ ID NO. 229. More preferably, the double-stranded siRNA molecules are at least 19 nucleotides long and selected from the group consisting of SEQ ID NO. 112-SEQ ID NO. 229.

Another alternative embodiment of the various aspects of the present invention provides blunt-ended molecules.

Further, a preferred embodiment of the present invention relates to an siRNA comprising or consisting of a 19 nucleotide double-stranded structure targeting at least one sequence selected from the group consisting of SEQ ID NO. 1-SEQ ID NO. 111. More preferably, the siRNA comprising or consisting of a 19 nucleotide double-stranded structure targeting at least one sequence selected from the group consisting of SEQ ID NO. 1-SEQ ID NO. 8, and even more preferably consisting of SEQ ID NO. 1.

A particular embodiment of the present invention relates to a 19 nucleotide double-stranded blunt-ended siRNA targeted against at least one sequence selected from the group consisting of SEQ ID NO. 1-SEQ ID NO. 111. More preferably, the siRNA is targeted against at least one sequence selected from the group consisting of SEQ ID NO. 1-SEQ ID NO. 8, and even more preferably consisting of SEQ ID NO. 1. In a further particular embodiment this compound comprises or consists of at least one sequence selected from the group consisting of SEQ ID NO: 112-SEQ ID NO. 229. In a further preferred embodiment, the antisense strand of this siRNA is at least 80%, preferably at least 90%, complementary to at least one sequence selected from the group consisting of SEQ ID NO. 1-SEQ ID NO. 111.

In a preferred embodiment, this compound comprises or consists of at least one sequence selected from the group consisting of SEQ ID NO. 112-SEQ ID NO. 119.

In a more preferred embodiment, this compound comprises or consists of SEQ ID NO. 112 (5'-UGAUGAGC-CUCAACGAGCA-3'), corresponding to the sense strand of our referenced compound named SYL1160011.

Furthermore, as described in the section termed background of the art, an important issue with siRNA molecules is their instability in biological fluids due to the ubiquitous nature of RNAses. Consequently, the use of many different chemical modifications to nucleotides has been described with the purpose of enhancing compound stability.

Another inherent problem of siRNA molecules is their immunogenicity, whereby siRNAs have been found to induce unspecific activation of the innate immune system, including up-regulation of certain cytokines, e.g. type I and/or type II interferon as well as IL-12, IL-6 and/or TNF-alpha production. The origin of these effects is thought to be activation of Toll-like receptors such as TLR7, TLR8 and/or TLR3 by siRNA.

Both of these effects, recognition by RNases and immunogenicity, have also been described to be sequence-dependent.

Some of the chemical modifications which enhance compound stability by decreasing susceptibility to RNAses are also able to reduce induction of immune recognition of subsequent response. However, insertion of chemically modified nucleotides in a siRNA may also result in decreased silencing efficacy as described in the previous section, and hence must be approached with caution.

Consequently, in a preferred embodiment of the various aspects of the present invention, the siRNA further comprises at least one nucleotide with a chemical modification.

Preferred chemical modifications which enhance stability and reduce immunogenic effects include 2'-O-methyl nucleotides, 2'-fluoro nucleotides, 2'-amino nucleotides, 2'-deoxy nucleotides, or nucleotides containing 2'-O or 4'-C methylene bridges. Other preferred chemical modifications for exonuclease protection include ExoEndoLight (EEL): modification of all pyrimidines in the sense strand to 2'-O-methyl residues, and modifications of all pyrimidines in a 5'-UA-3' or 5'-CA-3' motif in the antisense strand. In addition, position 1 of the sense strand can also be changed to 2'-O-methyl, preventing 5'-phosphorylation of the sense strand and thus increasing specificity of the siRNA by further inactivating the sense strand. In addition, the sense strand can also include a 2'-O-methyl modification in position 14, because 2'-O-Me at this position further inactivates the sense strand and therefore increases specificity of the siRNAs. In addition, other preferred chemical modifications for exonuclease protection include Methyl-Fluoro (MEF): exo-protection alternating 2'-fluoro and 2'-O-methyl modifications starting (5'-end) with a 2'-F on the sense strand and starting with 2'-O-Me on the antisense strand. In addition, position 1 of the sense strand can also be changed to 2'-O-Me and position 1 of the antisense strand to 2'-F (as this can efficiently be 5'-phosphorylated). Also, modification of the ribonucleotide backbone connecting adjacent nucleotides can be made by the introduction of phosphorothioate modified nucleotides. A further preferred chemical modification within the meaning of the present invention relates to the substitution of uracyl ribonucleotides with deoxythymidine (deoxyribonucleotides). In another preferred embodiment of the present invention, the at least one chemically modified nucleotide is on the sense strand, on the antisense strand or on both strands of the siRNA.

Accordingly, in one embodiment, the siRNA comprises or consists of at least one sequence selected from the group consisting of SEQ ID NO. 223-SEQ ID NO. 229.

siRNA molecules as described above may be delivered to the cell interior in their native structure using methods known in the art. For example, when studying in vitro gene silencing, these compounds are administered using standard transfection reagents. To achieve effects in vivo these compounds may also be administered naked or using delivery enhancing agents such as for example liposomes, conjugation with a specific moiety, etc. although many different alternatives are known in the art, and are used differently depending on the desired target site within the body.

Alternatively, siRNA molecules of the various aspects of the invention can be expressed within cells from eukaryotic promoters. Recombinant vectors capable of expressing the siRNA molecules can be delivered and persist in target cells.

Alternatively, vectors can be used that provide for transient expression of nucleic acid molecules. Such vectors can be repeatedly administered as necessary. Once expressed, the siRNA molecule interacts with the target mRNA and generates an RNA interfering response. The siRNA molecules produced in this manner are often termed shRNA (short hairpin RNA), as their sense and antisense strands are joined by a small loop of nucleotides. Delivery of siRNA molecule expressing vectors can be systemic, such as by intravenous or intra-muscular administration, by administration to target cells ex-planted from a subject followed by reintroduction into the subject, or by any other means that would allow for introduction into the desired target cell.

A further aspect of the invention relates to the use of siRNA targeting at least one sequence selected from the group consisting of SEQ ID NO. 1-SEQ ID NO. 111 in the preparation of a medicament for use in a method of treatment of an eye condition characterised by increased expression and/or activity of ORAI1. More preferably, said at least one sequence is selected from the group consisting of SEQ ID NO. 1-SEQ ID NO. 8, and even more preferably said at least one sequence consists of SEQ ID NO. 1. The method comprises inhibiting expression of ORAI1 in a patient. The term inhibition is used to indicate a decrease or downregulation of expression or activity. Preferably, the eye condition is an ocular allergy and/or conjunctivitis. In one embodiment, the eye condition is selected from the group comprising seasonal allergic conjunctivitis, perennial allergic conjunctivitis, vernal keratoconjunctivitis, atopic keratoconjunctivitis, giant papillary conjunctivitis, dry eye syndrome and combinations thereof.

Also provided is a method of treatment of an eye condition characterised by increased expression and/or activity of ORAI1. The method comprises inhibiting expression of ORAI1 in a patient. The method may comprise administering siRNA targeting at least one sequence selected from the group consisting of SEQ ID NO. 1-SEQ ID NO. 111 More preferably, said at least one sequence is selected from the group consisting of SEQ ID NO. 1-SEQ ID NO. 8, and even more preferably said at least one sequence consists of SEQ ID NO. 1.

In some countries, the combination of chronic allergic conjunctivitis and dry eye syndrome is quite common. The increasing dry eye problem is due to common artificial climatization, indoor and outdoor pollutants and to other unknown reasons. Patients with dry eye syndrome are more prone to suffer from ocular allergies since the tear film is an important barrier in preventing allergens from coming into contact with mast cells.

Therapeutic treatment with siRNAs directed against ORAI1 mRNA is expected to be beneficial over small molecule topical ocular drops by increasing the length of time that effect is observed, thereby allowing less frequent dosing and greater patient compliance. This is especially important in cases such as ocular allergies and/or conjunctivitis, comprising but not limited to vernal keratoconjunctivitis, atopic keratoconjunctivitis, and giant papillary conjunctivitis, as they are often chronic conditions.

Bearing in mind the preparation of such a medicament, the siRNA of the various aspects of the present invention may be formulated as a pharmaceutical composition. Preferably, the compositions and formulations of said siRNAs may be administered topically to the organ of interest. In an even more preferred embodiment they may be formulated for topical administration to the eye, preferably to the corneal surface of the eye. Application to the corneal surface may, for example be in the form of eye drops, a gel, lotion, cream or ocular inserts. Other administration forms to the eye may include injection into the eye.

A further preferred embodiment of the various aspects of the present invention relates to an siRNA specifically targeting at least one sequence selected from the group consisting of SEQ ID NO. 1-SEQ ID NO. 111 as described in the preceding paragraphs, for use as a medicament for the treatment of an eye condition characterised by increased expression and/or activity of ORAI1. More preferably, said at least one sequence is selected from the group consisting of SEQ ID NO. 1-SEQ ID NO. 8, and even more preferably said at least one sequence consists of SEQ ID NO. 1. As described above, it may be an siRNA comprising or consisting of a 19 nucleotide double-stranded structure targeting at least one sequence selected from the group consisting of SEQ ID NO. 1-SEQ ID NO. 111. This siRNA may be blunt-ended. Preferably, the siRNA comprises or consists of at least one sequence selected from the group consisting of SEQ ID NO. 112-SEQ ID NO. 229. Other siRNA for use according to the invention comprises or consists of at least one sequence from the group consisting of SEQ ID NO. 223-SEQ ID NO. 229.

Within the context of the present invention, to "specifically target" a sequence the siRNA of the invention preferably comprises at least the same seed sequence. Thus, any sequence according to the invention that specifically targets at least one sequence selected from the group consisting of SEQ ID NO. 1-SEQ ID NO. 111 is preferably identical in positions 2-8 of the antisense strand. More preferably, said at least one sequence is selected from the group consisting of SEQ ID NO. 1-SEQ ID NO. 8, and even more preferably said at least one sequence consists of SEQ ID NO. 1.

Notwithstanding the above, the siRNAs of the various aspects of the present invention may be used to silence ORAI1 expression in tissues other than the eye. Consequently, said siRNAs should be formulated accordingly.

For example, a siRNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In one embodiment of the present invention, the siRNA molecule is delivered through a cell-specific siRNA carrier that combines components of the hepatitis B virus and liposomes. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. The preferred compositions of the invention are aqueous solutions, specifically saline solutions such as phosphate-buffered saline (PBS) with a pH range of about 7.0 to about 7.4, preferably with a pH of 7.2±0.5.

A siRNA molecule of the invention may be complexed with membrane disruptive agents and/or a cationic lipid or helper lipid molecule.

Delivery systems which may be used with the invention include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) a disease state. The pharmaceutically effective dose generally depends on the type of disease, the composition used, the route of administration, the type of mammal being treated, the physical characteristics of the specific mammal under consideration, concurrent medication, and other factors that those skilled in the medical arts will recognize.

A therapeutically effective amount may also refer to the amount of a siRNA sufficient to delay or minimize the onset of an eye disorder associated with ocular allergy. A therapeutically effective amount may also refer to the amount of the therapeutic agent that provides a therapeutic benefit in the treatment or management of an eye disorder associated with ocular allergy. Further, a therapeutically effective amount with respect to a siRNA of the invention means that amount of therapeutic agent alone, or in combination with other therapies, that provides a therapeutic benefit in the treatment or management of an eye disorder associated with ocular allergy. Used in connection with an amount of a siRNA of the invention, the term can encompass an amount that improves overall therapy, reduces or avoids unwanted effects, or enhances the therapeutic efficacy of or synergizes with another therapeutic agent.

A therapeutic benefit in the treatment or management of an eye disorder such as ocular allergy is the sustained decrease in allergic symptoms. Given that siRNA will decrease the levels of ORAI1 within the cell, once the treatment stops the cell must re-synthesise new proteins. As such therapies based on siRNA treatments will have a more sustained effect. This is considered a significant enhancement of the therapeutic efficacy.

An additional benefit of using siRNA is the minimum probability of side effects or acute toxicity issues derived from its presence in systemic circulation, often associated with different eyedrop-based treatments. This is due to the fact that when the compound enters the bloodstream, it will be rapidly degraded by RNAses present in the blood.

On the other hand, the fact that the siRNA molecule can be marketed in single dose vials means addition of antimicrobial preservatives to the formulation can be avoided. Preservatives are present in the majority of formulations on the market today. These preservatives can produce intolerance in some patients, making it necessary to stop the treatment. Both issues are especially important when bearing in mind that conditions such as ocular allergies and/or conjunctivitis, comprising but not limited to vernal keratoconjunctivitis, atopic keratoconjunctivitis, and giant papillary conjunctivitis, are often chronic and therefore so is the treatment.

One of the preferred administration routes is topical, by instillation directly to the eye, preferably using eyedrops. As described above, therapeutic treatment with siRNAs directed against ORAI1 mRNA is expected to be beneficial over small molecule topical ocular drops by increasing the length of time that the effect is observed, thereby allowing less frequent dosing and greater patient compliance.

However, as explained above, administration routes other than directly to the eye can also be used. The precise dosage and administration schedule to be employed in the formulation will also depend on the route of administration. A skilled person would understand that the precise dosage and administration schedule to be employed also depends on the seriousness of the disorder, and should be decided according to the judgment of the practitioner and each patient's circumstances. It is also understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The formulations or siRNA of the invention and described herein can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agent. The pharmaceutical compositions or siRNA of the invention and described herein can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

In preferred embodiments, the compositions of the invention are formulated in a solution, preferably a buffered saline solution such as PBS, or a gel for topical administration to the eye, such as, for example, in the form of eyedrops. In such embodiments, the formulations may be cationic emulsions and/or contain biopolymers including, but not limited to, poly(lactide-co-glycolide), carbopol, hyaluronic acid and polyacrylic acid.

The nucleic acid molecules of the invention can also be administered in the form of suppositories, e. g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

As such, a further preferred embodiment of the present invention relates to a pharmaceutical composition wherein said composition comprises at least an siRNA targeting at least one sequence selected from the group consisting of SEQ ID NO. 1-SEQ ID NO. 111, as has been described in the preceding paragraphs. More preferably, said at least one sequence is selected from the group consisting of SEQ ID NO. 1-SEQ ID NO. 8, and even more preferably said at least one sequence consists of SEQ ID NO. 1.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

As used herein the terms "ocular allergy" refers to an allergic disorder of the ocular surface caused by increased expression and/or activity of ORAI1. It may also be called allergic conjunctivitis. Ocular allergy includes a wide variety of pathological conditions including but not limited to: seasonal allergic conjunctivitis (SAC), perennial allergic conjunctivitis (PAC), vernal keratoconjunctivitis (VKC), atopic keratoconjunctivitis (AKC), and giant papillary conjunctivitis (GPC).

As used herein the terms "conjunctivitis" refers to an inflammation of the conjunctiva. It is also called pink eye or madras eye in India. It is commonly due to an infection (usually viral, but sometimes bacterial) or an allergic reaction.

"Clinical symptoms" of ocular allergy include but are not limited to ocular itching, ocular redness, swelling of the eyelids, chemosis, tearing, and nasal inflammation, nasal congestion, rhinorrhea, nasal pruritis and ear/palate pruritis, and sneezing. It is preferred that the present invention treats or prevents at least two clinical symptoms, more preferably at least three, even more preferably more than four.

The term "patient," as used herein, refers to animals, including mammals, preferably humans.

As used herein the term "allergen" refers to any antigenic substance in the environment that is capable of producing immediate hypersensitivity (allergy). The list of known allergens includes plant pollens, spores of mold, animal dander, house dust, foods, feathers, dyes, soaps, detergents, cosmetics, plastics, and drugs. Allergens can enter the body by being inhaled, swallowed, touched, or injected. Airborne allergens are allergens that are light enough to be carried through air currents, for example but not limited to, pollen or spores.

The term "allergic conjunctivitis" in the present invention is understood as inflammation of the conjunctiva caused by an allergic reaction. The conjunctiva is a thin membrane that covers the eye. When an allergen irritates the conjunctiva, common symptoms that occur in the eye include: redness (mainly due to vasodilation of the peripheral small blood vessels), ocular itching, eyelid swelling, increased lacrimation, photophobia, watery discharge, and foreign body sensation (with pain). Symptoms are usually worse for patients when the weather is warm and dry, whereas cooler temperatures and rain tend to assuage symptoms.

The term "blepharitis" in the present invention is understood as a chronic inflammation of the eyelid.

The term "blepharoconjunctivitis" in the present invention is understood as the simultaneous occurrence of two separate eye conditions: blepharitis and conjunctivitis. Blepharitis affects the outer eyelids, while conjunctivitis occurs in the conjunctiva.

The term "keratoconjunctivitis" in the present invention is understood as the inflammation of the cornea and conjunctiva.

The invention is further described in the following non-limiting examples.

EXAMPLES

0. Materials
    Mouse ORAI1 Probe: Taqman Gene Expression Assay Mm00774349_m1.
    Mouse TLSP Probe: Taqman Gene Expression Assay Mm01157588_m1.
    Mouse TNFSR9 probe: Taqman Gene Expression Assay Mm00441899_m1.
    18S Endogenous control: Taqman Gene Expression Assay. Hs99999901_s1.
    Multiscribe Reverse Transcriptase 50 U/ml (Applied Biosystems P/N 4311235).
    RNAse inhibitor 20 U/µl (Applied Biosystems P/N N8080119).
    TaqMan 2× Universal Master Mix.
    Non Radioactive Cell Proliferation Assay kit (Promega, Mannheim, Germany).
    Human mast cells (HMC-1).
    Ionomycin calcium salt 1 mM in DMSO (from Sigma Life Science Ref# I3909-1 ml).
    Annexin-V detection kit Life Technologies (Ref: V13241).
1. In Vitro Analysis
1.1 ORAI1 Expression Levels after Transfection of siRNAs of the Present Invention in Different Cell Lines.

Figure 4:
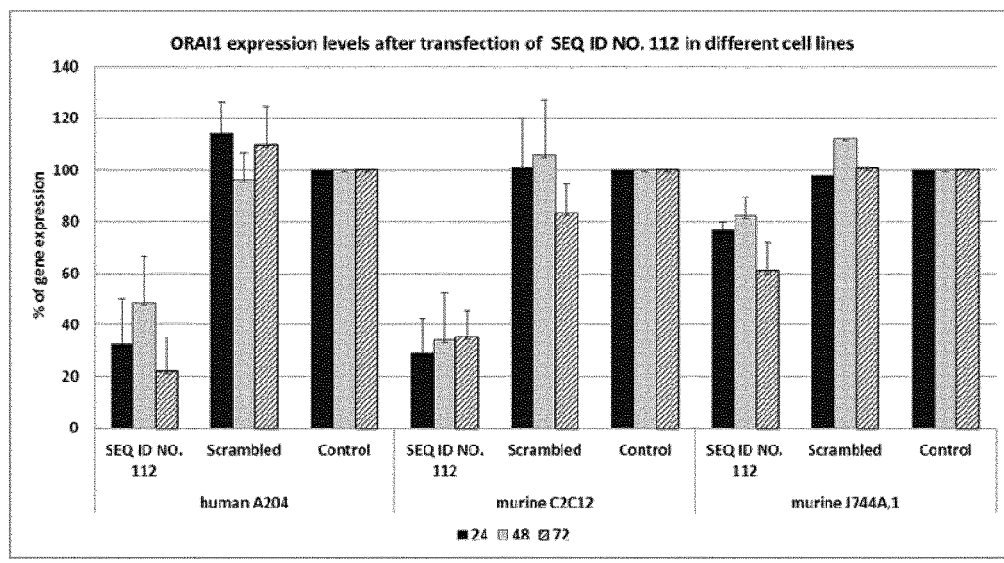
FIG. 4: in vitro ORAI1 expression levels after transfection of SEQ ID NO. 112 in different cell lines (human A204, murine C2C12 and murine J744A,1).
Figure 5:
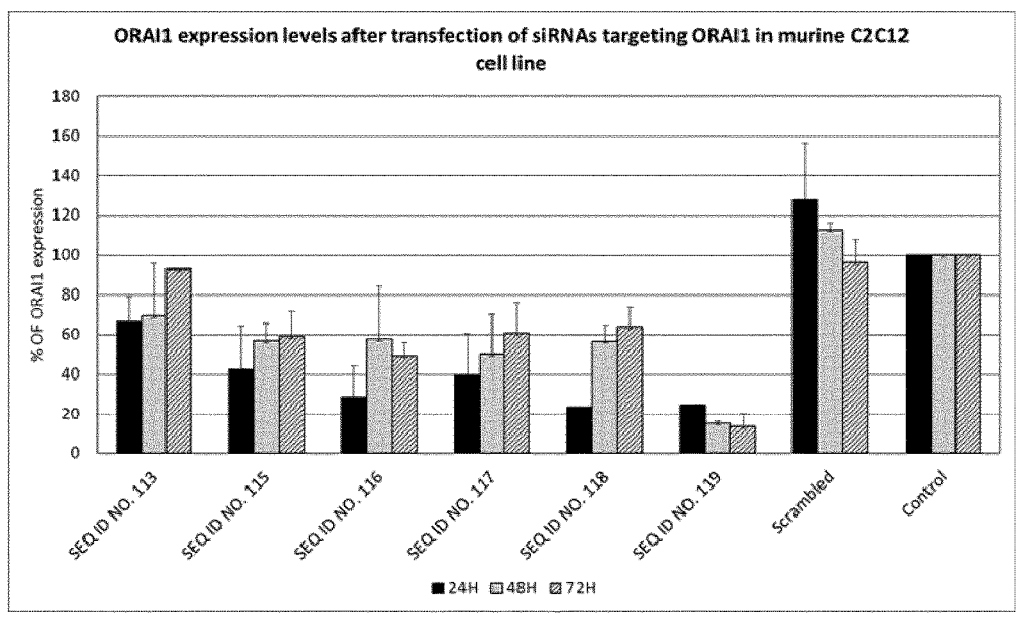
FIG. 5: in vitro ORAI1 expression levels after transfection of siRNAs targeting ORAI1 in murine C2C12 cell line.

In order to demonstrate the silencing effect of the siRNAs of the present invention, in vitro ORAI1 expression levels were measured after transfection of a selection of siRNAs of the present invention in different cell lines. Human A204 and murine C2C12 and J744A.1 cells were transfected with 100 nM of SEQ ID NO. 112, 19 bp blunt ended dsRNA structure, with Transit TKO and Lipofectamine 2000 respectively as transfection agent. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations in mRNA levels as a consequence of siRNA mechanism of action. RNA levels were quantified by real-time PCR using a relative quantitation method, the Comparative Threshold 2-ΔΔ CT method. (Livak and Schmittgen, 2001). All real time quantitative PCR experiments were performed in triplicate and repeated in three independent experiments. Mean and standard deviation were calculated. As FIG. 4 shows, SEQ ID NO. 112 reduced significantly ORAI1 mRNA levels approximately 70-80% in A204 and C2C12 cells and 40% in J744A.1. SEQ ID NO. 113, SEQ ID NO. 115, SEQ ID NO. 116, SEQ ID NO. 117, SEQ ID NO. 118 and SEQ ID NO. 119, 19 bp blunt ended dsRNA structures, also significantly reduced ORAI1 mRNA expression levels approximately 40-80% (FIG. 5).

1.2 Cellular Viability of Different Cell Lines after Transfection with a siRNA of the Present Invention.

Figure 6:
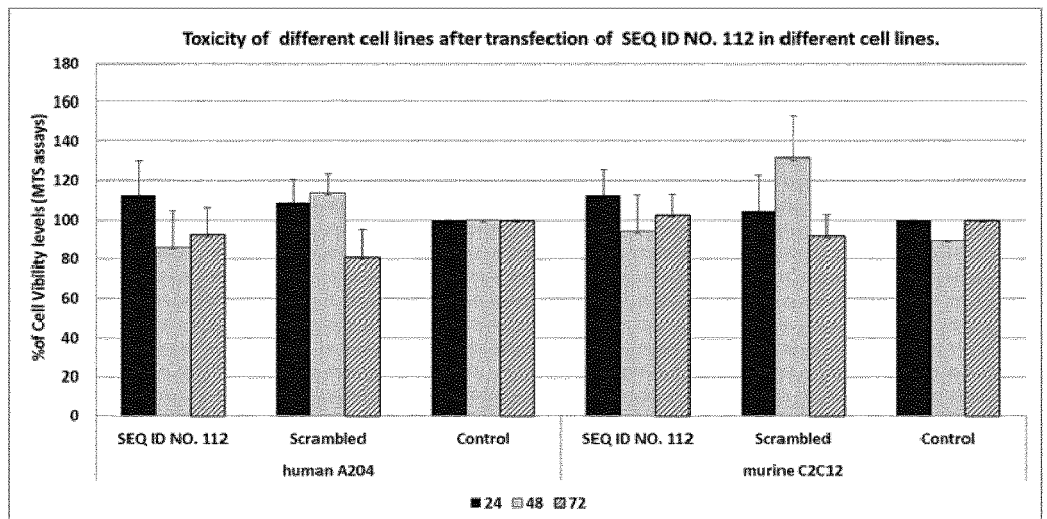
FIG. 6: in vitro toxicity levels of different cell lines after transfection of SEQ ID NO. 112 in different cell lines (human A204 and murine C2C12).

In order to demonstrate the cellular viability of the siRNAs of the present invention, in vitro toxicity levels were measured after transfection of a selection of siRNAs of the present invention in different cell lines. Human A204 and murine C2C12 and J744A.1 cells were transfected with 100 nM of SEQ ID NO. 112 (19 bp blunt ended dsRNA structure) with Transit TKO and Lipofectamine 2000 respectively as transfection agent. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations in cell viability levels as a consequence of siRNA transfection. Cell viability was measured using CellTiter 96® Aqueous Non-Radioactive Cell. Proliferation Assay from Promega. This method is based on capacity of living cells (dehydrogenase enzymes) to reduce the MTS tetrazolium compound into formazan product as measured by the amount of 490 nm absorbance. Mean and standard deviation were calculated. As FIG. 6 shows no changes in cell viability levels were found for SEQ ID NO. 112. Therefore, SEQ ID NO. 112 is not toxic and it is safe.

1.3 ORAI1 Expression Levels after Transfection of Unmodified and Chemically Modified siRNA of the Present Invention in Different Cell Lines.

Figure 7:
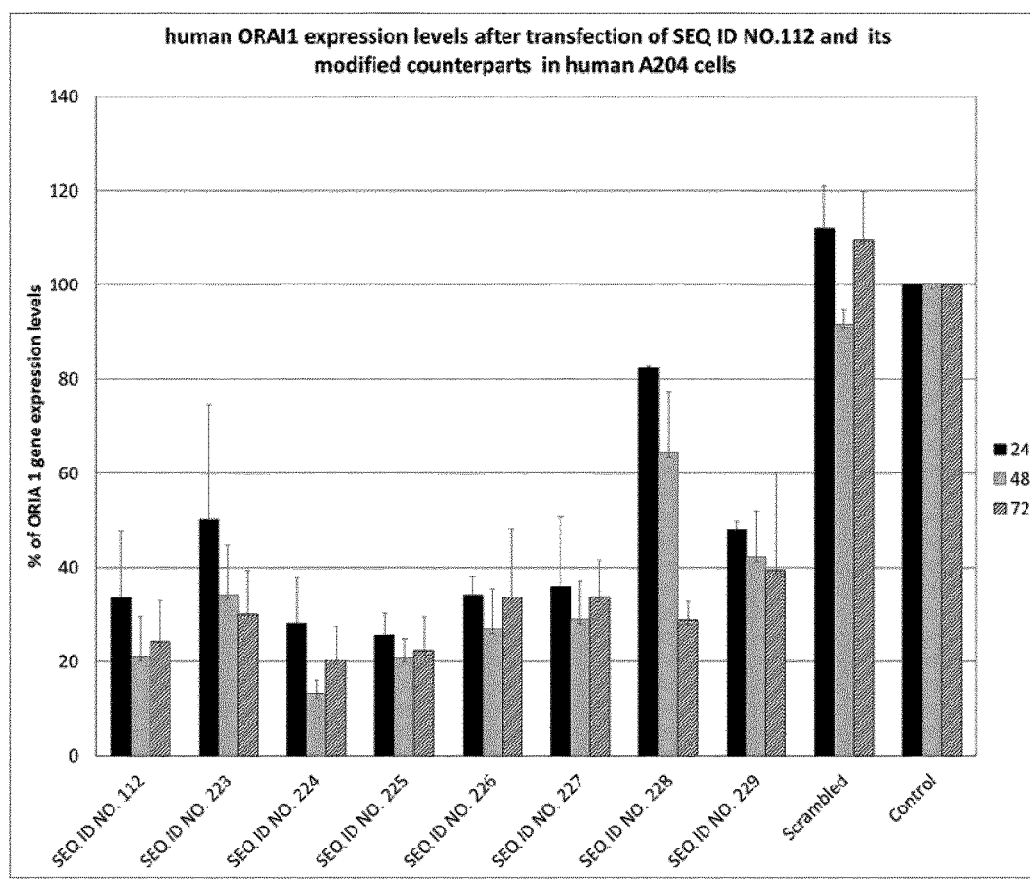
FIG. 7: in vitro human ORAI1 expression levels after transfection of SEQ ID NO. 112 and its modified counterparts, SEQ ID NO. 223, SEQ ID NO. 224, SEQ ID NO. 225, SEQ ID NO. 226, SEQ ID NO. 227, SEQ ID NO. 228, and SEQ ID NO. 229, in human A204 cells.
Figure 8:
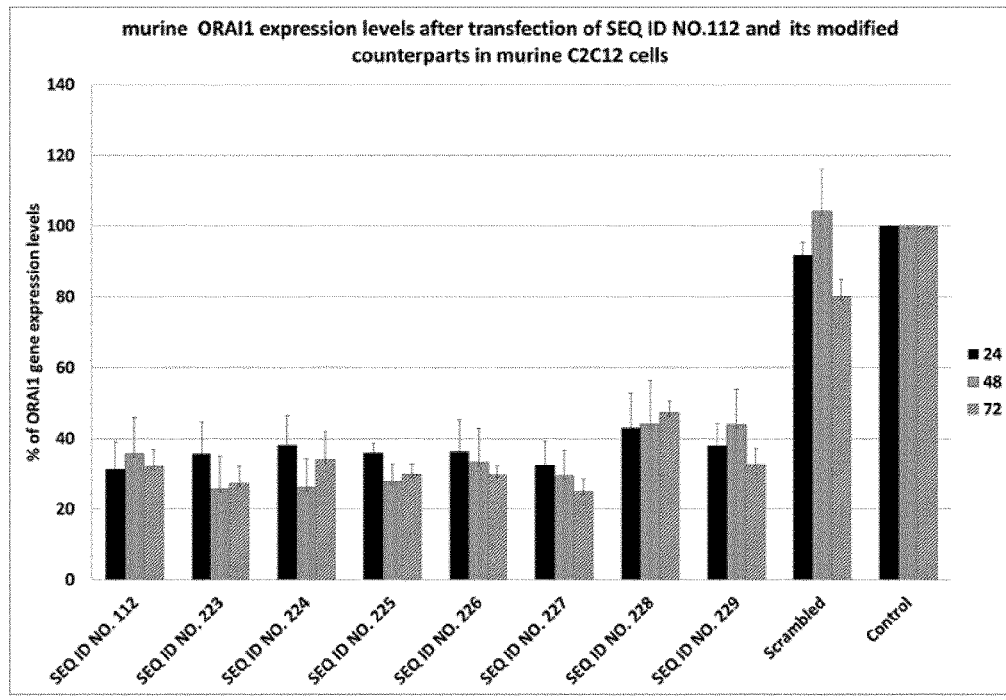
FIG. 8: in vitro murine ORAI1 expression levels after transfection of SEQ ID NO. 112 and its modified counterparts, SEQ ID NO. 223, SEQ ID NO. 224, SEQ ID NO. 225, SEQ ID NO. 226, SEQ ID NO. 227, SEQ ID NO. 228, and SEQ ID NO. 229, in murine C2C12 cells.

In order to improve the stability of siRNAs of the present invention and to ensure no immunogenic activation, different siRNA-optimized chemical modifications were introduced to the canonical SEQ ID NO. 112 sequence (19 bp blunt ended dsRNA structure); thus new chemically modified entities (SEQ ID NO. 223, SEQ ID NO. 224, SEQ ID NO. 225, SEQ ID NO. 226, SEQ ID NO. 227, SEQ ID NO. 228 and SEQ ID NO. 229) were obtained and transfected in human and murine cells to prove their ability to reduce ORAI1 mRNA levels. Chemical modifications are detailed in FIG. 3. Human A204 and murine C2C12 and J744A.1 cells were transfected with 100 nM of SEQ ID NO. 112, SEQ ID NO. 223, SEQ ID NO. 224, SEQ ID NO. 225, SEQ ID NO. 226, SEQ ID NO. 227, SEQ ID NO. 228 or SEQ ID NO. 229 (all these structures correspond to 19 bp blunt ended dsRNA structures) with Transit TKO and Lipofectamine 2000 respectively as transfection agent. All transfections were performed following standard manufacturer's instructions. In the same transfection a scrambled siRNA sequence was used as a control of the specificity of interference. Cell pellets were collected at 24, 48, and 72 hours after transfection experiment and processed to evaluate possible variations in mRNA levels as a consequence of the siRNA-treatment. RNA levels were quantified by real-time PCR using a relative quantitation method, the Comparative Threshold 2-ΔΔ CT method {Livak and Schmittgen, 2001}. All real time quantitative PCR experiments were performed in triplicate and repeated in three independent experiments. Mean and standard deviation were calculated. As FIG. 7 and FIG. 8 show, modified siRNAs showed excellent efficacy, comparable to SEQ ID NO. 112, both in human and murine cell lines. Thus, chemically modified products SEQ ID NO. 223, SEQ ID NO. 224, SEQ ID NO. 225, SEQ ID NO. 226, SEQ ID NO. 227, SEQ ID NO. 228 and SEQ ID NO. 229 reduced ORAI1 mRNA levels between 50-80%.

1.4 Dose Response of SEQ ID NO. 112 and SEQ ID NO. 227 in Human and Murine Cells.

Figure 9:
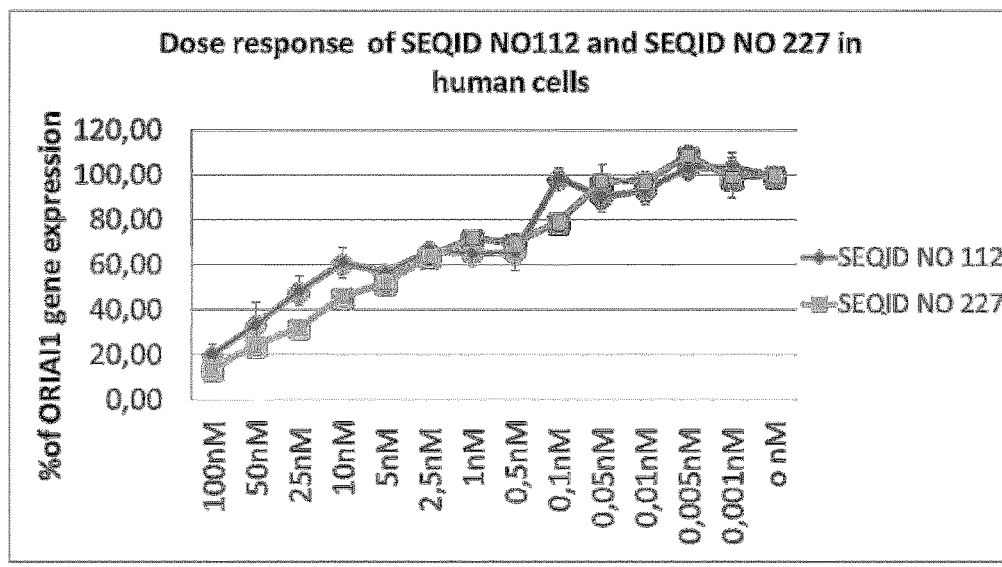
FIG. 9: shows the dose response of SEQ ID NO. 112 (SYL116011) and SEQ ID NO. 227 (SYL116011v8) in human cells. Transfections of Human A204 cells with increasing doses (0.001 to 100 Nm) of SEQ ID NO. 112 (SYL116011) and SEQ ID NO. 227 (SYL116011v8) and quantification of % ORAI1 gene expression consequence of siRNA mechanism of action.

Human A204 and murine C2C12 cells were transfected with increasing doses of SEQ ID NO. 112 (19 bp blunt ended dsRNA structure, SYL116011) and SEQ ID NO. 227 (19 bp blunt ended dsRNA structure, SYL116011v8) (0.001 to 100 nM) with Transit TKO and Lipofectamine 2000 respectively as transfection agent. All transfections were done following standard manufacturer's conditions. In the same transfection a scrambled siRNA sequence was used as specific control of interference. Cell pellets were collected and processed to evaluate possible variations in mRNA levels as a consequence of siRNA mechanism of action. RNA levels were quantified by real-time PCR using a relative quantitation method, the Comparative Threshold 2-ΔΔ $C_T$ method. {Livak and Schmittgen, 2001}. All real time quantitative PCR experiments were performed in triplicate and repeated in three independent experiments. Mean and SEM were calculated. As FIG. 9 shows, a significant reduction in ORAI1 levels was observed in human cells at the dose 0.5 nM. The maximum effect was seen in response to the dose 100 nM both SEQ ID NO. 112 and SEQ ID NO. 227. Small differences were observed for SEQ ID NO. 112 and SEQ ID NO. 227 between the concentrations 10 to 50 nM. SEQ ID NO. 227 reduced ORAI1 mRNA levels 60-80% while SEQ ID NO. 112 reduced ORAI1 mRNA levels 40-60%. No differences were observed between the concentrations of 0.05 to 0.001 nM. Using these data, the inhibitory concentration 50 (IC50) value was calculated to be 1.98 nM for SEQ ID NO. 227 and 5.3 nM for SEQ ID NO. 112.

Figure 10:
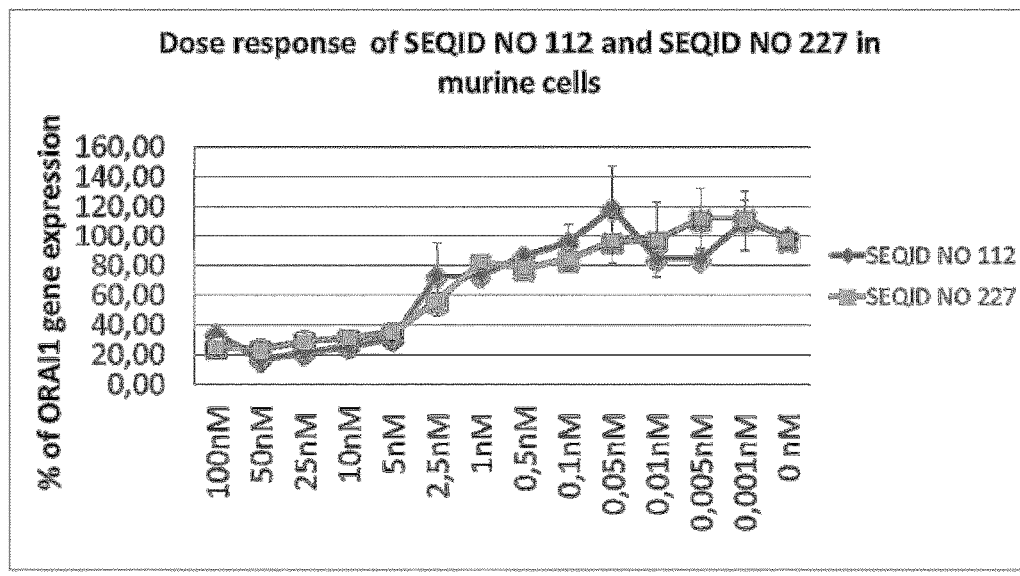
FIG. 10: shows the dose response of SEQ ID NO. 112 (SYL116011) and SEQ ID NO. 227 (SYL116011v8) in murine cells. Transfections of murine C2C12 cells with increasing doses (0.001 to 100 Nm) of SEQ ID NO. 112 (SYL116011) and SEQ ID NO. 227 (SYL116011v8) and quantification of % ORAI1 gene expression consequence of siRNA mechanism of action.

As FIG. 10 shows, a significant reduction in ORAI1 levels was also observed in murine C2C12 cells at the dose 2.5 nM. The maximum effect was seen in response to the dose 50 nM both SEQ ID NO. 112 and SEQ ID NO. 227. Small differences were observed for SEQ ID NO. 112 and SEQ ID NO. 227 between the concentrations 5 to 100 nM. Both SEQ ID NO. 112 and SEQ ID NO. 227 reduced ORAI1 mRNA levels 70-80% No differences were observed between the concentrations of 0.1 to 0.001 nM. Using these data, the inhibitory concentration 50 (IC50) value was calculated to be 1.98 nM for SEQ ID NO. 227 and 1.25 nM for SEQ ID NO. 112.

1.5 Expression of ORAI1 and its Paralogues ORAI2 and ORAI3 After Transfection of SEQ ID NO. 112 and SEQ ID NO. 227.

Figure 11:
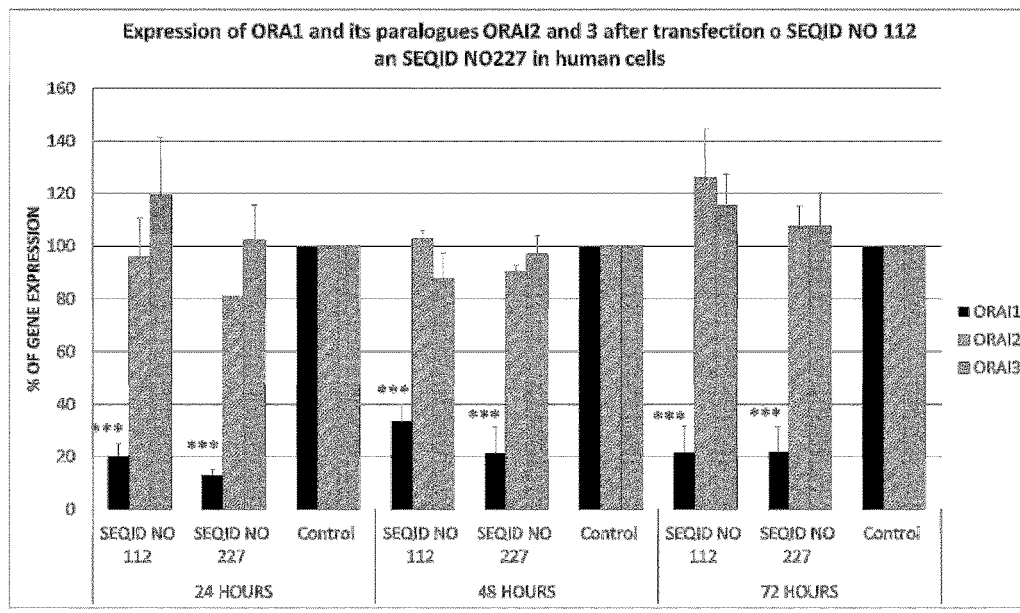
FIG. 11: shows the expression of ORAI1 and its paralogues ORAI2 and ORAI3 after transfection of SEQ ID NO. 112 (SYL116011) and SEQ ID NO. 227 (SYL116011v8) in human cells. Transfection of SEQ ID NO. 112 and SEQ ID NO. 227 in human A204 cells and quantification of % ORAI1, ORAI2 and ORAI3 gene expression consequence of siRNA mechanism of action.
Figure 12:
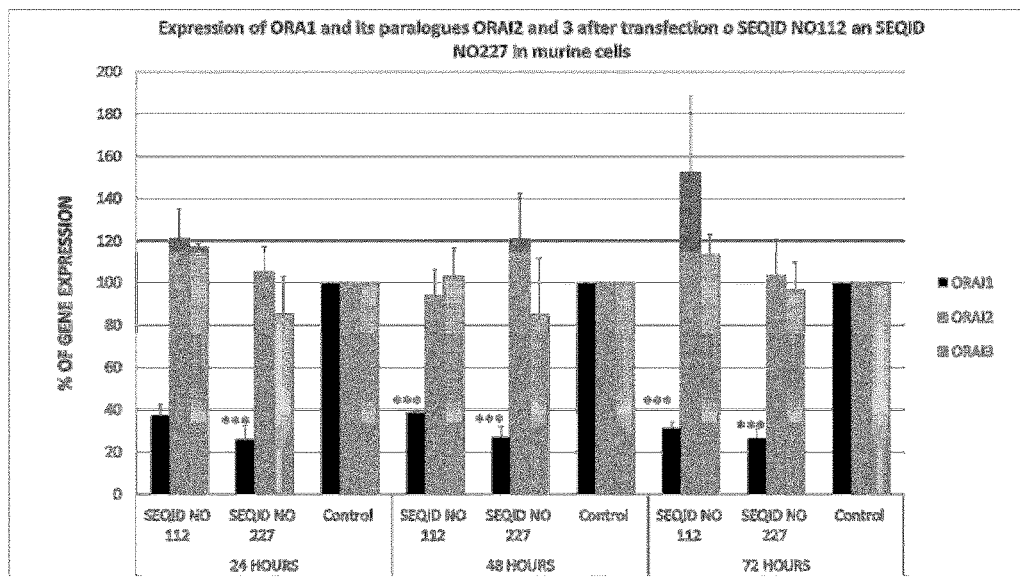
FIG. 12: shows the expression of ORAI1 and its paralogues ORAI2 and ORAI3 after transfection of SEQ ID NO. 112 (SYL116011) and SEQ ID NO. 227 (SYL116011v8) in murine cells. Transfection of SEQ ID NO. 112 and SEQ ID NO. 227 in C2C12 murine cells and quantification of % ORAI1, ORAI2 and ORAI3 gene expression consequence of siRNA mechanism of action.

In order to demonstrate the specific silencing effect of the siRNAs of the present invention, in vitro ORAI1, ORAI2 and ORAI3 expression levels were measured after transfection of a selection of siRNAs of the present invention in different cell lines. We analyzed the effect of SEQ ID NO. 112 and SEQ ID NO. 227 on receptors of the ORAI channels family to analyze its effect on proteins that are structurally and functionally related to ORAI1 channel. mRNA levels of ORAI1, ORAI2, and ORAI3 were assessed in human A204 and C2C12 murine cells after treatment with SEQ ID NO. 112 and SEQ ID NO. 227. Human A204 and murine C2C12 cells were transfected with 100 nM of SEQ ID NO 112 and SEQ ID NO 227 with Transit TKO and Lipofectamine 2000 respectively as transfection agents. All transfections were done following standard manufacturer's conditions. In the same transfection a scrambled siRNA sequence was used as specific control of interference. Cell pellets were collected at 24, 48, and 72 hours after transfection experiment and processed to evaluate possible variations in mRNA levels as a consequence of siRNA mechanism of action. FIG. 11 and FIG. 12 show that SEQ ID NO. 112 and SEQ ID NO. 227 were able to selectively decrease the levels of ORAI1 mRNA, 70-80% approximately in human cells, without significantly affecting mRNA levels of ORAI2 or ORAI3 (FIG. 11), and 60-70% in murine cells (FIG. 12).

1.6 Expression of Putative OTEs after Transfection of SEQ ID NO. 112 (SYL116011) in Human Cells.

Figure 13:
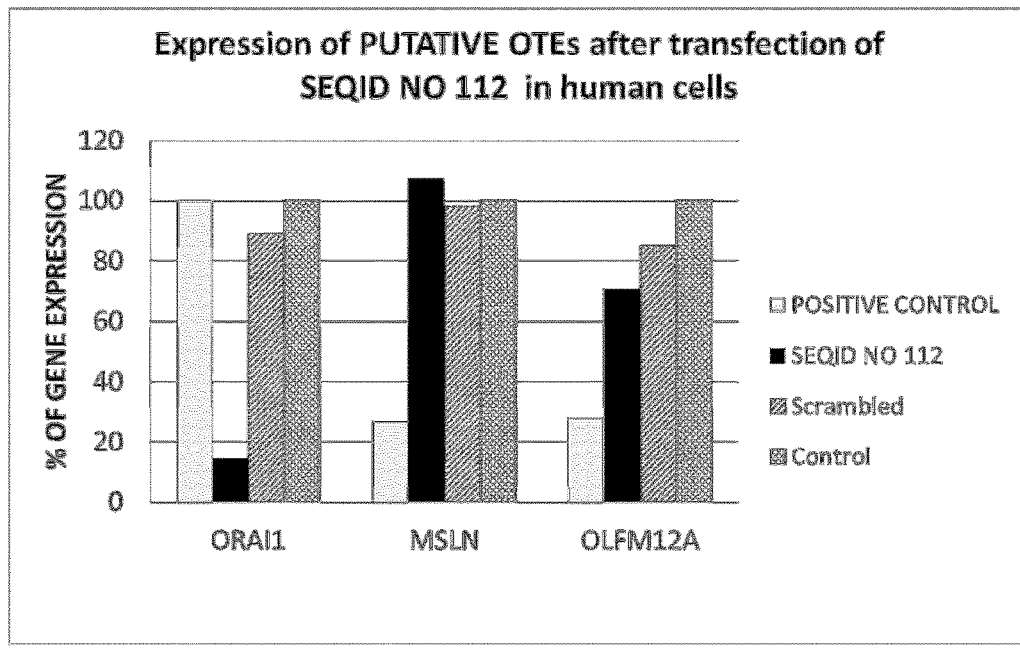
FIG. 13: shows the expression of putative OTEs after transfection of SEQ ID NO. 112 (SYL116011) in human cells. Transfection of SEQ ID NO. 112 in human A204 cells and quantification of % ORAI1, MSLN and OLFM12A gene expression consequence of siRNA mechanism of action.

In order to demonstrate the specific silencing effect of the siRNAs of the present invention regarding unintended targets, putative in silico off-targets effects (OTEs) for SEQ ID NO. 112 were determined in human cell lines. MSLN and OLFM12A expression levels were measured after transfection of a selection of siRNAs of the present invention in human cell lines. We analyzed the effect of SEQ ID NO. 112 on MSLN and OLFM12A gene expression. mRNA levels of MSLN and OLFM12A were assessed in human A204 cells after treatment with 100 nM of SEQ ID NO. 112 with Transit TKO as transfection agents. All transfections were done following standard manufacturer's conditions and with positive and negative controls. In the same transfection a scrambled siRNA sequence was used as specific control of interference. Cell pellets were collected at 24, 48, and 72 hours after transfection experiment and processed to evaluate possible variations in putative OTEs mRNA levels as a consequence of SEQ ID NO. 112 mechanism of action. FIG. 13 shows that SEQ ID NO. 112 did not decrease the levels of putative OTEs.

Figure 14:
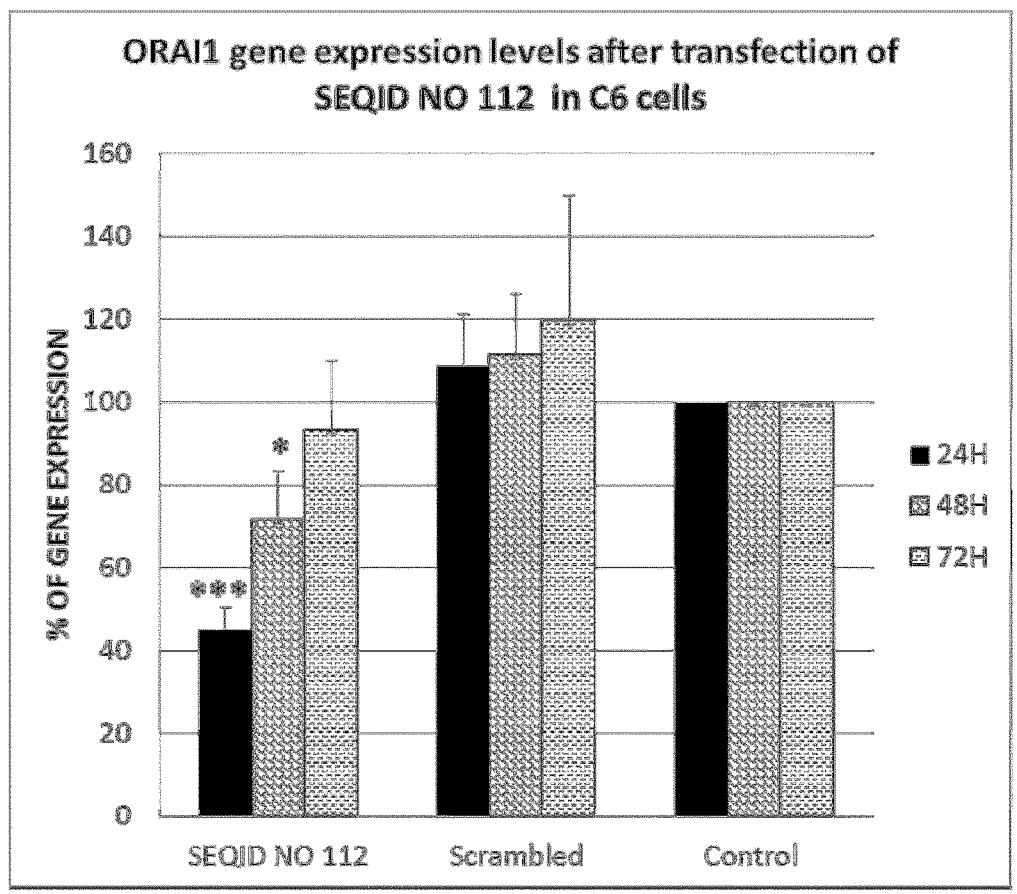
FIG. 14: shows ORAI1 expression levels after transfection of SEQ ID NO. 112 (SYL116011) in rat cell lines. Transfection of SEQ ID NO. 112 in rat C6 cells and quantification of % ORAI1 gene expression consequence of siRNA mechanism of action.
Figure 15:
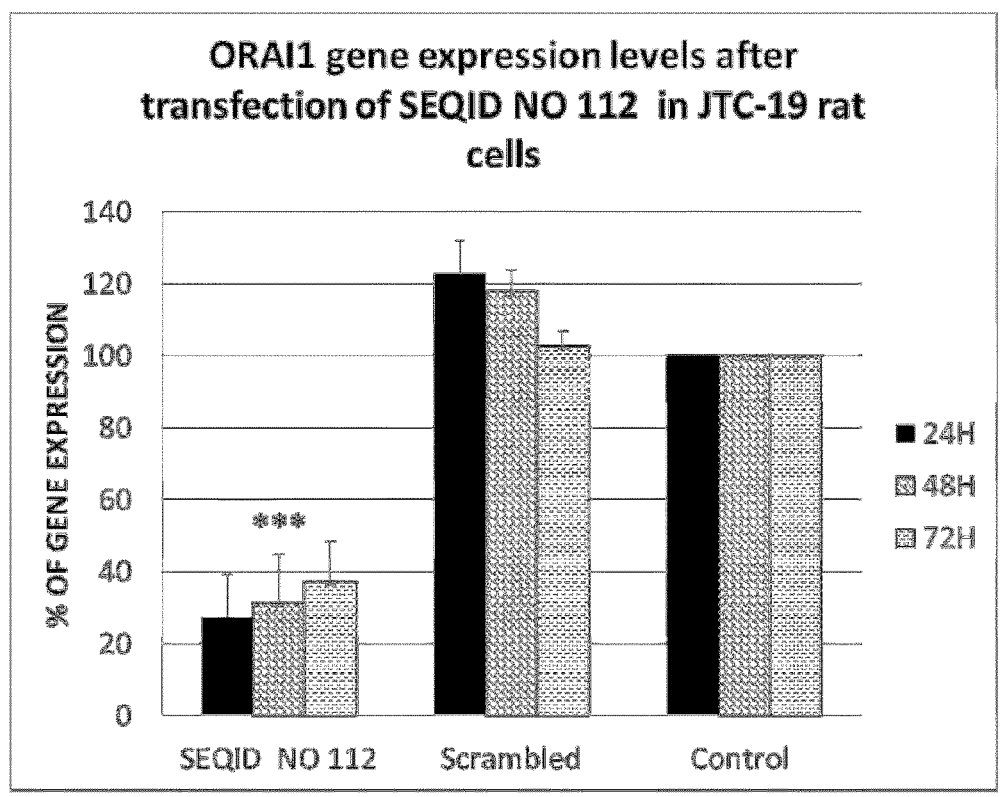
FIG. 15: shows ORAI1 expression levels after transfection of SEQ ID NO. 112 (SYL116011) in rat cell lines. Transfection of SEQ ID NO. 112 in rat JTC-19 cells and quantification of % ORAI1 gene expression consequence of siRNA mechanism of action.

1.7 ORAI1 Expression Levels after Transfection of SEQ ID NO. 112 in Rat Cell Lines In order to demonstrate the silencing effect of the SEQ ID NO. 112, in vitro ORAI1 expression levels were measured after transfection of a selection of siRNAs of the present invention in different cell lines. Rat JTC-19 and C6 cells were transfected with 100 nM of SEQ ID NO. 112 with Transit IT2020 and Lipofectamine 2000 respectively, as transfection agents. All transfections were done following standard manufacturer's conditions with a negative control. In the same transfection a scrambled siRNA sequence was used as specific control of interference. Cell pellets were collected at 24, 48, and 72 hours after transfection experiment and processed to evaluate possible variations in mRNA levels as a consequence of siRNA mechanism of action. RNA levels were quantified by real-time PCR using a relative quantitation method, the Comparative Threshold 2-ΔΔ CT method {Livak and Schmittgen, 2001}. All real time quantitative PCR experiments were performed in triplicate and repeated in three independent experiments. Mean and SEM were calculated. As FIG. 14 and FIG. 15 show SEQ ID NO. 122 reduced significantly ORAI1 mRNA levels approximately 70% in JTC-19 cells and 40-70% in C6 cells. For SEQ ID NO. 112 ORAI1 mRNA levels are not completely recovered at 72 hours in JTC-19 cells but not in C6 cells (FIG. 14 and FIG. 15).

1.8 Gene Expression Levels of ORAI1 after Transfection of SEQ ID NO. 112 (SYL116011), SEQ ID NO. 233 (SYL116011v11) and SEQ ID NO. 235 (SYL116011v11).

Figure 16:
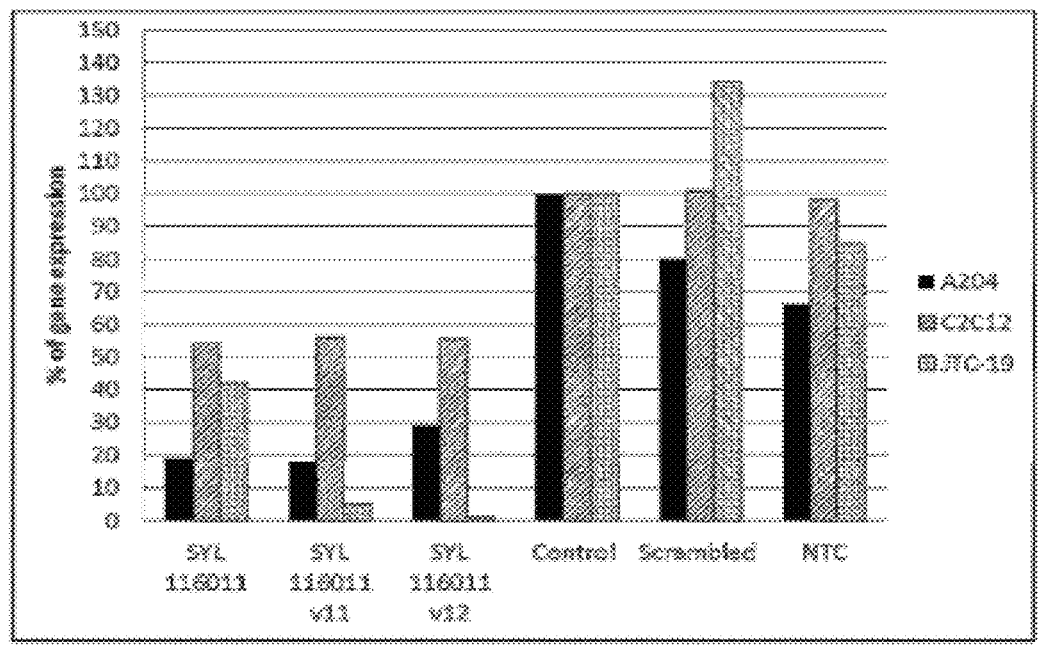
FIG. 16: shows gene expression levels of ORAI1 after transfection of SEQ ID NO. 112 (SYL116011), SEQ ID NO. 233 (SYL116011v11) and SEQ ID NO. 235 (SYL116011v11) in human, murine and rat cells.

Human A204, murine C2C12 and JTC-19 rat cells were transfected with 100 nM of SEQ ID NO. 112 (19 bp blunt ended dsRNA structure, SYL116011) and SEQ ID NO. 233 (19 bp blunt ended dsRNA structure, SYL116011v11) and SEQ ID NO. 235 (19 bp blunt ended dsRNA structure, SYL116011v12 with Transit TKO, Lipofectamine 2000 AND Mirus IT2020, respectively as transfection agent. All transfections were done following standard manufacturer's conditions. In the same transfection a scrambled siRNA sequence was used as specific control of interference. Cell pellets were collected and processed to evaluate possible variations in mRNA levels as a consequence of siRNA mechanism of action. RNA levels were quantified by real-time PCR using a relative quantitation method, the Comparative Threshold 2-ΔΔ $C_T$ method. {Livak and Schmittgen, 2001}. As FIG. 16 shows, substantial reductions in ORAI1 levels were observed in human, murine and rat cells. ORAI1 mRNA levels were reduced 70-80% in human cells for SEQ ID NO. 112 (SYL116011), SEQ ID NO. 233 (SYL116011v11) and SEQ ID NO. 235 (SYL116011v11). In murine cells, ORAI1 mRNA levels were reduced 50% for SEQ ID NO. 112 (SYL116011), SEQ ID NO. 233 (SYL116011v11) and SEQ ID NO. 235 (SYL116011v11), while in rat cells were reduced 50% for SEQ ID NO. 112 (SYL116011) and 95% and 99% for SEQ ID NO. 233 (SYL116011v11) and SEQ ID NO. 235 (SYL116011v11) respectively.

2. In Vivo Analysis 2.1 Analysis of the Efficacy in Vivo of SEQ ID NO. 112 (SYL116011) and SEQ ID NO. 227 (SYL116011v8) in a Mouse Model of Ocular Allergy Induced by Ragweed Pollen.

The objective of the present study was to analyze the efficacy of the siRNAs of the present invention designed to silence expression of ORAI1, specifically SEQ ID NO. 112 (19 bp blunt ended dsRNA structure, SYL116011) and SEQ ID NO. 227 (19 bp blunt ended dsRNA structure, SYL116011v8) to reduce symptoms associated with ocular allergies in a mouse model of ocular allergy induced by ragweed pollen.

Ragweeds are flowering plants in the genus Ambrosia in the sunflower family Asteraceae. Ragweed pollen is highly allergenic, generally considered the greatest aeroallergen of all airborne pollens and the prime cause of hay fever worldwide. The National Institute of Environmental Health Science (NIEHS) indicates that ragweed and other weeds such as curly dock, lambs quarters, pigweed, plantain, sheep sorrel and sagebrush are some of the most prolific producers of pollen allergens around the world. This pollen is commonly used in animal models for studying allergic conjunctivitis {Bacsi A et al 2005}.

The aim of this analysis was to determine if down regulation of ORAI1 by ocular instillation of compounds of the present invention (SEQ ID NO. 112 (SYL116011) and SEQ ID NO. 227 (SYL116011v8)) alleviates the symptoms caused by ragweed pollen-induced ocular allergy in mice.

We have analysed whether ORAI1 is expressed in the mouse eye and if its expression is up-regulated in response to ragweed pollen-induced ocular allergy. We have also assessed the effect of silencing the expression of ORAI1 using locally applied SEQ ID NO. 112 (SYL116011) or SEQ ID NO. 227 (SYL116011v8) on allergy response in the above mentioned mouse model. For this purpose the following parameters have been analyzed:

Clinical signs in response to allergy induction: typical ocular signs of allergic conjunctivitis include itching, eyelid swelling, conjunctival swelling (chemosis), and mucus deposition. Mucus associated to ocular allergies is profuse, stringy and even sticky. Alterations to the conjunctiva usually cause the bulbar conjunctiva to take on a "glassy" appearance and the colouring of the palpebral conjunctiva is more pink than red with a frequently milky appearance.

Number of local mast cells: minutes after allergic stimulation conjunctival mast cells degranulate; the release of inflammatory mediators attracts more mast cells that migrate from deeper layers of the conjunctiva.

Local infiltration of eosinophils: infiltration of inflammatory cells to the conjunctiva occurs hours after allergen exposure and is part of the late response to allergens. Although several different types of cells migrate to the conjunctiva the main type are eosinophils.

Expression Changes in Molecular Biomarkers Related to Allergy:

Thymic stromal lymphopoietin (TLSP) is an epithelium-derived cytokine that activates dendritic cells by binding to its specific receptor TLSPR. Binding of TLSP to TLSPR induces an inflammatory Th2-type response. TLSP is produced primarily by epithelial cells but can also be produced by mast cells and has been found to be up-regulated at sites of allergic inflammation {Zheng X. et al 2010}.

Tumor necrosis factor receptor superfamily, member 9 (Tnfrsf9) or CD-137 is a costimulator of memory T cells. This costimulator is expressed in activated T cells, NK cells and dendritic cells (DC), while its ligand CD137L has been detected on mature DC, activated macrophages and activated B cells. CD-137 costimulates T cell activation and proliferation, enhances survival of activated T cells and suppresses CD4+ T help. In allergic inflammation it has been shown to mediate IL-4 dependent Th2 responses and is up-regulated in eosinophils of patients with IgE mediated allergic responses.

A. Methods a.1 Test System Characterisation

TABLE 1

Test system characterisation

| | |
|---|---|
| Species: | Mouse |
| Strain: | BALB-C |
| Sex: | Female |
| Colour: | White |
| Rationale for selection of species/strain: | This strain has been previously been established as a good model for ocular allergies {Bacsi A. et al 2005}. |
| Approx. age of the animals at the beginning of the study: | 8-10 weeks |

A further advantage of the siRNAs of the present invention is that SEQ ID NO. 1-SEQ ID NO. 8 correspond to highly conserved regions of the ORAI1 gene, throughout different animal sequences. In fact, these sequences are identical between human and mouse, making this animal model especially suitable for the study of for ocular allergies.

a.2 Induction of Allergy

Allergic conjunctivitis was induced by immunizing the animals with a mixture of 50 μg ragweed (Rw) pollen in 0.25 ml alum by intraperitoneal injection on day 1. The immunization solution was prepared immediately prior to administration and was protected from light at all times. Ten days after immunization 1.25 mg of Rw pollen was topically instilled into each eye. Administrations were performed in a dose volume of 5 μL/eye. This procedure was adapted from a standard preexisting published protocol known to an expert in the field and validated prior to assessing the efficacy of the siRNAs {Magone M. T. et al 1998}.

a.3 Test Item Administration

The test item was applied by the topical ocular route to both eyes of the animals once a day over a period of 5 days starting on day 6 (FIG. 4). A separate group of animals was administered with vehicle (PBS) and served as control. Administrations were performed in a dose volume of 5 μL/eye.

a.4 Clinical Observations and Collection of Samples

General health status of animals was monitored daily from first administration until sacrifice. Mice were examined for clinical signs of hypersensitivity prior to instillation of topical ocular pollen and at different time-points up to 24 h after pollen instillation. Conjunctival chemosis and injection, lid edema, discharge and tearing were graded on a scale 0-3. Clinical scoring was performed by an experimented observer blind to the experimental condition. Animals were sacrificed either 3 or 24 h after allergy challenge. Prior to sacrifice a sample of blood was collected in order to assess the presence of IgE, IL-13; IL-10 and MCP-1 in plasma. Following sacrifice eyes, spleen and cervical lymph nodes were isolated and either processed for histology, preserved in RNA later or processed for analyzing the levels of the above mentioned cytokines in conjunctiva.

a.5 Histopathology

The exenterated eyes were immersed in 10% formaline (1/20 volume) for 24 h hours, then the formaline was removed with several washes of phosphate buffer 0.1M and maintained almost 24 h hours in this buffer. Samples were dehydrated by incubating them in increasing concentrations of ethanol, and were thereafter embedded in low melting paraffin in a tissue processor (Leica TP 1020, Cat.no—0704 37101, Leica Microsystems, Nussloch, Germany). Samples were cut in a microtome to obtain sections of 2 μm that were thereafter stained with either toludine blue to count the number of mast cells or with hematoxyline-eosine to assess eosinophil infiltration.

a.6 RNA Isolation and Retrotranscription

Total RNA was isolated from whole eyes, spleen or lymph nodes using RNeasy RNA extraction kit (Invitrogen, CA, USA). 4 μg of total RNA were retrotranscribed using High-Capacity cDNA Archive kit (Applied Biosystems, Inc., Foster City, Calif., USA) according to the manufacturer's instructions and the IT-B-0003-01.

a.7 qPCR qPCR was performed using Stepone plus detection system (Applied Biosystems). 500 nanograms of each sample were amplified in a TaqMan 2× Universal Master Mix under the following conditions: 95° C. for 10 min, followed by 40 cycles of 95° C. for 15 s and 60° C. for 1 min. All qPCR amplifications were performed in triplicate and repeated in at least two independent experiments, always including reverse transcription controls and no template controls. ORAI1, TLSP and Tnfrsf9 mRNA levels were analyzed by qPCR using the ΔΔCT method of relative quantification using 18S gene as internal standard {Livak K. J. and Schmittgen T. D., 2001}.

a.8 Analysis of IgE, IL-13; IL-10 and MCP-1 in Plasma and Conjunctiva

The amount of the following cytokines IgE, IL-13, IL-10 and MCP-1 was assessed in plasma and conjunctiva of mice using the following kits and according to the manufacturer's instructions.

B. Results b.1 Expression of ORAI1 in Mouse Eye and Induction in Response to Ocular Allergy.

Figure 17:
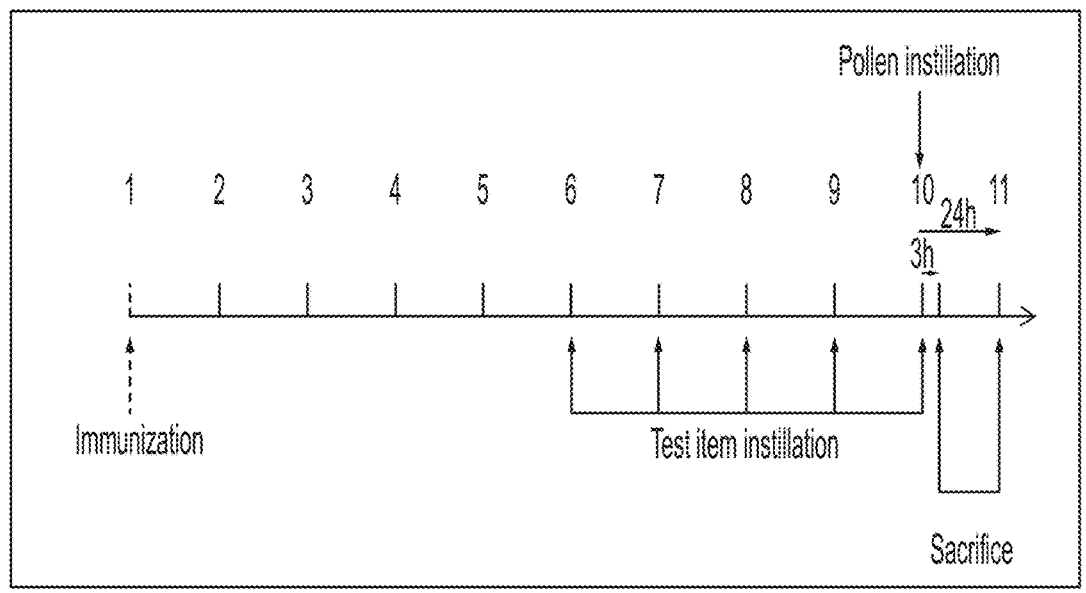
FIG. 17: Schedule of the in vivo assay.
Figure 18:
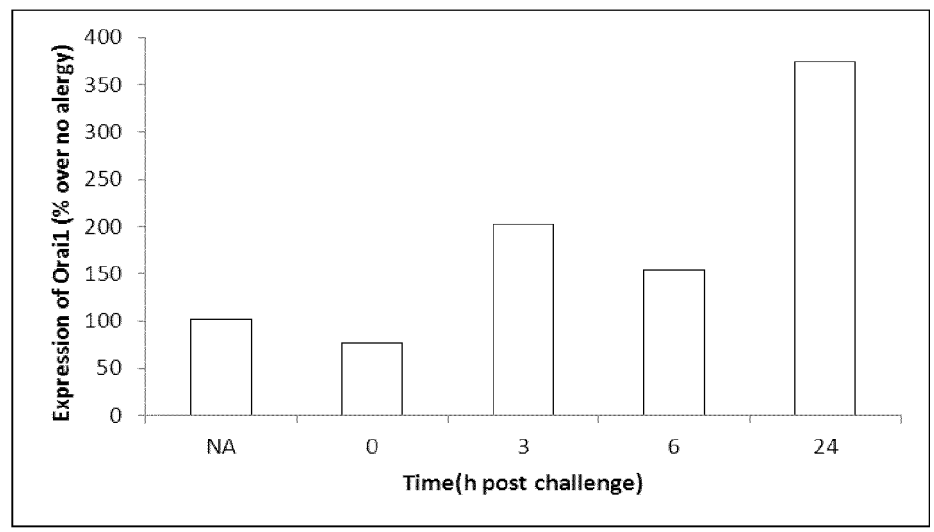
FIG. 18: Levels of ORAI1 mRNA in mouse whole eye at different times following induction of ocular allergy. NA: no allergy.
Figure 19:
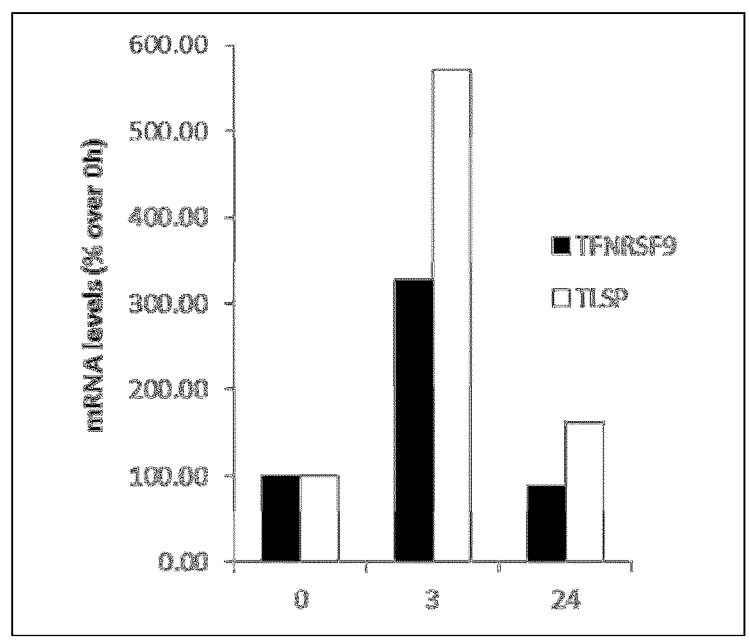
FIG. 19: mRNA levels of TLSP and Tnfrsf9 in a mouse model of ragweed-pollen induced allergy. mRNA levels are expressed as percentage of the levels observed prior to induction of allergy.

Expression of ORAI1 was assessed in eyes of mice at different time points after induction of allergy as mentioned in the methods section. FIG. 17 shows that ORAI1 is present in the eye and that its expression is rapidly up-regulated in response to the allergic challenge. A two-fold increase in ORAI1 mRNA levels was observed 3-6 h after administration of ragweed pollen. 24 h post challenge levels of ORAI1 were approximately 350% of the basal levels.

b.2 Assessment of Expression of Allergy Biomarkers in Response to Ocular Allergy.

mRNA levels of TLSP and Tnfrsf9 were studied at different time-points following induction of ocular allergy by instillation of ragweed pollen in pre-sensitized mice. A significant induction of both TLSP and Tnfrsf9 was observed 3 h post challenge. 24 h after induction Tnfrsf9 mRNA levels were close to baseline whereas mRNA levels of TLSP were still approximately 1.5 times above basal levels (FIG. 18).

b.3 Efficacy of SEQ ID NO. 112 (SYL116011) in a Mouse Model of Ocular Allergy

Figure 20:
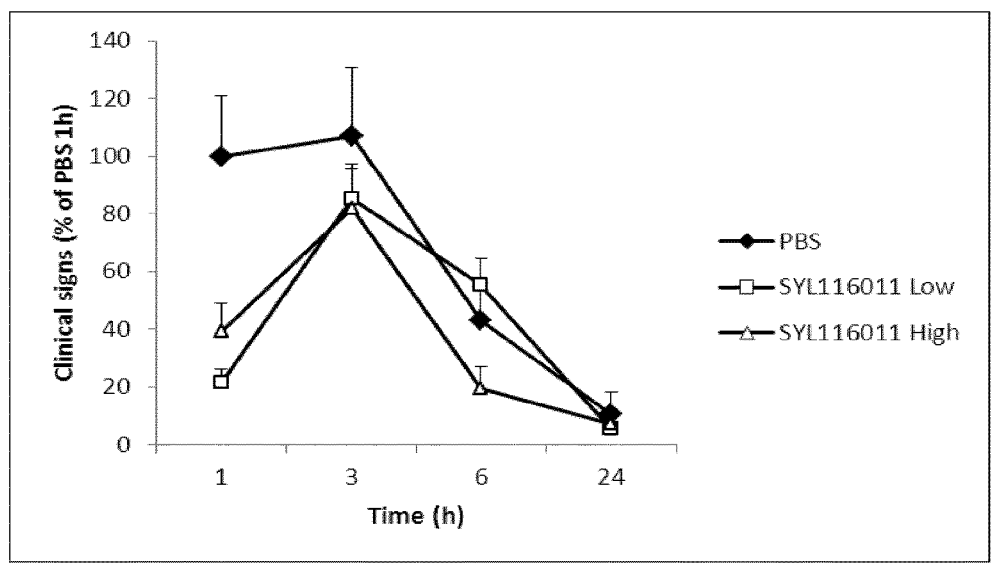
FIG. 20: Ocular clinical signs indicative of ocular allergy. Mice were observed 1, 3, 6 and 24 h after induction of ocular allergy. Clinical signs were assessed by grading the following parameters on a scale 0-3: conjunctival chemosis and injection, hyperemia, lid edema, discharge and tearing. Data are expressed as percentage of the clinical scoring at 1 h after induction of allergy of the PBS treated group and represent means±s.e.m of 8 animals for PBS and 15 animals for the SEQ ID NO. 112 (SYL116011) treated groups.

Three groups of animals were intraperitoneally (IP) injected with a dose of ragweed pollen adsorbed on alum as mentioned in the methods section. Five days after the IP injection one group (A, n=8) received an ocular instillation/day of PBS over a period of five days, the second group received SEQ ID NO. 112 (SYL116011) at the dose of 150 µg/eye/day (low dose) (B, n=15) during the same period of time whereas the third group received SEQ ID NO. 112 (SYL116011) at the dose of 375 µg/eye/day (high dose) over 5 days. Animals were examined for symptoms related to ocular allergy 1, 3, 6 and 24 h after ocular instillation of pollen. As shown in FIG. 20, treatments with either dose of SEQ ID NO. 112 (SYL116011) significantly reduced the immediate clinical signs of allergy. Further analysis of the clinical signs indicated that both doses of SEQ ID NO. 112 (SYL116011) had a particular effect on two of the parameters studied: chemosis (edema of the conjunctiva) and tearing (FIG. 21).

Infiltration of mast cells was assessed in palpebral and bulbar conjunctiva 3 h after induction of ocular allergy. SEQ ID NO. 112 (SYL116011) administered at the dose of 375 µg/eye/day caused a significant reduction in the number of mast cells infiltrating both the palpebral and bulbar conjunctiva (FIG. 22).

Eosinophil infiltration was assessed in conjunctiva at 24 h post challenge. Again, a significant decrease in infiltrating eosinophils was observed in response to the high dose of SEQ ID NO. 112 (SYL116011) in both regions of the conjunctiva and to the low dose in the bulbar conjunctiva (FIG. 23).

Analysis of the allergy biomarker TLSP in whole eye showed a dose-dependent reduction of the expression of this marker in response to SEQ ID NO. 112 (SYL116011). Expression of CD-137 (Tnfrsf9) was also significantly reduced in response to SEQ ID NO. 112 (SYL116011) 3 h post allergy challenge. As seen in FIG. 11 this allergy marker is significantly induced 3 h post allergy induction (FIG. 24).

b.4 Efficacy of SEQ ID NO. 227 (SYL116011v8) in a Mouse Model of Ocular Allergy

Furthermore, another in vivo experiment was performed in which three groups of animals were intraperitoneally (IP) injected with a dose of ragweed pollen adsorbed on alum as mentioned in the methods section. Five days after the IP injection one group (A, n=10) received an ocular instillation/day of PBS over a period of five days, the second group received another compound of the present invention (SEQ ID NO. 227 (SYL116011v8)), at the dose of 450 µg/eye/day (B, n=10) during the same period of time whereas the third group received 2 µL of 0.5 mg/ml levocabastine over 5 days. Levocabastine is a second generation H1 receptor antagonist currently marketed for the treatment of ocular allergies. Animals were examined for symptoms related to ocular allergy 0.5, 1, 3, 6 and 24 h after ocular instillation of pollen.

As shown in FIG. 25, treatment with SEQ ID NO. 227 (SYL116011v8) significantly reduced clinical signs of allergy; the reduction of clinical signs was greater to the one observed in response to levocabastine. Further analysis of the clinical signs indicated that SEQ ID NO. 227 (SYL116011v8) improves all the parameters studied when compared to PBS treated animals. Therefore this compound has proven to be an effective therapeutic treatment for ocular allergies.

2.2 Evaluation of the Effects in Vivo of SEQ ID NO. 112 (SYL116011) in a Murine Model for Experimental Allergic Conjunctivitis.

The objective of the present study was to evaluate the effects of the siRNAs of the present invention designed to silence expression of ORAI1, to reduce allergic symptoms like hyperemia, squinting, discharge, and lid swelling, associated to allergic conjunctivitis in a murine model.

The aim of this study was to evaluate if down regulation of ORAI1 by ocular instillation of SEQ ID NO. 112 (19 bp blunt ended dsRNA structure, SYL116011) alleviates allergic symptoms (hyperemia, squinting, discharge, and lid swelling) in a murine model of allergic conjunctivitis. As a positive control it was used a commonly used drug, the anti-allergic Patanol®. Patanol® (0.1% Olopatadine) is an anti-histamine/mast cell stabilizer dual-action administered as eye drops. Patanol® blocks the effects of histamine and prevents mast cells from releasing the chemicals responsible for allergy symptoms. Topical administration of PBS (vehicle) was used as a negative control.

A. Methods

In this study, female Balb/C mice were sensitized with short ragweed mixed with aluminum hydroxide on Day 0. On Day 18, mice were topically sensitized with short ragweed in balanced salt solution (BSS) prior to topical treatment to eliminate mice that were considered non-responders to challenge. Non-responders were mice that did not have at least a 2 unit change from baseline in hyperemia. Due to a low number of responders, mice were sensitized again on Day 21. On Day 24, the procedure for Day 18 was repeated in order to identify responders. Forty eight mice were chosen for the study and randomized into 6 groups, with 8 mice per group. Prophylactic treatment groups received their respective topical drugs on Days 25-27 (once daily for groups 2, 3 and 5; four times daily for group 6). On Days 28-31, mice were topically challenged with ragweed twice daily while receiving their respective drug (once daily for all groups except the Patanol® group, which received three doses daily). Animals were evaluated for hyperemia, squinting, discharge, and lid swelling with evaluations after the first, fourth, sixth, and eighth challenges.

a.1 Animals

The mice were housed in polycarbonate cages with direct contact bedding (ALPHA-dri®). The cages conformed to standards set forth in the Animal Welfare Act and the Guide for the Care and Use of Laboratory Animals. Space recommendations for animals were in accordance with PHS policy and the AWA. Litter or bedding in animal cages was changed as often as necessary to keep animals dry and clean.

Animals were fed food that is fresh, palatable and nutritionally adequate ad libitum. Water that is clean, potable, and uncontaminated was provided ad libitum. Environmental controls were set to maintain temperatures 22±4° C. (68±5° F.) with relative humidity of 50±20%. A 12-hour light/dark cycle was maintained. The animals were acclimated for at least 5 days after arrival at the facility prior to baseline evaluation. Staff veterinarian was not needed throughout the study.

a.2 Allergen Sensitization
   Route: Subcutaneous, both hind hocks.
   Frequency: On Day 0 and Day 21 for all groups.
   Procedure: For each sensitization, animals receiving SRW received 100 μg ragweed in 0.65 mg of aluminum hydroxide in 50 μL.
a.3 Dosing
   Topical treatment with SEQ ID NO. 112 (SYL116011), Patanol® as positive control or vehicle control was administered to all groups as outlined. Mice were dosed topically to the cornea using a calibrated micropipette, with a 3 μL drop of treatment in each eye. During the prophylactic treatment days (Days 25-27 Patanol® animals were dosed four times daily at approximately 9 am, 12 pm, 2 pm and 5 pm. All times were ±60 minutes and the exact timing of the dosing was noted in the study binder. Animals in groups 2, 3, 5 and 6 received their topical dose at approximately 1 pm±60 minutes. On challenge days (Days 28-31), Patanol® mice were given three times daily dosing on challenge days at approximately 9 am, 1 pm, and 4 pm; however, the time of dose was ±90 minutes. All other groups were dosed at approximately 1 pm. Again, the exact timing of dosing was recorded in the study binder.
a.4 Allergen Challenge
   Route: Ocular application, both eyes.
   Frequency: On Day 18, a screening SRW challenge was performed to identify responders. Mice were evaluated at baseline, prior to SRW challenge. Then 18±1 minutes post challenge, animals were evaluated again. Due to a lack of responders, the study was delayed. A second sensitization occurred on Day 21, and the screening SRW challenge was repeated on Day 24. On Days 25-27 groups 2, 3, 5 and 6 began their respective prophylactic treatments. On Days 28-31, the BID challenges occurred approximately 30 minutes after the $1^{st}$ daily Patanol® dose and after the $3^{rd}$ daily Patanol® dose. On Days 28-31, after topical dose 1 on Day 28 and after the third topical dose on days 29-31, animals were evaluated 30 minutes post Patanol® topical dose, then challenged ~3 minutes after evaluation, and evaluated again 18 minutes after challenge (post topical challenges 1, 4, 6, and 8).
   Procedure: Mice were challenged with topical doses of 150 μg of SRW (3 μl of 50 mg/mL) suspension in 3 μl balanced salt solution (BSS) in each eye. Animals were randomized based on their change from baseline hyperemia on Day 24.
a.5 Tissue Collection
   Animals were euthanized and after verification of death, the right eye and surrounding adnexa was removed and stored in Davidson's fixative for 24 hours. After 24 hours of fixation, the tissue was transferred to 70% ethanol for long term storage. Eyes were paraffin embedded and 1 H&E, 1 TBlue, and 1 unstained slide was made for each eye.
a.6 Statistical Methods
   The data were analyzed using a two-way ANOVA with Bonferroni post-test to compare the differences of the clinical signs among groups.
B. Results
   The data for hyperemia, squinting, lid swelling, and discharge are mean±SEM for N=8 eyes. The same masked observer evaluated the mice at challenges 1, 4, 6, and 8, which occurred on Study Days 28, 29, 30, and 31, respectively. For hyperemia, squinting, and discharge animals were evaluated on a 0-4 scale of severity (with 0 being normal and 4 being the worst). For lid swelling, mice were graded on a scale of 0-2. For each endpoint, animals were evaluated 30 minutes post-dose (for Patanol® only) or just at baseline prior to challenge for that day (for all other groups). All groups were analyzed via two-way ANOVA with Bonferroni post-test and any statistical significance versus vehicle was noted with an asterisk.
b.1 Change from Post-Dose Hyperemia—SEQ ID NO. 112 (SYL116011) Prophylactic Versus Patanol® and Vehicle Prophylactic.
   Data are mean±SEM for n=8 eyes per group. Patanol® showed a statistically lower response after the first challenge on Day 28 (p<0.01). Prophylactic doses of SEQ ID NO. 112 (SYL116011) showed a trend similar to that have Patanol®, but no statistical significance was noted (see FIG. 26).
b.2 Change from Post-Dose Squinting—SEQ ID NO. 112 (SYL116011) Prophylactic Versus Patanol® and Vehicle Prophylactic.
   Data are mean±SEM for n=8 eyes per group (see FIG. 27). No statistical significance was noted.
b.3 Change from Post-Dose Lid Swelling—SEQ ID NO. 112 (SYL116011) Prophylactic Versus Patanol® and Vehicle Prophylactic.
   Data are mean±SEM for n=8 eyes per group (see FIG. 28). No statistical significance was noted.
b.4 Change from Post-Dose Discharge—SEQ ID NO. 112 (SYL116011) Prophylactic Versus Patanol® and Vehicle Prophylactic.
   Data are mean±SEM for n=8 eyes per group (see FIG. 29). No statistical significance was noted.
C. Conclusions
   At the conclusion of the study, it appears as though SEQ ID NO. 112 (SYL116011) prophylactic followed the same trend of reduced hyperemia, lid swelling, and discharge (see FIGS. 26-29), however is not statistically significant when analyzing these data with two-way ANOVA with Bonferroni post-test due to the low N used in the study.
   What is remarkable is that when evaluating the effects of SEQ ID NO. 112 (SYL116011) of the present invention designed to silence expression of ORAI1, the results showed a similar trend in the dose-response in the SEQ ID NO. 112 (SYL116011) group, as the group treated with Patanol®, a known anti-allergic drug currently in the market, reducing in both cases the allergic symptoms associated to allergic conjunctivitis in a murine model. It is expected that with a higher N, the analysis of the data become statistically significant.

REFERENCES

Angaji S. A, Hedayati S. S, Poor R. H, et al. "Application of RNA interference in treating human diseases" *J Genet.* 2010. Vol. 89. 4. 527-37.

Baba Y, Nishida K, Fujii Y, Hirano T, et al. "Essential function for the calcium sensor STIM1 in mast cell activation and anaphylactic responses". *Nat Immunol.* 2008; 9:81-88.

Bacsi A, Dharajiya N, Choudhury B K, et al. "Effect of pollen-mediated oxidative stress on immediate hypersensitivity reactions and late-phase inflammation in allergic conjunctivitis." *J Allergy Clin Immunol.* 2005 October; 116(4):836-43.

Baumann T K & Martenson M E. "Extracellular protons both increase the activity and reduce the conductance of capsaicin-gated channels." *J Neurosci.* 2000. 20:RC80.

Bergmeier W, Weidinger C, Zee I, Feske S. "Emerging roles of store-operated Ca (2+) entry through STIM and ORAL proteins in immunity, hemostasis and cancer" *Channels* (Austin). 2013 Mar. 19; 7(4).

Bramsen J. B., Laursen M. B., Nielsen A. F., et al. 2009 "A large-scale chemical modification screen identifies design rules to generate siRNAs with high activity, high stability and low toxicity" *Nucleic Acids Res* Vol. 37 Issue: 9 Pages: 2867-81.

Caterina et al. "The capsaicin receptor: a heat-activated ion channel in the pain pathway." *Nature.* 1997 389(6653): 816-24.

Caterina et al. "The vanilloid receptor: a molecular gateway to the pain pathway." *Annual Rev Neurosci.* 2001 24:487-517.

Cerutti, L., N. Mian, et al. "Domains in gene silencing and cell differentiation proteins: the novel PAZ domain and redefinition of the Piwi domain." *Trends Biochem Sci.* 2000 25(10): 481-2.

Collins, R. E. and X. Cheng. "Structural domains in RNAi." *FEES Lett* 2005 579(26): 5841-9.

Chang C. I, Kim H. A, Dua P, et al. "Structural Diversity Repertoire of Gene Silencing Small Interfering RNAs" *Nucleic Acid Ther.* 2011. Vol. 21. 3. 125-31

Deleavey G. F and Damha M. J. "Designing chemically modified oligonucleotides for targeted gene silencing". *Chem Biol.* 2012 Vol. 19.8. 937-54.

Doench, J. G. Sharp, P. A. "Specificity of microRNA target selection in translational repression" *Genes Dev.* 2004 18, 504-511.

Elbashir, S. M., W. Lendeckel, et al. "RNA interference is mediated by 21- and 22-nucleotide RNAs." *Genes Dev.* 2001 15(2): 188-200.

Fire, A., S. Xu, et al. "Potent and specific genetic interference by double-stranded RNA in *Caenorhabditis elegans.*" *Nature.* 1998 391(6669): 806-11.

Gonzalez, G. G., Garcia, P. et al. "Reduction of capsacin-induced ocular pain and neurogenic inflammation by calcium antagonists." *Invest Ophthalmol Vis Sci.* 1993 34(12):3329-3335.

Hoth M, Penner R. "Depletion of intracellular calcium stores activates a calcium current in mast cells". *Nature.* 1992; 355:353-356.

Huang W C, Chai C Y, Chen W C, et al. "Histamine regulates cyclooxygenase 2 gene activation through Orai1-mediated NFκB activation in lung cancer cells" *Cell Calcium.* 2011 July; 50(1):27-35

Hutvagner, G. and P. D. Zamore. "A microRNA in a multiple-turnover RNAi enzyme complex." *Science.* 2002. 297(5589): 2056-60.

Kari O. and Saari K M. "Updates in the treatment of ocular allergies". *Journal of Asthma and Allergy* 2010: 3 149-158.

Key B. Allergy and allergic diseases. Part I. *N. Engl J Med.* 2001; 344:30-37.

Kim D. H., Behlke M. A., Rose S. D., et al. "Synthetic dsRNA Dicer substrates enhance RNAi potency and efficacy" *Nat Biotechnol* 2005. Vol. 23 Issue: 2 Pages: 222-6.

Kornbrust D, Cavagnaro J, Levin A, et al. "Oligo safety working group exaggerated pharmacology subcommittee consensus document" *Nucleic Acid Ther* 2013 Vol. 23, 1, Pag: 21-8.

La Rosa M, Lionetti E, Reibaldi M, et al. "Allergic conjunctivitis: a comprehensive review of the literature" *Italian Journal of Pediatrics* 2013, 39:18.

Lewis, B. P., Shih I. et al. "prediction of mammalian micro RNA targets." *Cell.* 2003 115:787-798.

Liu, J., M. A. Carmell, et al. "Argonaute2 is the catalytic engine of mammalian RNAi." *Science.* 2004 305(5689): 1437-41.

Livak K. J. and Schmittgen T. D., "Analysis of relative gene expression data using real-time quantitative PCR and the 2(-Delta Delta C(T)) Method" *Methods.* 2001; Vol: 25, Issue: 4, Pages: 402-8.

Ma, J. B., Y. R. Yuan, et al. "Structural basis for 5'-end-specific recognition of guide RNA by the A. fulgidus Piwi protein." *Nature.* 2005 434(7033): 666-70.

Magone M T, Chan C C, Rizzo L V, Kozhich A T, Whitcup S M. "A novel murine model of allergic conjunctivitis". *Clin Immunol Immunopathol.* 1998; 87:75-84.

Maniatis, T., et al., "Molecular Cloning: A Laboratory Manual". *Cold Spring Harbor Laboratory,* 1982, at pages 387-389.

Montell et al. "Short hairpin RNAs (shRNAs) induce sequence-specific silencing in mammalian cells." *Genes Dev.* 2002 16(8):948-58.

Nykanen, A., B. Haley, et al. "ATP requirements and small interfering RNA structure in the RNA interference pathway." *Cell* 2001 107(3): 309-21.

Ono S J, Abelson M B. "Allergic conjunctivitis: update on pathophysiology and prospects for future treatment" *J. Allergy Clin. Immunol.* 2005, 75(1), 1 18-122.

Orban, T. I. and E. Izaurralde. "Decay of mRNAs targeted by RISC requires XRN1, the Ski complex, and the exosome." *Rna.* 2005 11(4): 459-69.

Parekh A B, Putney J W, Jr. "Store-operated calcium channels". *Physiol Rev* 2005; 85:757-810.

Parrish, S., J. Fleenor, et al. "Functional anatomy of a dsRNA trigger: differential requirement for the two trigger strands in RNA interference." *Mol Cell.* 2000 6(5): 1077-87.

Popescu F D. "Antisense- and RNA interference-based therapeutic strategies in allergy" *J Cell Mol Med.* 2005 October-December; 9(4):840-53.

Rand, T. A., S. Petersen, et al. "Argonaute2 cleaves the anti-guide strand of siRNA during RISC activation." *Cell.* 2005 123(4): 621-9.

Reynolds, A., Leake, D., et al. "Rational siRNA design for RNA interference" *Nat Biotechnol.* 2004 22(3):326-30.

Sanghvi Y. S. "A status update of modified oligonucleotides for chemotherapeutics applications" *Curr Protoc Nucleic Acid Chem.* 2011 Vol. 4. 4 1 1-22.

Schubert, S. et al. "Local RNA target structure influences siRNA efficacy: systematic analysis of intentionally designed binding regions." *J Mol Biol.* 2005 348:883-893.

Smyth J T, Dehaven W I, Jones B F, et al. "Emerging perspectives in store-operated Ca2+ entry: roles of Orai, Stim and TRP". *Biochim Biophys Acta* 2006; 1763:1147-1160.

Song, J. J., S. K. Smith, et al. "Crystal structure of Argonaute and its implications for RISC slicer activity." *Science.* 2004 305(5689): 1434-7.

Suzuki M, Zheng X, Zhang X, et al. "Inhibition of allergic responses by CD40 gene silencing" *Allergy.* 2009 March; 64(3):387-97.

Suzuki M, Zheng X, Zhang X, et al. "A novel allergen-specific therapy for allergy using CD40-silenced dendritic cells" *J Allergy Clin Immunol.* 2010 March; 125(3):737-43.

Ui-Tei, K., Naito, Y., et al. "Guidelines for the selection of highly effective siRNA sequences for mammalian and chick RNA interference." *Nucleic Acids Res.* 2004 32(3): 936-48.

Vig M, DeHaven W I, Bird G S, et al. "A major defect in mast cell effector functions in CRACM1−/− mice" *Nat Immunol.* 2008 January; 9(1):89-96.

Walton S. P, Wu M, Gredell J. A and Chan C. "Designing highly active siRNAs for therapeutic applications" *FEBS J.* 2010. Vol. 277. 23. 4806-13.

Wang Y, Lin L, Zheng C. "Downregulation of Grail expression in the airway alleviates murine allergic rhinitis" *Exp Mol Med.* 2012 March 31; 44(3):177-90.

Yang I-H, Tsai Y-T et al. "Involvement of STIM1 and ORAI1 in EGF-mediated cell growth in retinal pigment epithelial cells" *Journal of Biomedical Science.* 2013; 20:41.

Zheng X, Ma P, de Paiva C S, et al. TSLP and downstream molecules in experimental mouse allergic conjunctivitis. *Invest Ophthalmol Vis Sci* 2010; 51:3076-3082.

The invention claimed is:

1. A method of treating an eye condition characterized by increased expression and/or activity of ORAI1 in a subject in need thereof, the method comprising: topically administering to the corneal surface of the eye of the subject an amount of an siRNA molecule that specifically targets the sequence of SEQ ID NO. 1 effective to decrease the expression and/or activity of ORAI1 in cells of the eye and to treat the eye condition, wherein said eye condition is an ocular allergy and/or conjunctivitis.

2. The method according to claim 1, wherein said eye condition is selected from seasonal allergic conjunctivitis, perennial allergic conjunctivitis, vernal keratoconjunctivitis, atopic keratoconjunctivitis, giant papillary conjunctivitis, dry eye syndrome, or a combination thereof.

3. The method according to claim 1, wherein said siRNA comprises a 19 nucleotide double-stranded region.

4. The method according to claim 3, wherein said siRNA is blunt-ended.

5. The method according to claim 3, wherein said siRNA includes the nucleotide sequence set forth in SEQ ID NO. 112.

6. The method according to claim 4, wherein the siRNA includes the nucleotide sequence set forth in SEQ ID NO. 112.

7. The method according to claim 3, wherein at least one nucleotide of said siRNA molecule comprises a chemical modification.

8. The method according to claim 7, wherein said chemical modification is selected from the group consisting of 2'-O-methylation; substitution of uracyl ribose nucleotides with deoxythymidine nucleotides; and combinations thereof.

9. The method according to claim 8, wherein said chemical modification is on the sense strand, the antisense strand, or on both the sense and the antisense strand.

10. The method according to claim 9, wherein said siRNA has a nucleotide sequence selected from SEQ ID NO. 223 to SEQ ID NO. 229, SEQ ID NO: 233, and SEQ ID NO: 235.

11. The method according to claim 1, wherein said siRNA molecule is a double stranded, blunt-ended siRNA molecule consisting of 19 nucleotides, which comprises at least one sequence selected from SEQ ID NO. 112, SEQ ID NO. 223 to SEQ ID NO. 229, SEQ ID NO: 233, and SEQ ID NO: 235.

12. The method according to claim 11, wherein said eye condition is selected from the group consisting of seasonal allergic conjunctivitis, perennial allergic conjunctivitis, vernal keratoconjunctivitis, atopic keratoconjunctivitis, giant papillary conjunctivitis, dry eye syndrome and combinations thereof.

13. The method according to claim 11 wherein the siRNA includes the nucleotide sequence set forth in SEQ ID NO. 112.

14. The method according to claim 11, wherein at least one nucleotide of said siRNA molecule comprises a chemical modification.

15. The method according to claim 14, wherein said chemical modification is selected from the group consisting of 2'-O-methylation; substitution of uracyl ribose nucleotides with deoxythymidine nucleotides; and combinations thereof.

16. The method according to claim 15, wherein said chemical modification is on the sense strand, the antisense strand, or on both the sense and the antisense strand.

17. The method according to claim 16, wherein the said siRNA has a nucleotide sequence selected from SEQ ID NO. 223 to SEQ ID NO. 229, SEQ ID NO: 233, and SEQ ID NO: 235.

18. The method according to claim 1, wherein said eye condition is allergic conjunctivitis.

* * * * *